US010106590B2

(12) United States Patent
Walensky et al.

(10) Patent No.: US 10,106,590 B2
(45) Date of Patent: Oct. 23, 2018

(54) BH4 STABILIZED PEPTIDES AND USES THEREOF

(71) Applicant: Dana-Farber Cancer Institutes, Inc., Boston, MA (US)

(72) Inventors: Loren D. Walensky, Newton Centre, MA (US); Michelle L. Stewart, Brookline, MA (US); Lauren Barclay, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/777,391

(22) PCT Filed: Mar. 14, 2014

(86) PCT No.: PCT/US2014/029318
§ 371 (c)(1),
(2) Date: Sep. 15, 2015

(87) PCT Pub. No.: WO2014/144768
PCT Pub. Date: Sep. 18, 2014

(65) Prior Publication Data
US 2016/0031959 A1    Feb. 4, 2016

Related U.S. Application Data

(60) Provisional application No. 61/792,188, filed on Mar. 15, 2013.

(51) Int. Cl.
*C07K 14/47* (2006.01)
*A61K 38/17* (2006.01)
*A61K 9/00* (2006.01)
*A61K 9/08* (2006.01)
*A61K 45/06* (2006.01)
*G01N 33/68* (2006.01)
*A61K 49/00* (2006.01)
*A61K 38/00* (2006.01)

(52) U.S. Cl.
CPC ........ *C07K 14/4747* (2013.01); *A61K 9/0019* (2013.01); *A61K 9/08* (2013.01); *A61K 38/1761* (2013.01); *A61K 45/06* (2013.01); *A61K 49/0008* (2013.01); *G01N 33/68* (2013.01); *A61K 38/00* (2013.01); *G01N 2333/47* (2013.01); *G01N 2500/04* (2013.01); *G01N 2500/20* (2013.01)

(58) Field of Classification Search
CPC .... A61K 38/00; A61K 38/1761; A61K 45/06; A61K 49/0008; A61K 9/0019; A61K 9/08; C07K 14/4747; G01N 2333/47; G01N 2500/04; G01N 2500/20; G01N 33/68
See application file for complete search history.

(56) References Cited

U.S. PATENT DOCUMENTS

| 5,446,090 A | 8/1995 | Harris |
| 5,789,201 A | 8/1998 | Guastella |
| 6,348,558 B1 | 2/2002 | Harris et al. |
| 7,723,468 B2 | 5/2010 | Daffre et al. |
| 7,723,469 B2 | 5/2010 | Walensky et al. |
| 2004/0067503 A1 | 4/2004 | Tan et al. |
| 2005/0250680 A1 | 11/2005 | Walensky et al. |
| 2010/0168388 A1 | 7/2010 | Bernal et al. |
| 2010/0273704 A1 | 10/2010 | Korsmeyer et al. |
| 2011/0318352 A1 | 12/2011 | Walensky |
| 2012/0270800 A1 | 10/2012 | Verdine et al. |

FOREIGN PATENT DOCUMENTS

| EP | 1997828 | 10/2017 | |
| WO | WO 2007/002217 A2 | 1/2007 | |
| WO | WO 2008/121767 | 10/2008 | |
| WO | WO 2009042237 A2 * | 4/2009 | ......... C07K 14/4747 |
| WO | WO 2009/108261 | 9/2009 | |
| WO | WO 2010/060112 | 5/2010 | |
| WO | WO 2010/068684 | 6/2010 | |
| WO | WO 2010/148335 | 12/2010 | |

OTHER PUBLICATIONS

Miki Hirotani, NH2-terminal BH4 Domain of Bcl-2 is Functional for Heterodimerization with Bax and Inhibition of Apoptosis, The Journal of Biological Chemistry vol. 274, No. 29, Issue of Jul. 16, pp. 20415-20420, 1999.*
ThermoFischer, Peptide Design, Posted online 2011.*
Altschul et al., "Gapped BLAST and PSI-BLAST: a new generation of protein database search programs," *Nucleic Acids Res.* 25(17):3389-3402 (1997).
Aristoteli et al., "Evaluation of endogenous plasma peptide extraction methods for mass spectrometric biomarker discovery," *Journal of Proteome Res.* 6(2):571-581 (2007).
Bang, et al., "Total chemical synthesis of crambin," *J. Am. Chem. Soc.* 126(5):1377-1383 (2004).
Bird et al., "Hydrocarbon double-stapling remedies the proteolytic instability of a lengthy peptide therapeutic," *Proc. Natl. Acad. Sci. U.S.A.* 107(32):14093-8 (2010).
Bird et. al., "Synthesis and Biophysical Characterization of Stabilized a-Helices of BCL-2 Domains," *Methods in Enzymology* 446:369-386 (2008).
Blackwell et al., "Ring-closing metathesis of olefinic peptides: design, synthesis, and structural characterization of macrocyclic helical peptides," *J. Org. Chem.* 66(16):5291-5302 (2001).

(Continued)

*Primary Examiner* — James H Alstrum-Acevedo
*Assistant Examiner* — Erinne R Dabkowski
(74) *Attorney, Agent, or Firm* — Fish & Richardson P.C.

(57) ABSTRACT

Provided herein are polypeptides containing stabilized BH4 domains of BCL-2 family proteins that are capable of binding and/or inactivating and/or modulating BAX protein, and/or its close homologs BAK and BOK, and/or other physiological BH4 targets. Also provided are compositions containing these polypeptides and methods of treating cytotoxic diseases that include administering to a subject one of the polypeptides.

6 Claims, 26 Drawing Sheets
Specification includes a Sequence Listing.

(56) References Cited

OTHER PUBLICATIONS

Braun et al., "Photoreactive stapled BH3 peptides to dissect the BCL-2 family interactome," *Chem. Biol.* 17(12):1325-1333 (2010).
Broglia et al., "Design of HIV-1-PR inhibitors that do not create resistance: blocking the folding of single monomers," *Protein Sci.* 14(10):2668-81 (2005).
Chipuk et al., "How do BCL-2 proteins induce mitochondrial outer membrane permeabilization?" *Trends Cell. Biol.* 18(4):157-164 (2008).
Cohen et al., "A competitive stapled peptide screen identifies a selective small molecule that overcomes MCL-1-dependent leukemia cell survival," *Chem. Biol.* 19(9):1175-1186 (2012).
Dejean et al., "Oligomeric Bax is a component of the putative cytochrome c release channel MAC, mitochondrial apoptosis-induced channel," *Mol. Biol. Cell.* 16(5):2424-2432 (2005).
Eng et al., "An approach to correlate tandem mass spectral data of peptides with amino acid sequences in a protein database," *J. Am. Soc. Mass Spectrom.* 5(11):976-989 (1994).
Gavathiotis et al., "BAX Activation is Initiated at a Novel Interaction Site," *Nature* 455:1076-1081, (2008).
Gavathiotis et al., "BH3-triggered structural reorganization drives the activation of proapoptotic BAX," *Molecular Cell* 40:481-492 (2010).
Hammond et al., "An examination of binding motifs associated with inter-particle interactions between facetted nano-crystals of acetyl-salicylic acid and ascorbic acid through the application of molecular grid-based search methods," *J. Pharm. Sci.* 98(12):4589-602 (2009).
Jürgensmeier et al., "Bax directly induces release of cytochrome c from isolated mitochondria," *Proc. Natl. Acad. Sci. U.S.A.* 95(9):4997-5002, (1998).
Kawamoto et al., "Design of triazole-stapled BCL9 α-helical peptides to target the β-catenin/B-cell CLL/lymphoma 9 (BCL9) protein-protein interaction," *J. Med. Chem.* 55(3):1137-1146 (2012).
Kuwana et al., "BH3 domains of BH3-only proteins differentially regulate Bax-mediated mitochondrial membrane permeabilization both directly and indirectly," *Mol. Cell* 17(4):525-535 (2005).
Nechushtan et al., "Conformation of the Bax C-terminus regulates subcellular location and cell death," *EMBO J.* 18(9):2330-2341 (1999).
Ng et al., "Revealing the way of self-complementary dimerization for a shape-persistent macrocycle using density functional theory calculations," *J. Phys. Chem. B.* 111(50):13886-93 (2007).
Petros et al., "Solution structure of the antiapoptotic protein bcl-2," *Proc. Natl. Acad. Sci. U.S.A.* 98(6):3012-3017 (2001).
Schafmiester et al., "An All-Hydrocarbon Cross-Linking System for Enhancing the Helicity and Metabolic Stability of Peptides," *J. Am. Chem. Soc.* 122:5891-5892, 2000.
Sedlak et al., "Multiple Bcl-2 family members demonstrate selective dimerizations with Bax," *Proc. Natl. Acad. Sci. U.S.A.* 92(17):7834-7838 (1995).
Suzuki et al., "Structure of Bax: Coregulation of Dimer Formation and Intracellular Localization," *Cell* 103:645-654 (2000).
Walden et al., "Analytical procedures for quantification of peptides in pharmaceutical research by liquid chromatography-mass spectrometry," *Analytical Bioanalytical Chemistry* 378($):883-897 (2004).
Walensky et al., "A stapled BID BH3 helix directly binds and activates BAX," *Mol. Cell* 24(2):199-210 (2006).
Walensky et al., "Activation of Apoptosis in Vivo by a Hydrocarbon-Stapled BH3 Helix," *Science* 305:1466-1470 (2004).
Wales et al. "High-speed and high-resolution UPLC separation at zero degrees Celsius," *Anal. Chem.* 80(17):6815-6820 (2008).
Wilen, et al., "Strategies in Optical Resolutions," *Tetrahedron* 33:2725 (1977).
Williams et al., "Asymmetric synthesis of monosubstituted and .alpha.,.alpha.-disubstituted .alpha.-amino acids via diastereoselective glycine enolate alkylation," *J. Am. Chem. Soc.* 113(24):9276-9286 (1991).
Williams et al., "Efficient asymmetric synthesis of N-tert-butoxycarbonyl α-aminoacids using 4-tert-butoxycarbonyl-5,6-diphenylmorpholin-2-one: (r)-(N-tert-butoxycarbonyl)al-lylglycine," *Org. Synth.* 80:31-37 (2003).
Wolter et al., "Movement of Bax from the cytosol to mitochondria during apoptosis," *J. Cell Biol.* 139(5):1281-1292 (1997).
Yang et al., "Calculation of protein conformation from circular dichroism," *Methods Enzymol.* 130:208 (1986).
Youle et al., "The BCL-2 protein family: opposing activities that mediate cell death," *Nature Reviews Mol. Cell Biol.* 9:47-59 (2008).
International Preliminary Report on Patentability for PCT/US2014/029318, dated Sep. 15, 2015.
Written Opinion of the International Searching Authority for PCT/US2014/029318, dated Oct. 29, 2014.
International Search Report for PCT/US2014/029318 dated Oct. 29, 2014. 6 pages.
Labelle et al., "A stapled BIM peptide overcomes apoptotic resistance in hemotologic cancers," *"The Journal of Clinical Investigation"*, Jun. 1, 2012, vol. 122, No. 6, pp. 2018-2031.
Supplementary European Search Report for EP App. No. 14765369.5, dated Sep. 26, 2016 (6 pages).
Australia Examination Report No. 1 for AU App No. 2014228777, dated Nov. 27, 2017 (11 pages).
EPO Communication for EP Application No. 14765369.5, dated Feb. 13, 2018 (4 pages).

\* cited by examiner

```
                Helix 1
BCL-2   MAHAGRTGYDNRE VMK HYKLSQ GYEWDAGDVGAAPPGAAPAPGIFS   50   (SEQ ID NO: 72)
BCL-XL  ------MSQSNRE VVD SYKLSQ GYSWSQFSDVEENRTEAPEG------   40   (SEQ ID NO: 73)
BCL-W   MATP-ASAPDTRA VAD GYKIRQ GYVCGAGPGEGPAAD----------   40   (SEQ ID NO: 74)
```

```
                Helix 1        (SEQ ID NOs: 72, 138-142, and 155-157)
BCL-2    ----------------MAHAGRTGYDNREIVMKYIHYKLSQRGYEWDAGDVGAAPPGAAPAPGIFS     50
BCL-XL   ------------------------MSQSNRELVVDFLSYKLSQKGYSWSQFSDVEENRTEAPEGTESE  44
BCL-W    -----------------------MATPASAPDTRALVADFVGYKLRQKGYVCGAGPGEGPAADPLHQAMRAA  49
BCL-B    ------------------------MADPLRERTELILADYIGTCAREPGTPEPAPSTPEAAVLRSAAARLRQ 48
BFL-1/A1 ----------------MTDCEFGYIYRLAQDIIQCVLGIPQPGSGPSKTSRVLQNVAF   42
MCL-1    ELVGESGNNTSTDGSLPSTPPPAEEEEDELYRQSLEIISRYLREQATGAKPMGRSGATSRKALETLR  214
BOK      LRRSSVFAAEIMDAFDRSPTDKELVAQKALGREYVHARLLRAGSMSAPERAAPVPGRLAEVCAVL  70
BAX      ------MDGSGEQPRGGGPTSSEQIMKTGALLLQGFIQDRAGRMGGEAPELALDPVPQDAST  56
BAK      MASGQGPGPPRQECGEPALPSASEEQVAQDTEEVFRSYVFYRHQQEQEAEGVAAPADPEMVTLPLQP 67
```

Figure 1

(SEQ ID NOS: 4-71)

| Peptide | Sequence |
|---|---|
| *BCL-2* | |
| BH4 SAHB$_A$ | EIVBKYIHYKLSXRGYXWDA |
| BH4 SAHB$_B$ | EIVBKYIHXKLSXRGYEWDA |
| BH4 SAHB$_C$ | EIVBKYIXYKLXQRGYEWDA |
| BH4 SAHB$_D$ | EIVBKYXHYKXSQRGYEWDA |
| BH4 SAHB$_E$ | EIVBKYIHYKLSQRGYEWDA |
| BH4 SAHB$_{A4}$ | REIVBKYIHYKLSXRGYXWDA |
| BCL-2 BH4 WT | EIVBKYIHYKLSQRGYEWDA |
| BCL-2 BH4 WT$_{NR}$ | NREIVBKYIHYKLSQRGYEWDA |
| BH4 SAHB$_A$ Short | KYIHYKLSXRGYXWDA |
| BH4 SAHB$_B$ Short | KXIHYXLSQRGYEWDA |
| BH4 SAHB$_A$ E13A | AIVBKYIHYKLSXRGYXWDA |
| BH4 SAHB$_A$ I14A | EAVBKYIHYKLSXRGYXWDA |
| BH4 SAHB$_A$ V15A | EIABKYIHYKLSXRGYXWDA |
| BH4 SAHB$_A$ B16A | EIVAKYIHYKLSXRGYXWDA |
| BH4 SAHB$_A$ K17A | EIVBAYIHYKLSXRGYXWDA |
| BH4 SAHB$_A$ Y18A | EIVBKAIHYKLSXRGYXWDA |
| BH4 SAHB$_A$ I19A | EIVBKYAHYKLSXRGYXWDA |
| BH4 SAHB$_A$ H20A | EIVBKYIAYKLSXRGYXWDA |
| BH4 SAHB$_A$ Y21A | EIVBKYIHAKLSXRGYXWDA |
| BH4 SAHB$_A$ K22A | EIVBKYIHYALSXRGYXWDA |
| BH4 SAHB$_A$ L23A | EIVBKYIHYKASXRGYXWDA |
| BH4 SAHB$_A$ S24A | EIVBKYIHYKLAXRGYXWDA |
| BH4 SAHB$_A$ R26A | EIVBKYIHYKLSXAGYXWDA |
| BH4 SAHB$_A$ G27A | EIVBKYIHYKLSXRAYXWDA |
| BH4 SAHB$_A$ G27E | EIVBKYIHYKLSXREAXWDA |
| BH4 SAHB$_A$ Y28A | EIVBKYIHYKLSXRGAXWDA |
| BH4 SAHB$_A$ W30A | EIVBKYIHYKLSXRGYXADA |
| BH4 SAHB$_A$ D31A | EIVBKYIHYKLSXRGYXWAA |
| BH4 SAHB$_A$ A32E | EIVBKYIHYKLSXRGYXWDE |
| BH4 SAHB$_A$ Y18A Y21A | EIVBKAIHAKLSXRGYXWDA |
| BH4 SAHB$_A$ I19A L23A | EIVBKYAHYKASXRGYXWDA |
| BH4 SAHB$_A$ K17D | EIVBDYIHYKLSXRGYXWDA |
| BH4 SAHB$_A$ R26E | EIVBKYIHYKLSXEGYXWDA |
| BH4 SAHB$_A$ R12C | CEIVBKYIHYKLSXRGYXWDA |
| BH4 SAHB$_A$ G33C | EIVBKYIHYKLSXRGYXWDAC |
| BH4 SAHB$_A$ Short M16C | CKYIHYKLSXRGYXWDA |
| BH4 SAHB$_A$ Short G33C | KYIHYKLSXRGYXWDAC |
| BH4 pSAHB 19 | REIVBKYIXYKLXQRGYEUDAGD |
| BH4 pSAHB 20 | REIVUKYIHYKLSXRGYXWDAGD |
| BH4 pSAHB21 | REUVBKYIHYKLSXRGYXWDAGD |
| BH4 pSAHB 22 | REIVBKYIUYKLSXRGYXWDAGD |
| BH4 pSAHB 23 | REIVBKYUHYKLSXRGYXWDAGD |
| BH4 pSAHB 24 | REIVBKYIXYKLXQRGUEWDAGD |
| BH4 pSAHB 10 | REIVBKYIXYKLXQRGUEWDA |
| BH4 pSAHB 11 | REIVBKYIXYKLXQRGYEUDA |
| BH4 pSAHB 13 | REIVBKYIXYKLXQRGREUDA |
| BH4 pSAHB 14 | REIVBKYIXYKLXQRGUERDA |
| *BCL-XL* | |
| BCL-XL SAHB | RELVVDFLSYKLXRGYXWSQ |
| BCL-XL BH4 WT | RELVVDFLSYKLSQKGYSWSQ |
| BCL-XL SAHB L17A | RELVVDFASYKLXRGYXWSQ |
| BCL-XL SAHB D11K | RELVVKFLSYKLSXKGYXWSQ |
| BCL-XL SAHB D11K F22D | RELVVKFLSYKLXRGYXWDQ |
| BCL-XL pSAHB 1 | RELVKDFUSYKLSXKGYXWSQ |
| BCL-XL pSAHB 2 | RELVKDFLUYKLXRGYXWSQ |
| BCL-XL pSAHB 3 | REUVVDFLSYKLSXKGYXWSQ |
| BCL-XL pSAHB 4 | RELVUDFLSYKLXRGYXWSQ |
| BCL-XL pSAHB 5 | RELVVDFLSYKLXQKGUSWSQ |
| BCL-XL pSAHB 6 | RELVVDFLXYKLXQKGYSWUQ |
| *BCL-W* | |
| BCL-W SAHB | ALVADFVGYKLRXKGYXBGA |
| BCL-W SAHB$_C$ | RALVADFVGYKLRXKGYXBGA |
| BCL-W BH4 WT | ALVADFVGYKLRQKGYXBGA |
| BCL-W SAHB L22A | ALVADFVGYKARXKGYXBGA |
| BCL-W SAHB D15K | ALVAKFVGYKLRXKGYXBGA |
| BCL-W SAHB D16K G32D | ALVAKFVGYKLRXKGYXBGAD |
| BCL-W pSAHB 1 | RALVADFVUYKLRXKGYXBGA |
| BCL-W pSAHB 2 | RALVADFVUYKLRXKGYXBGA |
| BCL-W pSAHB 3 | RALVADFVGYKLRXKGYXBGA |
| BCL-W pSAHB 4 | RALVUDFVGYKLRXKGYXBGA |

Figure 2A

| Peptide | Sequence |
|---|---|
| BCL-2 | |
| 6x His BH4 SAHB$_A$ | HHHHHHEIVBKYIHYKLSXRGYXWDA |
| 6x His BH4 SAHB$_C$ | HHHHHHEIVBKYIXYKLXQRGYEWDA |
| 6x His BH4 SAHB$_A$ K17A | HHHHHHEIVBAYIHYKLSXRGYXWDA |
| 6x His BH4 SAHB$_A$ L23A | HHHHHHEIVBKYIHYKASXRGYXWDA |
| 6x His BH4 SAHB$_A$ I19A L23A | HHHHHHEIVBKYAHYKASXRGYXWDA |
| BH4 SAHB$_A$ I14C | ECVBKYIHYKLSXRGYXWDA |
| BH4 SAHB$_A$ K22C | EIVBKYIHYCLSXRGYXWDA |
| BH4 SAHB$_A$ Y28C | EIVBKYIHYKLSXRGCXWDA |
| BH4 SAHB$_{A1}$ Short | KYIHXKLSXRGYEWDA |

(SEQ ID NOs:158-166)

Figure 2B

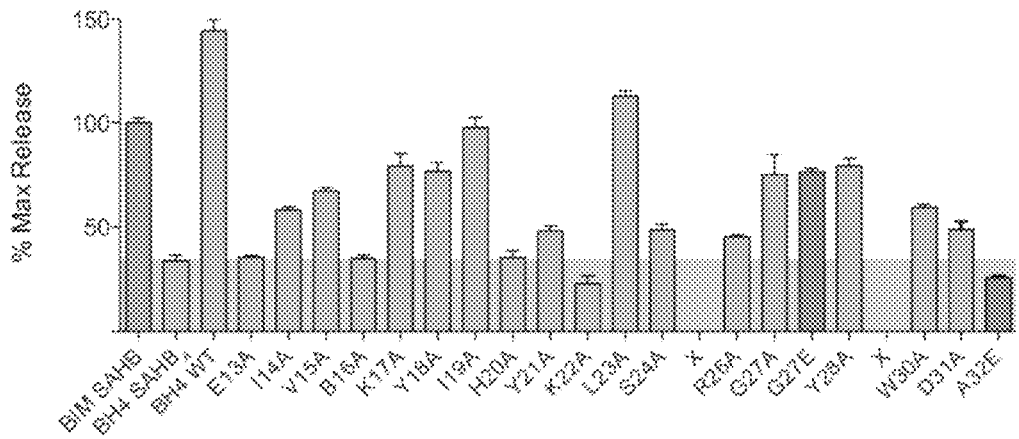
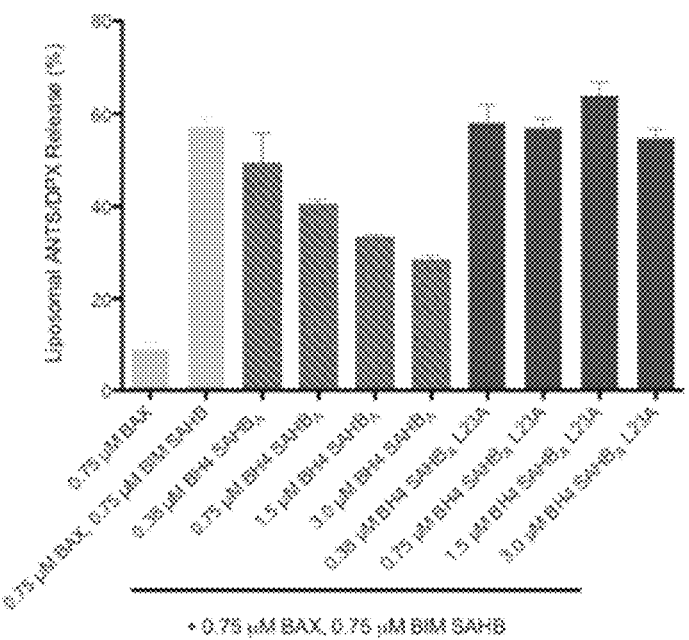
Figure 14

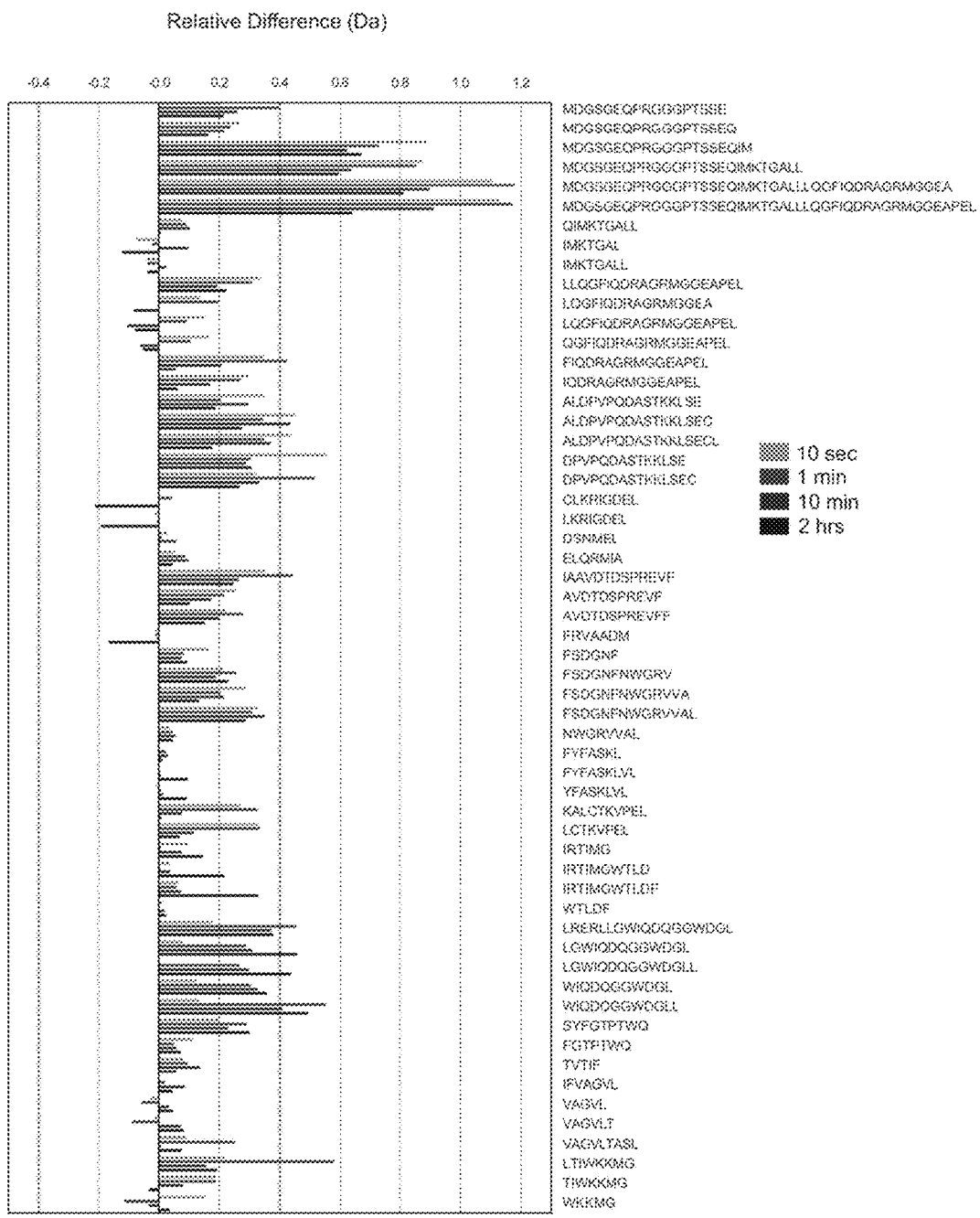
Figure 15A  (SEQ ID NOS: 75-131)

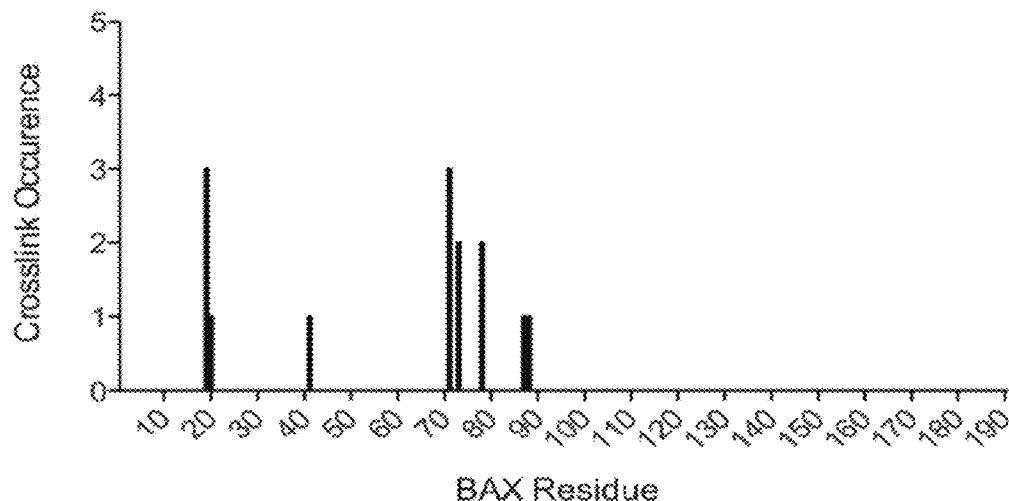
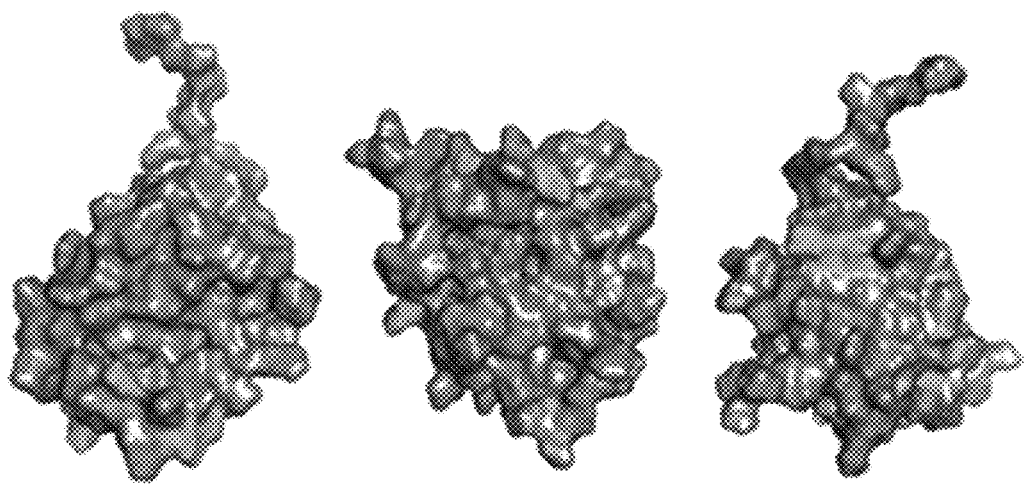
Figure 16

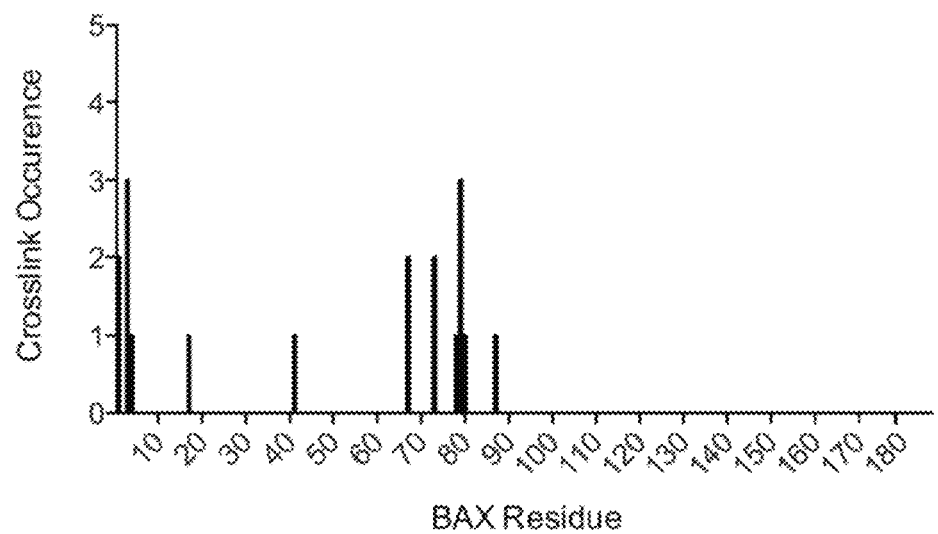
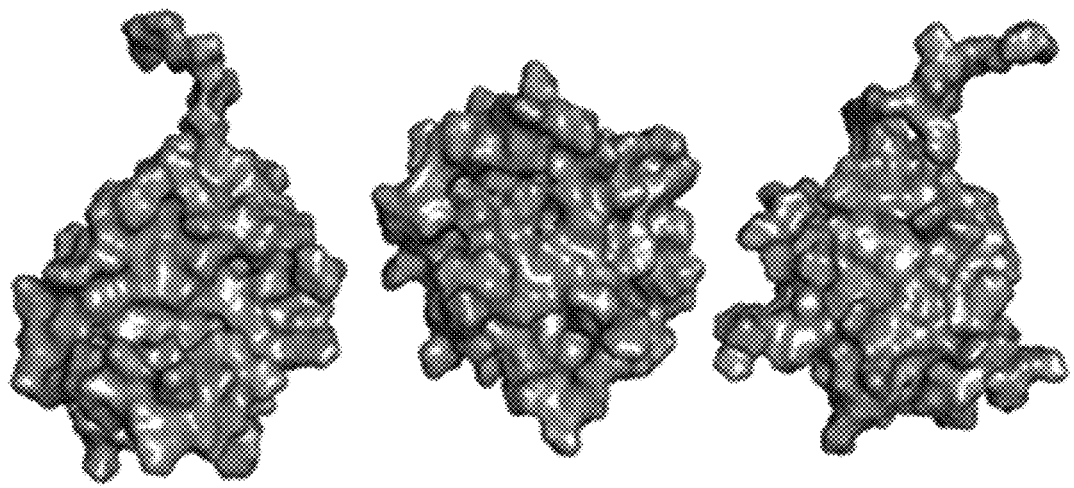
Figure 17

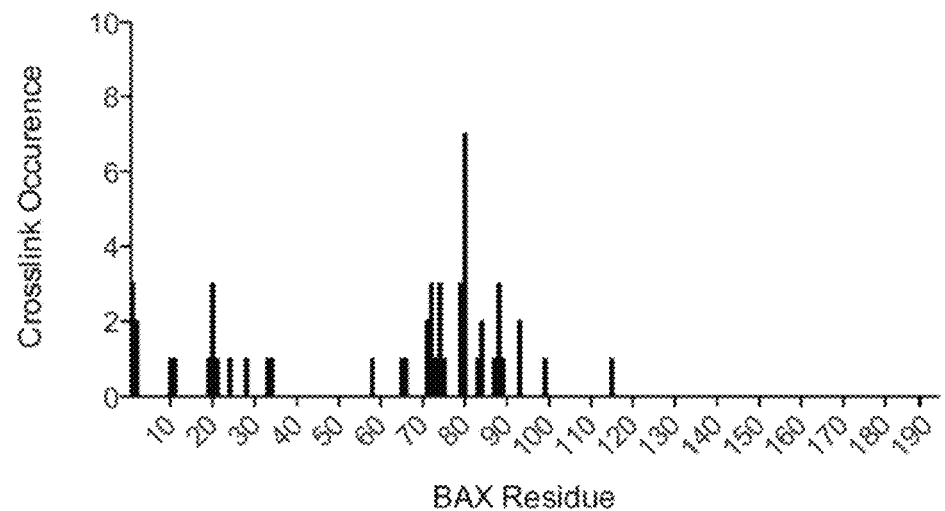
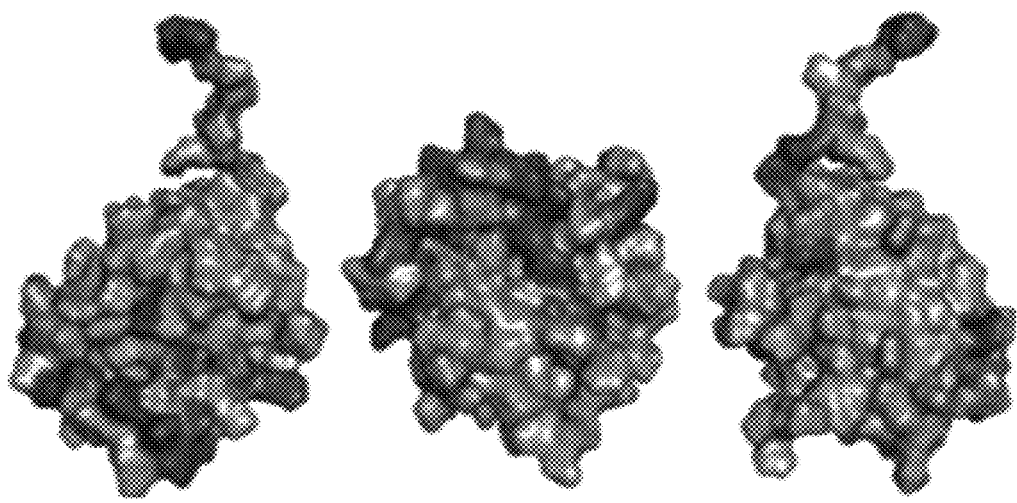
Figure 18

Figure 21: Table 1: Positions of Amino Acids with Internally Cross-Linkable or Cross-Linked Side Chains ○ is i+3; ✖ is i-3;
● is i-4; ○ is i+4;
▲ is i+7; ▼ is i-7

Figure 22: Table 2: Positions of Amino Acids with Internally Cross-Linkable or Cross-Linked Side Chains

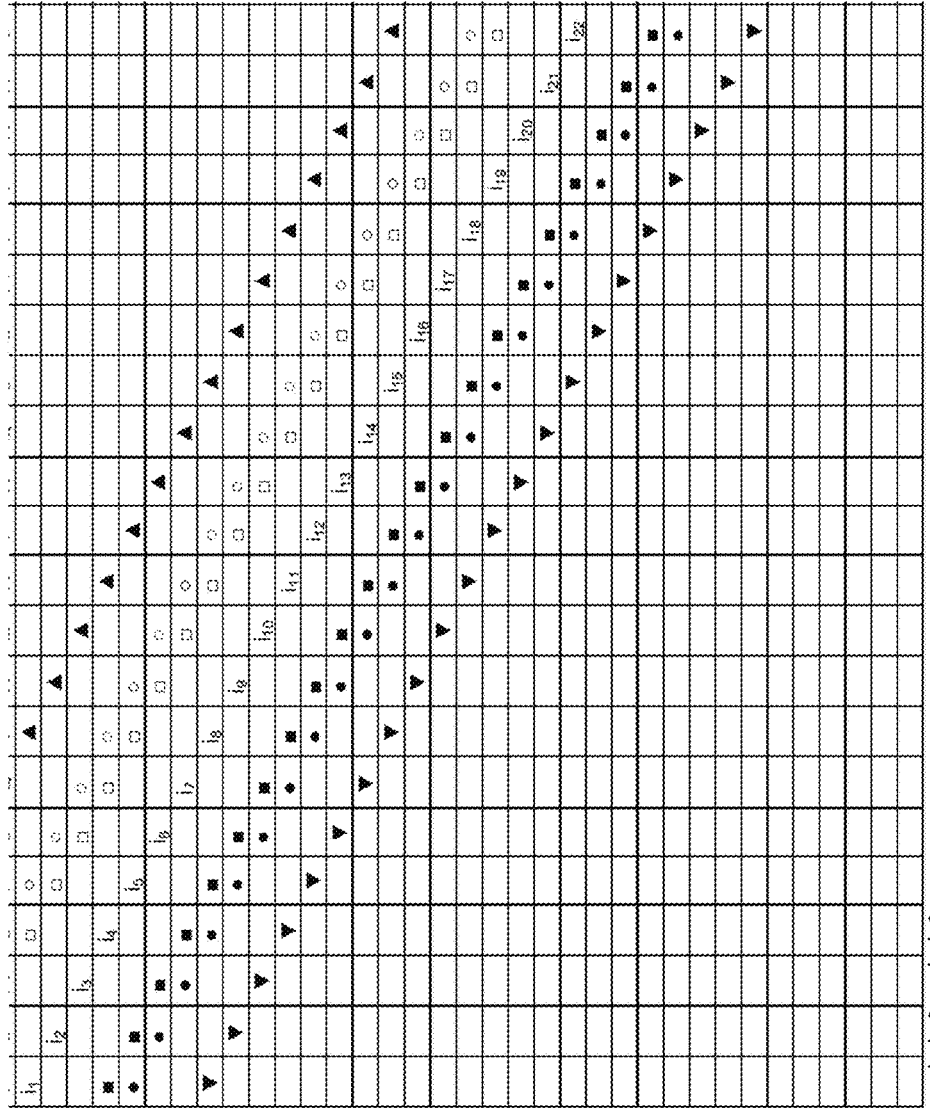
Figure 23: Table 3: Positions of Amino Acids with Internally Cross-Linkable or Cross-Linked Side Chains

SEQUENCE LISTING

```
<160> NUMBER OF SEQ ID NOS: 172

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Ile Val Met Lys Tyr Ile His Tyr Lys Leu Ser Gln Arg Gly Tyr
1               5                   10                  15

Glu Trp Asp Ala
            20
```

```
<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Glu Leu Val Val Asp Phe Leu Ser Tyr Lys Leu Ser Gln Lys Gly
1               5                   10                  15

Tyr Ser Trp Ser Gln Phe
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Val Ala Asp Phe Val Gly Tyr Lys Leu Arg Gln Lys Gly Tyr
1               5                   10                  15

Val Cys Gly Ala Gly
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 4

Glu Ile Val Xaa Lys Tyr Ile Arg Tyr Lys Leu Ser Xaa Arg Gly Tyr
1               5                   10                  15

Xaa Trp Asp Ala
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (9)..(9)
```

```
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation

<400> SEQUENCE: 5

Glu Ile Val Xaa Lys Tyr Ile His Xaa Lys Leu Ser Xaa Arg Gly Tyr
1               5                   10                  15

Glu Trp Asp Ala
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any uncross-linked or cross-linked amino acid
      in R-or S-orientation
<220> FEATURE:
<221> NAME/KEY: MOD_RES
<222> LOCATION: (12)..(12)
<223> OTHER INFORMATION: Any uncross-linked or cross-linked amino acid
      in R-or S-orientation

<400> SEQUENCE: 6

Glu Ile Val Xaa Lys Tyr Ile Xaa Tyr Lys Leu Xaa Gln Arg Gly Tyr
1               5                   10                  15

Glu Trp Asp Ala
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any uncross-linked or cross-linked amino acid
      in R-or S-orientation
<220> FEATURE:
<221> NAME/KEY: MOD_RES
<222> LOCATION: (11)..(11)
<223> OTHER INFORMATION: Any uncross-linked or cross-linked amino acid
      in R-or S-orientation

<400> SEQUENCE: 7

Glu Ile Val Xaa Lys Tyr Xaa His Tyr Lys Xaa Ser Gln Arg Gly Tyr
1               5                   10                  15

Glu Trp Asp Ala
            20
```

```
<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any uncross-linked or cross-linked amino acid
      in R-or S-orientation
<220> FEATURE:
<221> NAME/KEY: MOD_RES
<222> LOCATION: (10)..(10)
<223> OTHER INFORMATION: Any uncross-linked or cross-linked amino acid
      in R-or S-orientation

<400> SEQUENCE: 8

Glu Ile Val Xaa Lys Xaa Ile His Tyr Xaa Leu Ser Gln Arg Gly Tyr
1               5                   10                  15

Glu Trp Asp Ala
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 9

Arg Glu Ile Val Xaa Lys Tyr Ile His Tyr Lys Leu Ser Xaa Arg Gly
1               5                   10                  15

Tyr Xaa Trp Asp Ala
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 10

Glu Ile Val Xaa Lys Tyr Ile His Tyr Lys Leu Ser Gln Arg Gly Tyr
1               5                   10                  15
```

Glu Trp Asp Ala
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 11

Asn Arg Glu Ile Val Xaa Lys Tyr Ile His Tyr Lys Leu Ser Gln Arg
1               5                   10                  15

Gly Tyr Glu Trp Asp Ala
            20

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation

<400> SEQUENCE: 12

Lys Tyr Ile His Tyr Lys Leu Ser Xaa Arg Gly Tyr Xaa Trp Asp Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any uncross-linked or cross-linked amino acid
      in R-or S-orientation
<220> FEATURE:
<221> NAME/KEY: MOD_RES
<222> LOCATION: (6)..(6)
<223> OTHER INFORMATION: Any uncross-linked or cross-linked amino acid
      in R-or S-orientation

<400> SEQUENCE: 13

Lys Xaa Ile His Tyr Xaa Leu Ser Gln Arg Gly Tyr Glu Trp Asp Ala
1               5                   10                  15

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 14

Ala Ile Val Xaa Lys Tyr Ile His Tyr Lys Leu Ser Xaa Arg Gly Tyr
1               5                   10                  15

Xaa Trp Asp Ala
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 15

Glu Ala Val Xaa Lys Tyr Ile His Tyr Lys Leu Ser Xaa Arg Gly Tyr
1               5                   10                  15

Xaa Trp Asp Ala
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 16
```

```
Glu Ile Ala Xaa Lys Tyr Ile His Tyr Lys Leu Ser Xaa Arg Gly Tyr
1               5                   10                  15

Xaa Trp Asp Ala
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 17

Glu Ile Val Ala Lys Tyr Ile His Tyr Lys Leu Ser Xaa Arg Gly Tyr
1               5                   10                  15

Xaa Trp Asp Ala
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 18

Glu Ile Val Xaa Ala Tyr Ile His Tyr Lys Leu Ser Xaa Arg Gly Tyr
1               5                   10                  15

Xaa Trp Asp Ala
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
```

```
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 19

Glu Ile Val Xaa Lys Ala Ile His Tyr Lys Leu Ser Xaa Arg Gly Tyr
1               5                   10                  15

Xaa Trp Asp Ala
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 20

Glu Ile Val Xaa Lys Tyr Ala His Tyr Lys Leu Ser Xaa Arg Gly Tyr
1               5                   10                  15

Xaa Trp Asp Ala
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 21

Glu Ile Val Xaa Lys Tyr Ile Ala Tyr Lys Leu Ser Xaa Arg Gly Tyr
1               5                   10                  15

Xaa Trp Asp Ala
            20
```

```
<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 22

Glu Ile Val Xaa Lys Tyr Ile His Ala Lys Leu Ser Xaa Arg Gly Tyr
1               5                   10                  15

Xaa Trp Asp Ala
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 23

Glu Ile Val Xaa Lys Tyr Ile His Tyr Ala Leu Ser Xaa Arg Gly Tyr
1               5                   10                  15

Xaa Trp Asp Ala
            20

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
```

```
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 24

Glu Ile Val Xaa Lys Tyr Ile His Tyr Lys Ala Ser Xaa Arg Gly Tyr
1               5                   10                  15

Xaa Trp Asp Ala
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 25

Glu Ile Val Xaa Lys Tyr Ile His Tyr Lys Leu Ala Xaa Arg Gly Tyr
1               5                   10                  15

Xaa Trp Asp Ala
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 26

Glu Ile Val Xaa Lys Tyr Ile His Tyr Lys Leu Ser Xaa Ala Gly Tyr
1               5                   10                  15

Xaa Trp Asp Ala
            20

<210> SEQ ID NO 27
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 27

Glu Ile Val Xaa Lys Tyr Ile His Tyr Lys Leu Ser Xaa Arg Ala Tyr
1               5                   10                  15

Xaa Trp Asp Ala
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 28

Glu Ile Val Xaa Lys Tyr Ile His Tyr Lys Leu Ser Xaa Arg Glu Ala
1               5                   10                  15

Xaa Trp Asp Ala
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
```

<223> OTHER INFORMATION: Any uncross-linked or cross-linked amino acid
      in R-or S-orientation

<400> SEQUENCE: 29

Glu Ile Val Xaa Lys Tyr Ile His Tyr Lys Leu Ser Xaa Arg Gly Ala
1               5                   10                  15

Xaa Trp Asp Ala
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 30

Glu Ile Val Xaa Lys Tyr Ile His Tyr Lys Leu Ser Xaa Arg Gly Tyr
1               5                   10                  15

Xaa Ala Asp Ala
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 31

Glu Ile Val Xaa Lys Tyr Ile His Tyr Lys Leu Ser Xaa Arg Gly Tyr
1               5                   10                  15

Xaa Trp Ala Ala
            20

<210> SEQ ID NO 32
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 32

Glu Ile Val Xaa Lys Tyr Ile His Tyr Lys Leu Ser Xaa Arg Gly Tyr
1               5                   10                  15

Xaa Trp Asp Glu
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 33

Glu Ile Val Xaa Lys Ala Ile His Tyr Lys Leu Ser Xaa Arg Gly Tyr
1               5                   10                  15

Xaa Trp Asp Ala
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation
```

-continued

```
<400> SEQUENCE: 34

Glu Ile Val Xaa Lys Tyr Ala His Tyr Lys Ala Ser Xaa Arg Gly Tyr
1               5                   10                  15

Xaa Trp Asp Ala
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 35

Glu Ile Val Xaa Asp Tyr Ile His Tyr Lys Leu Ser Xaa Arg Gly Tyr
1               5                   10                  15

Xaa Trp Asp Ala
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 36

Glu Ile Val Xaa Lys Tyr Ile His Tyr Lys Leu Ser Xaa Glu Gly Tyr
1               5                   10                  15

Xaa Trp Asp Ala
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 37

Cys Glu Ile Val Xaa Lys Tyr Ile His Tyr Lys Leu Ser Xaa Arg Gly
1               5                   10                  15

Tyr Xaa Trp Asp Ala
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 38

Glu Ile Val Xaa Lys Tyr Ile His Tyr Lys Leu Ser Xaa Arg Gly Tyr
1               5                   10                  15

Xaa Trp Asp Ala Cys
            20

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any uncross-linked or cross-linked amino acid
      in R-or S-orientation
<220> FEATURE:
<221> NAME/KEY: MOD_RES
<222> LOCATION: (14)..(14)
<223> OTHER INFORMATION: Any uncross-linked or cross-linked amino acid
      in R-or S-orientation

<400> SEQUENCE: 39

Cys Lys Tyr Ile His Tyr Lys Leu Ser Xaa Arg Gly Tyr Xaa Trp Asp
1               5                   10                  15

Ala
```

```
<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation

<400> SEQUENCE: 40

Lys Tyr Ile His Tyr Lys Leu Ser Xaa Arg Gly Tyr Xaa Trp Asp Ala
1               5                   10                  15

Cys

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 41

Arg Glu Ile Val Xaa Lys Tyr Ile Xaa Tyr Lys Leu Xaa Gln Arg Gly
1               5                   10                  15

Tyr Glu Xaa Asp Ala Gly Asp
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
```

```
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 42

Arg Glu Ile Val Xaa Lys Tyr Ile His Tyr Lys Leu Ser Xaa Arg Gly
1               5                  10                  15

Tyr Xaa Trp Asp Ala Gly Asp
            20

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 43

Arg Glu Xaa Val Xaa Lys Tyr Ile His Tyr Lys Leu Ser Xaa Arg Gly
1               5                  10                  15

Tyr Xaa Trp Asp Ala Gly Asp
            20

<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 44

Arg Glu Ile Val Xaa Lys Tyr Ile Xaa Tyr Lys Leu Ser Xaa Arg Gly
1               5                  10                  15
```

Tyr Xaa Trp Asp Ala Gly Asp
          20

<210> SEQ ID NO 45
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 45

Arg Glu Ile Val Xaa Lys Tyr Xaa His Tyr Lys Leu Ser Xaa Arg Gly
1               5                   10                  15

Tyr Xaa Trp Asp Ala Gly Asp
          20

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any amino acid

<400> SEQUENCE: 46

Arg Glu Ile Val Xaa Lys Tyr Ile Xaa Tyr Lys Leu Xaa Gln Arg Gly
1               5                   10                  15

Xaa Glu Trp Asp Ala Gly Asp
          20

<210> SEQ ID NO 47
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any amino acid

<400> SEQUENCE: 47

Arg Glu Ile Val Xaa Lys Tyr Ile Xaa Tyr Lys Leu Xaa Gln Arg Gly
1               5                   10                  15

Xaa Glu Trp Asp Ala
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 48

Arg Glu Ile Val Xaa Lys Tyr Ile Xaa Tyr Lys Leu Xaa Gln Arg Gly
1               5                   10                  15

Tyr Glu Xaa Asp Ala
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
```

```
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 49

Arg Glu Ile Val Xaa Lys Tyr Ile Xaa Tyr Lys Leu Xaa Gln Arg Gly
1               5                   10                  15

Arg Glu Xaa Asp Ala
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any amino acid

<400> SEQUENCE: 50

Arg Glu Ile Val Xaa Lys Tyr Ile Xaa Tyr Lys Leu Xaa Gln Arg Gly
1               5                   10                  15

Xaa Glu Arg Asp Ala
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 51

Arg Glu Leu Val Val Asp Phe Leu Ser Tyr Lys Leu Ser Xaa Lys Gly
1               5                   10                  15
```

Tyr Xaa Trp Ser Gln
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Glu Leu Val Val Asp Phe Leu Ser Tyr Lys Leu Ser Gln Lys Gly
1               5                   10                  15

Tyr Ser Trp Ser Gln
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 53

Arg Glu Leu Val Val Asp Phe Ala Ser Tyr Lys Leu Ser Xaa Lys Gly
1               5                   10                  15

Tyr Xaa Trp Ser Gln
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 54

Arg Glu Leu Val Val Lys Phe Leu Ser Tyr Lys Leu Ser Xaa Lys Gly
1               5                   10                  15

Tyr Xaa Trp Ser Gln
            20

<210> SEQ ID NO 55
<211> LENGTH: 22
<212> TYPE: PRT

-continued

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 55

Arg Glu Leu Val Val Lys Phe Leu Ser Xaa Lys Leu Ser Gln Lys Gly
1               5                   10                  15

Tyr Xaa Trp Ser Gln Asp
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 56

Arg Glu Leu Val Lys Asp Phe Xaa Ser Tyr Lys Leu Ser Xaa Lys Gly
1               5                   10                  15

Tyr Xaa Trp Ser Gln
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 57

```
Arg Glu Leu Val Lys Asp Phe Leu Xaa Tyr Lys Leu Ser Xaa Lys Gly
1               5                   10                  15

Tyr Xaa Trp Ser Gln
            20
```

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 58

```
Arg Glu Xaa Val Val Asp Phe Leu Ser Tyr Lys Leu Ser Xaa Lys Gly
1               5                   10                  15

Tyr Xaa Trp Ser Gln
            20
```

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 59

```
Arg Glu Leu Val Xaa Asp Phe Leu Ser Tyr Lys Leu Ser Xaa Lys Gly
1               5                   10                  15

Tyr Xaa Trp Ser Gln
            20
```

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)

```
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any amino acid

<400> SEQUENCE: 60

Arg Glu Leu Val Val Asp Phe Leu Xaa Tyr Lys Leu Xaa Gln Lys Gly
1               5                   10                  15

Xaa Ser Trp Ser Gln
            20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (20)..(20)
<223> OTHER INFORMATION: Any amino acid

<400> SEQUENCE: 61

Arg Glu Leu Val Val Asp Phe Leu Xaa Tyr Lys Leu Xaa Gln Lys Gly
1               5                   10                  15

Tyr Ser Trp Xaa Gln
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any amino acid

<400> SEQUENCE: 62

Ala Leu Val Ala Asp Phe Val Gly Tyr Lys Leu Arg Xaa Lys Gly Tyr
1               5                   10                  15
```

Xaa Xaa Gly Ala
        20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 63

Arg Ala Leu Val Ala Asp Phe Val Gly Tyr Lys Leu Arg Xaa Lys Gly
1               5                   10                  15

Tyr Xaa Xaa Gly Ala
        20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Any amino acid

<400> SEQUENCE: 64

Ala Leu Val Ala Asp Phe Val Gly Tyr Lys Leu Arg Gln Lys Gly Tyr
1               5                   10                  15

Val Xaa Gly Ala
        20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any amino acid

<400> SEQUENCE: 65

```
Ala Leu Val Ala Asp Phe Val Gly Tyr Lys Ala Arg Xaa Lys Gly Tyr
1               5                   10                  15

Xaa Xaa Gly Ala
            20
```

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any amino acid

<400> SEQUENCE: 66

```
Ala Leu Val Ala Lys Phe Val Gly Tyr Lys Leu Arg Xaa Lys Gly Tyr
1               5                   10                  15

Xaa Xaa Gly Ala
            20
```

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any amino acid

<400> SEQUENCE: 67

```
Ala Leu Val Ala Lys Phe Val Gly Tyr Lys Leu Arg Xaa Lys Gly Tyr
1               5                   10                  15

Xaa Xaa Gly Ala Asp
            20
```

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 68

Arg Ala Leu Val Ala Asp Phe Xaa Gly Tyr Lys Leu Arg Xaa Lys Gly
1               5                   10                  15

Tyr Xaa Xaa Gly Ala
            20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 69

Arg Ala Leu Val Ala Asp Phe Val Xaa Tyr Lys Leu Arg Xaa Lys Gly
1               5                   10                  15

Tyr Xaa Xaa Gly Ala
            20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
```

```
<222> LOCATION: (18)..(18)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 70

Arg Ala Xaa Val Ala Asp Phe Val Gly Tyr Lys Leu Arg Xaa Lys Gly
1               5                   10                  15

Tyr Xaa Xaa Gly Ala
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 71

Arg Ala Leu Val Xaa Asp Phe Val Gly Tyr Lys Leu Arg Xaa Lys Gly
1               5                   10                  15

Tyr Xaa Xaa Gly Ala
            20

<210> SEQ ID NO 72
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser
    50

<210> SEQ ID NO 73
<211> LENGTH: 40
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 73

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly
        35                  40

<210> SEQ ID NO 74
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp
        35                  40

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Asp Gly Ser Gly Glu Gln Pro Arg Gly Gly Gly Pro Thr Ser Ser
1               5                   10                  15

Glu

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Asp Gly Ser Gly Glu Gln Pro Arg Gly Gly Gly Pro Thr Ser Ser
1               5                   10                  15

Glu Gln

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Asp Gly Ser Gly Glu Gln Pro Arg Gly Gly Gly Pro Thr Ser Ser
```

```
1               5                   10                  15
Glu Gln Ile Met
            20

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Asp Gly Ser Gly Glu Gln Pro Arg Gly Gly Gly Pro Thr Ser Ser
1               5                   10                  15

Glu Gln Ile Met Lys Thr Gly Ala Leu Leu
            20                  25

<210> SEQ ID NO 79
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala
        35                  40

<210> SEQ ID NO 80
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu
        35                  40                  45

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ile Met Lys Thr Gly Ala Leu Leu
1               5

<210> SEQ ID NO 82
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Met Lys Thr Gly Ala Leu
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Met Lys Thr Gly Ala Leu Leu
1               5

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Leu Gln Gly Phe Ile Gln Asp Arg Ala Gly Arg Met Gly Gly Glu
1               5                   10                  15

Ala Pro Glu Leu
            20

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Gln Gly Phe Ile Gln Asp Arg Ala Gly Arg Met Gly Gly Glu Ala
1               5                   10                  15

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Gln Gly Phe Ile Gln Asp Arg Ala Gly Arg Met Gly Gly Glu Ala
1               5                   10                  15

Pro Glu Leu

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 87

Gln Gly Phe Ile Gln Asp Arg Ala Gly Arg Met Gly Gly Glu Ala Pro
1               5                   10                  15

Glu Leu

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Ile Gln Asp Arg Ala Gly Arg Met Gly Gly Glu Ala Pro Glu Leu
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Gln Asp Arg Ala Gly Arg Met Gly Gly Glu Ala Pro Glu Leu
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Leu Asp Pro Val Pro Gln Asp Ala Ser Thr Lys Lys Leu Ser Glu
1               5                   10                  15

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Leu Asp Pro Val Pro Gln Asp Ala Ser Thr Lys Lys Leu Ser Glu
1               5                   10                  15

Cys

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Leu Asp Pro Val Pro Gln Asp Ala Ser Thr Lys Lys Leu Ser Glu

Cys Leu

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Pro Val Pro Gln Asp Ala Ser Thr Lys Lys Leu Ser Glu
1               5                   10

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Pro Val Pro Gln Asp Ala Ser Thr Lys Lys Leu Ser Glu Cys
1               5                   10                  15

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Leu Lys Arg Ile Gly Asp Glu Leu
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Lys Arg Ile Gly Asp Glu Leu
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Ser Asn Met Glu Leu
1               5

<210> SEQ ID NO 98
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 98

Glu Leu Gln Arg Met Ile Ala
1               5

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Ala Ala Val Asp Thr Asp Ser Pro Arg Glu Val Phe
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Val Asp Thr Asp Ser Pro Arg Glu Val Phe
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Val Asp Thr Asp Ser Pro Arg Glu Val Phe Phe
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Phe Arg Val Ala Ala Ala Asp Met
1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Phe Ser Asp Gly Asn Phe
1               5
```

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Phe Ser Asp Gly Asn Phe Asn Trp Gly Arg Val
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Ser Asp Gly Asn Phe Asn Trp Gly Arg Val Val Ala
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Ser Asp Gly Asn Phe Asn Trp Gly Arg Val Val Ala Leu
1               5                   10

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn Trp Gly Arg Val Val Ala Leu
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Phe Tyr Phe Ala Ser Lys Leu
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 109

Phe Tyr Phe Ala Ser Lys Leu Val Leu
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Tyr Phe Ala Ser Lys Leu Val Leu
1               5

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Ala Leu Cys Thr Lys Val Pro Glu Leu
1               5                   10

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Cys Thr Lys Val Pro Glu Leu
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Arg Thr Ile Met Gly
1               5

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Arg Thr Ile Met Gly Trp Thr Leu Asp
1               5                   10

<210> SEQ ID NO 115
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 115

Ile Arg Thr Ile Met Gly Trp Thr Leu Asp Phe
1               5                   10

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Trp Thr Leu Asp Phe
1               5

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Leu Arg Glu Arg Leu Leu Gly Trp Ile Gln Asp Gln Gly Gly Trp Asp
1               5                   10                  15

Gly Leu

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Gly Trp Ile Gln Asp Gln Gly Gly Trp Asp Gly Leu
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Leu Gly Trp Ile Gln Asp Gln Gly Gly Trp Asp Gly Leu Leu
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Trp Ile Gln Asp Gln Gly Gly Trp Asp Gly Leu
1               5                   10
```

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Trp Ile Gln Asp Gln Gly Gly Trp Asp Gly Leu Leu
1               5                   10
```

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Ser Tyr Phe Gly Thr Pro Thr Trp Gln
1               5
```

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Phe Gly Thr Pro Thr Trp Gln
1               5
```

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Thr Val Thr Ile Phe
1               5
```

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Ile Phe Val Ala Gly Val Leu
1               5
```

<210> SEQ ID NO 126
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 126

Val Ala Gly Val Leu
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Ala Gly Val Leu Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Val Ala Gly Val Leu Thr Ala Ser Leu
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Thr Ile Trp Lys Lys Met Gly
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Thr Ile Trp Lys Lys Met Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Trp Lys Lys Met Gly
1               5

-continued

```
<210> SEQ ID NO 132
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 132

Arg Glu Xaa Val Xaa Lys Tyr Ile His Tyr Lys Leu Ser Xaa Arg Gly
1               5                   10                  15

Tyr Xaa Trp Asp Ala Gly
            20

<210> SEQ ID NO 133
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (18)..(18)
<223> OTHER INFORMATION: Any uncross-linked or cross-linked amino acid
      in R-or S-orientation

<400> SEQUENCE: 133

Arg Glu Ile Val Xaa Lys Tyr Xaa His Tyr Lys Leu Ser Xaa Arg Gly
1               5                   10                  15

Tyr Xaa Trp Asp Ala Gly
            20

<210> SEQ ID NO 134
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any uncross-linked or cross-linked amino acid
      in R-or S-orientation
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any amino acid

<400> SEQUENCE: 134

Arg Glu Ile Val Xaa Lys Tyr Ile Xaa Tyr Lys Leu Xaa Gln Arg Gly
1               5                   10                  15

Tyr Glu Xaa Asp
            20

<210> SEQ ID NO 135
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, or a conservative amino acid substitution
      thereof, or any amino acid
<220> FEATURE:
<221> NAME/KEY: MOD_RES
<222> LOCATION: (2)..(2)
<223> OTHER INFORMATION: Arg or Cys, or a conservative amino acid
      substitution thereof, or any amino acid
<220> FEATURE:
<221> NAME/KEY: MOD_RES
<222> LOCATION: (3)..(3)
<223> OTHER INFORMATION: Glu or Ala, or a conservative amino acid
      substitution thereof, or any amino acid
<220> FEATURE:
<221> NAME/KEY: MOD_RES
<222> LOCATION: (4)..(4)
<223> OTHER INFORMATION: Ile, Ala, or Selenocysteine, or a conservative
      amino acid substitution thereof, or any amino acid
<220> FEATURE:
<221> NAME/KEY: MOD_RES
<222> LOCATION: (5)..(5)
<223> OTHER INFORMATION: Val or Ala, or a conservative amino acid
      substitution thereof, or any amino acid
<220> FEATURE:
<221> NAME/KEY: MOD_RES
<222> LOCATION: (6)..(6)
<223> OTHER INFORMATION: Met, Asp, Asn, Ala, Cys, or Selenocysteine, or
      a conservative amino acid substitution thereof, or any amino acid
<220> FEATURE:
<221> NAME/KEY: MOD_RES
<222> LOCATION: (7)..(7)
<223> OTHER INFORMATION: Lys, Ala, Asp, or a conservative amino acid
      substitution thereof, or any amino acid
<220> FEATURE:
<221> NAME/KEY: MOD_RES
<222> LOCATION: (8)..(8)
<223> OTHER INFORMATION: Tyr or Ala, or a conservative amino acid
      substitution thereof, or any amino acid
<220> FEATURE:
<221> NAME/KEY: MOD_RES
<222> LOCATION: (9)..(9)
<223> OTHER INFORMATION: Ile, Ala, or Selenocysteine, or a conservative
      amino acid substitution thereof, or any amino acid
<220> FEATURE:
```

```
<221> NAME/KEY: MOD_RES
<222> LOCATION: (10)..(10)
<223> OTHER INFORMATION: His, Ala, or Selenocysteine, or a conservative
      amino acid substitution thereof, or any amino acid
<220> FEATURE:
<221> NAME/KEY: MOD_RES
<222> LOCATION: (11)..(11)
<223> OTHER INFORMATION: Tyr or Ala, or a conservative amino acid
      substitution thereof, or any amino acid
<220> FEATURE:
<221> NAME/KEY: MOD_RES
<222> LOCATION: (12)..(12)
<223> OTHER INFORMATION: Lys or a conservative amino acid substitution
      thereof, or any amino acid
<220> FEATURE:
<221> NAME/KEY: MOD_RES
<222> LOCATION: (13)..(13)
<223> OTHER INFORMATION: Leu or Ala, or a conservative amino acid
      substitution thereof, or any amino acid
<220> FEATURE:
<221> NAME/KEY: MOD_RES
<222> LOCATION: (14)..(14)
<223> OTHER INFORMATION: Ser or Ala, or a conservative amino acid
      substitution thereof, or any amino acid
<220> FEATURE:
<221> NAME/KEY: MOD_RES
<222> LOCATION: (15)..(15)
<223> OTHER INFORMATION: Gln or a conservative amino acid substitution
      thereof, or any amino acid
<220> FEATURE:
<221> NAME/KEY: MOD_RES
<222> LOCATION: (16)..(16)
<223> OTHER INFORMATION: Arg, Ala, or Glu, or a conservative amino acid
      substitution thereof, or any amino acid
<220> FEATURE:
<221> NAME/KEY: MOD_RES
<222> LOCATION: (17)..(17)
<223> OTHER INFORMATION: Gly, Ala, or Glu, or a conservative amino acid
      substitution thereof, or any amino acid
<220> FEATURE:
<221> NAME/KEY: MOD_RES
<222> LOCATION: (18)..(18)
<223> OTHER INFORMATION: Tyr, Ala, Arg, or Selenocysteine, or a
      conservative amino acid substitution thereof, or any amino acid
<220> FEATURE:
<221> NAME/KEY: MOD_RES
<222> LOCATION: (19)..(19)
<223> OTHER INFORMATION: Glu or a conservative amino acid substitution
      thereof, or any amino acid
<220> FEATURE:
<221> NAME/KEY: MOD_RES
<222> LOCATION: (20)..(20)
<223> OTHER INFORMATION: Trp, Ala, Arg, or Selenocysteine, or a
      conservative amino acid substitution thereof, or any amino acid
<220> FEATURE:
<221> NAME/KEY: MOD_RES
<222> LOCATION: (21)..(21)
<223> OTHER INFORMATION: Asp or Ala, or a conservative amino acid
      substitution thereof, or any amino acid
<220> FEATURE:
<221> NAME/KEY: MOD_RES
<222> LOCATION: (22)..(22)
<223> OTHER INFORMATION: Ala or Glu, or a conservative amino acid
      substitution thereof, or any amino acid
<220> FEATURE:
<221> NAME/KEY: MOD_RES
<222> LOCATION: (23)..(23)
<223> OTHER INFORMATION: Gly or Cys, or a conservative amino acid
      substitution thereof, or any amino acid
<220> FEATURE:
<221> NAME/KEY: MOD_RES
<222> LOCATION: (24)..(24)
<223> OTHER INFORMATION: Asp or a conservative amino acid substitution
      thereof, or any amino acid
<220> FEATURE:
<223> OTHER INFORMATION: see specification as filed for detailed
      description of substitutions and preferred embodiments

<400> SEQUENCE: 135
```

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

```
<210> SEQ ID NO 136
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, or a conservative amino acid substitution
      thereof, or any amino acid
<220> FEATURE:
<221> NAME/KEY: MOD_RES
<222> LOCATION: (2)..(2)
<223> OTHER INFORMATION: Glu, or a conservative amino acid substitution
      thereof, or any amino acid
<220> FEATURE:
<221> NAME/KEY: MOD_RES
<222> LOCATION: (3)..(3)
<223> OTHER INFORMATION: Leu or Val, or a conservative amino acid
      substitution thereof, or any amino acid
<220> FEATURE:
<221> NAME/KEY: MOD_RES
<222> LOCATION: (4)..(4)
<223> OTHER INFORMATION: Val or a conservative amino acid substitution
      thereof, or any amino acid
<220> FEATURE:
<221> NAME/KEY: MOD_RES
<222> LOCATION: (5)..(5)
<223> OTHER INFORMATION: Val, Lys, or Selenocysteine, or a conservative
      amino acid substitution thereof, or any amino acid
<220> FEATURE:
<221> NAME/KEY: MOD_RES
<222> LOCATION: (6)..(6)
<223> OTHER INFORMATION: Asp or Lys, or a conservative amino acid
      substitution thereof, or any amino acid
<220> FEATURE:
<221> NAME/KEY: MOD_RES
<222> LOCATION: (7)..(7)
<223> OTHER INFORMATION: Phe or a conservative amino acid substitution
      thereof, or any amino acid
<220> FEATURE:
<221> NAME/KEY: MOD_RES
<222> LOCATION: (8)..(8)
<223> OTHER INFORMATION: Leu, Ala, or Selenocysteine, or a conservative
      amino acid substitution thereof, or any amino acid
<220> FEATURE:
<221> NAME/KEY: MOD_RES
<222> LOCATION: (9)..(9)
<223> OTHER INFORMATION: Ser or Selenocysteine, or a conservative amino
      acid substitution thereof, or any amino acid
<220> FEATURE:
<221> NAME/KEY: MOD_RES
<222> LOCATION: (10)..(10)
<223> OTHER INFORMATION: Tyr or a conservative amino acid substitution
      thereof, or any amino acid
<220> FEATURE:
<221> NAME/KEY: MOD_RES
<222> LOCATION: (11)..(11)
<223> OTHER INFORMATION: Lys or a conservative amino acid substitution
      thereof, or any amino acid
<220> FEATURE:
<221> NAME/KEY: MOD_RES
<222> LOCATION: (12)..(12)
<223> OTHER INFORMATION: Leu or a conservative amino acid substitution
      thereof, or any amino acid
<220> FEATURE:
<221> NAME/KEY: MOD_RES
<222> LOCATION: (13)..(13)
<223> OTHER INFORMATION: Ser or a conservative amino acid substitution
```

```
        thereof, or any amino acid
<220> FEATURE:
<221> NAME/KEY: MOD_RES
<222> LOCATION: (14)..(14)
<223> OTHER INFORMATION: Gln or a conservative amino acid substitution
        thereof, or any amino acid
<220> FEATURE:
<221> NAME/KEY: MOD_RES
<222> LOCATION: (15)..(15)
<223> OTHER INFORMATION: Lys or a conservative amino acid substitution
        thereof, or any amino acid
<220> FEATURE:
<221> NAME/KEY: MOD_RES
<222> LOCATION: (16)..(16)
<223> OTHER INFORMATION: Gly or a conservative amino acid substitution
        thereof, or any amino acid
<220> FEATURE:
<221> NAME/KEY: MOD_RES
<222> LOCATION: (17)..(17)
<223> OTHER INFORMATION: Tyr or Selenocysteine, or a conservative amino
        acid substitution thereof, or any amino acid
<220> FEATURE:
<221> NAME/KEY: MOD_RES
<222> LOCATION: (18)..(18)
<223> OTHER INFORMATION: Ser or a conservative amino acid substitution
        thereof, or any amino acid
<220> FEATURE:
<221> NAME/KEY: MOD_RES
<222> LOCATION: (19)..(19)
<223> OTHER INFORMATION: Trp or a conservative amino acid substitution
        thereof, or any amino acid
<220> FEATURE:
<221> NAME/KEY: MOD_RES
<222> LOCATION: (20)..(20)
<223> OTHER INFORMATION: Ser or Selenocysteine, or a conservative amino
        acid substitution thereof, or any amino acid
<220> FEATURE:
<221> NAME/KEY: MOD_RES
<222> LOCATION: (21)..(21)
<223> OTHER INFORMATION: Gln or a conservative amino acid substitution
        thereof, or any amino acid
<220> FEATURE:
<221> NAME/KEY: MOD_RES
<222> LOCATION: (22)..(22)
<223> OTHER INFORMATION: Phe or Asp, or a conservative amino acid
        substitution thereof, or any amino acid
<220> FEATURE:
<223> OTHER INFORMATION: see specification as filed for detailed
        description of substitutions and preferred embodiments

<400> SEQUENCE: 136

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 137
<211> LENGTH: 22
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Arg or a conservative amino acid substitution
        thereof
<220> FEATURE:
<221> NAME/KEY: MOD_RES
<222> LOCATION: (2)..(2)
<223> OTHER INFORMATION: Ala or a conservative amino acid substitution
        thereof
<220> FEATURE:
<221> NAME/KEY: MOD_RES
<222> LOCATION: (3)..(3)
```

-continued

```
<223> OTHER INFORMATION: Leu or Selenocysteine, or a conservative amino
      acid substitution thereof
<220> FEATURE:
<221> NAME/KEY: MOD_RES
<222> LOCATION: (4)..(4)
<223> OTHER INFORMATION: Cys or Val, or a conservative amino acid
      substitution thereof
<220> FEATURE:
<221> NAME/KEY: MOD_RES
<222> LOCATION: (5)..(5)
<223> OTHER INFORMATION: Ala or Selenocysteine, or a conservative amino
      acid substitution thereof
<220> FEATURE:
<221> NAME/KEY: MOD_RES
<222> LOCATION: (6)..(6)
<223> OTHER INFORMATION: Asp or Lys, or a conservative amino acid
      substitution thereof
<220> FEATURE:
<221> NAME/KEY: MOD_RES
<222> LOCATION: (7)..(7)
<223> OTHER INFORMATION: Phe or a conservative amino acid substitution
      thereof
<220> FEATURE:
<221> NAME/KEY: MOD_RES
<222> LOCATION: (8)..(8)
<223> OTHER INFORMATION: Val or Selenocysteine, or a conservative amino
      acid substitution thereof
<220> FEATURE:
<221> NAME/KEY: MOD_RES
<222> LOCATION: (9)..(9)
<223> OTHER INFORMATION: Gly or selenocystine, or a conservative amino
      acid substitution thereof
<220> FEATURE:
<221> NAME/KEY: MOD_RES
<222> LOCATION: (10)..(10)
<223> OTHER INFORMATION: Tyr or a conservative amino acid substitution
      thereof
<220> FEATURE:
<221> NAME/KEY: MOD_RES
<222> LOCATION: (11)..(11)
<223> OTHER INFORMATION: Lys or a conservative amino acid substitution
      thereof
<220> FEATURE:
<221> NAME/KEY: MOD_RES
<222> LOCATION: (12)..(12)
<223> OTHER INFORMATION: Leu or Ala, or a conservative amino acid
      substitution thereof
<220> FEATURE:
<221> NAME/KEY: MOD_RES
<222> LOCATION: (13)..(13)
<223> OTHER INFORMATION: Arg or a conservative amino acid substitution
      thereof
<220> FEATURE:
<221> NAME/KEY: MOD_RES
<222> LOCATION: (14)..(14)
<223> OTHER INFORMATION: Gln or a conservative amino acid substitution
      thereof
<220> FEATURE:
<221> NAME/KEY: MOD_RES
<222> LOCATION: (15)..(15)
<223> OTHER INFORMATION: Lys or a conservative amino acid substitution
      thereof
<220> FEATURE:
<221> NAME/KEY: MOD_RES
<222> LOCATION: (16)..(16)
<223> OTHER INFORMATION: Gly or a conservative amino acid substitution
      thereof
<220> FEATURE:
<221> NAME/KEY: MOD_RES
<222> LOCATION: (17)..(17)
<223> OTHER INFORMATION: Tyr or a conservative amino acid substitution
      thereof
<220> FEATURE:
<221> NAME/KEY: MOD_RES
<222> LOCATION: (18)..(18)
<223> OTHER INFORMATION: Val or a conservative amino acid substitution
      thereof
<220> FEATURE:
<221> NAME/KEY: MOD_RES
```

```
<222> LOCATION: (19)..(19)
<223> OTHER INFORMATION: Cys, Asp, or Asn, or a conservative amino acid
      substitution thereof
<220> FEATURE:
<221> NAME/KEY: MOD_RES
<222> LOCATION: (20)..(20)
<223> OTHER INFORMATION: Gly or a conservative amino acid substitution
      thereof
<220> FEATURE:
<221> NAME/KEY: MOD_RES
<222> LOCATION: (21)..(21)
<223> OTHER INFORMATION: Ala or a conservative amino acid substitution
      thereof
<220> FEATURE:
<221> NAME/KEY: MOD_RES
<222> LOCATION: (22)..(22)
<223> OTHER INFORMATION: Gly or Asp, or a conservative amino acid
      substitution thereof

<400> SEQUENCE: 137

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 138
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu
        35                  40

<210> SEQ ID NO 139
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala

<210> SEQ ID NO 140
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

```
Met Ala Asp Pro Leu Arg Glu Arg Thr Glu Leu Leu Ala Asp Tyr
1               5                   10                  15

Leu Gly Tyr Cys Ala Arg Glu Pro Gly Thr Pro Glu Pro Ala Pro Ser
                20                  25                  30

Thr Pro Glu Ala Ala Val Leu Arg Ser Ala Ala Arg Leu Arg Gln
        35                  40                  45

<210> SEQ ID NO 141
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
                20                  25                  30

Thr Ser Arg Val Leu Gln Asn Val Ala Phe
            35                  40

<210> SEQ ID NO 142
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Leu Val Gly Glu Ser Gly Asn Asn Thr Ser Thr Asp Gly Ser Leu
1               5                   10                  15

Pro Ser Thr Pro Pro Ala Glu Glu Glu Asp Glu Leu Tyr Arg
                20                  25                  30

Gln Ser Leu Glu Ile Ile Ser Arg Tyr Leu Arg Glu Gln Ala Thr Gly
            35                  40                  45

Ala Lys Pro Met Gly Arg Ser Gly Ala Thr Ser Arg Lys Ala Leu Glu
        50                  55                  60

Thr Leu Arg
65

<210> SEQ ID NO 143
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr, or a conservative amino acid substitution
      thereof, or any amino acid
<220> FEATURE:
<221> NAME/KEY: MOD_RES
<222> LOCATION: (2)..(2)
<223> OTHER INFORMATION: Asp, or a conservative amino acid substitution
      thereof, or any amino acid
<220> FEATURE:
<221> NAME/KEY: MOD_RES
<222> LOCATION: (3)..(3)
<223> OTHER INFORMATION: Cys, or a conservative amino acid substitution
      thereof, or any amino acid
```

```
-continued

<220> FEATURE:
<221> NAME/KEY: MOD_RES
<222> LOCATION: (4)..(4)
<223> OTHER INFORMATION: Glu, or a conservative amino acid substitution
      thereof, or any amino acid,
<220> FEATURE:
<221> NAME/KEY: MOD_RES
<222> LOCATION: (5)..(5)
<223> OTHER INFORMATION: Phe, or a conservative amino acid substitution
      thereof, or any amino acid
<220> FEATURE:
<221> NAME/KEY: MOD_RES
<222> LOCATION: (6)..(6)
<223> OTHER INFORMATION: Gly, or a conservative amino acid substitution
      thereof, or any amino acid
<220> FEATURE:
<221> NAME/KEY: MOD_RES
<222> LOCATION: (7)..(7)
<223> OTHER INFORMATION: Tyr, or a conservative amino acid substitution
      thereof, or any amino acid
<220> FEATURE:
<221> NAME/KEY: MOD_RES
<222> LOCATION: (8)..(8)
<223> OTHER INFORMATION: Ile, or a conservative amino acid substitution
      thereof, or any amino acid
<220> FEATURE:
<221> NAME/KEY: MOD_RES
<222> LOCATION: (9)..(9)
<223> OTHER INFORMATION: Tyr, or a conservative amino acid substitution
      thereof, or any amino acid
<220> FEATURE:
<221> NAME/KEY: MOD_RES
<222> LOCATION: (10)..(10)
<223> OTHER INFORMATION: Arg, or a conservative amino acid substitution
      thereof, or any amino acid
<220> FEATURE:
<221> NAME/KEY: MOD_RES
<222> LOCATION: (11)..(11)
<223> OTHER INFORMATION: Leu, or a conservative amino acid substitution
      thereof, or any amino acid
<220> FEATURE:
<221> NAME/KEY: MOD_RES
<222> LOCATION: (12)..(12)
<223> OTHER INFORMATION: Ala, or a conservative amino acid substitution
      thereof, or any amino acid
<220> FEATURE:
<221> NAME/KEY: MOD_RES
<222> LOCATION: (13)..(13)
<223> OTHER INFORMATION: Gln, or a conservative amino acid substitution
      thereof, or any amino acid
<220> FEATURE:
<221> NAME/KEY: MOD_RES
<222> LOCATION: (14)..(14)
<223> OTHER INFORMATION: Asp, or a conservative amino acid substitution
      thereof, or any amino acid
<220> FEATURE:
<221> NAME/KEY: MOD_RES
<222> LOCATION: (15)..(15)
<223> OTHER INFORMATION: Tyr, or a conservative amino acid substitution
      thereof, or any amino acid
<220> FEATURE:
<221> NAME/KEY: MOD_RES
<222> LOCATION: (16)..(16)
<223> OTHER INFORMATION: Leu, or a conservative amino acid substitution
      thereof, or any amino acid
<220> FEATURE:
<221> NAME/KEY: MOD_RES
<222> LOCATION: (17)..(17)
<223> OTHER INFORMATION: Gln, or a conservative amino acid substitution
      thereof, or any amino acid
<220> FEATURE:
<221> NAME/KEY: MOD_RES
<222> LOCATION: (18)..(18)
<223> OTHER INFORMATION: Cys, or a conservative amino acid substitution
      thereof, or any amino acid
<220> FEATURE:
<221> NAME/KEY: MOD_RES
<222> LOCATION: (19)..(19)
<223> OTHER INFORMATION: Val, or a conservative amino acid substitution
``` thereof, or any amino acid
<220> FEATURE:
<221> NAME/KEY: MOD_RES
<222> LOCATION: (20)..(20)
<223> OTHER INFORMATION: Leu, or a conservative amino acid substitution
        thereof, or any amino acid
<220> FEATURE:
<221> NAME/KEY: MOD_RES
<222> LOCATION: (21)..(21)
<223> OTHER INFORMATION: Gln, or a conservative amino acid substitution
        thereof, or any amino acid
<220> FEATURE:
<221> NAME/KEY: MOD_RES
<222> LOCATION: (22)..(22)
<223> OTHER INFORMATION: Ile, or a conservative amino acid substitution
        thereof, or any amino acid
<220> FEATURE:
<221> NAME/KEY: MOD_RES
<222> LOCATION: (23)..(23)
<223> OTHER INFORMATION: Pro, or a conservative amino acid substitution
        thereof, or any amino acid
<220> FEATURE:
<221> NAME/KEY: MOD_RES
<222> LOCATION: (24)..(24)
<223> OTHER INFORMATION: Gln, or a conservative amino acid substitution
        thereof, or any amino acid
<220> FEATURE:
<221> NAME/KEY: MOD_RES
<222> LOCATION: (25)..(25)
<223> OTHER INFORMATION: Pro, or a conservative amino acid substitution
        thereof, or any amino acid
<220> FEATURE:
<221> NAME/KEY: MOD_RES
<222> LOCATION: (26)..(26)
<223> OTHER INFORMATION: Gly, or a conservative amino acid substitution
        thereof, or any amino acid
<220> FEATURE:
<221> NAME/KEY: MOD_RES
<222> LOCATION: (27)..(27)
<223> OTHER INFORMATION: Ser, or a conservative amino acid substitution
        thereof, or any amino acid
<220> FEATURE:
<223> OTHER INFORMATION: see specification as filed for detailed
        description of substitutions and preferred embodiments

<400> SEQUENCE: 143

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 144
<211> LENGTH: 27
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 144

Thr Asp Cys Glu Phe Gly Tyr Ile Tyr Arg Leu Ala Gln Asp Tyr Leu
1               5                   10                  15

Gln Cys Val Leu Gln Ile Pro Gln Pro Gly Ser
            20                  25

<210> SEQ ID NO 145
<211> LENGTH: 27
<212> TYPE: PRT
<213> ORGANISM: Artificial Sequence
<220> FEATURE:
<223> OTHER INFORMATION: Description of Artificial Sequence: Synthetic
        peptide
<220> FEATURE:

```
<221> NAME/KEY: MOD_RES
<222> LOCATION: (1)..(1)
<223> OTHER INFORMATION: Glu, or a conservative amino acid substitution
      thereof, or any amino acid
<220> FEATURE:
<221> NAME/KEY: MOD_RES
<222> LOCATION: (2)..(2)
<223> OTHER INFORMATION: Asp, or a conservative amino acid substitution
      thereof, or any amino acid
<220> FEATURE:
<221> NAME/KEY: MOD_RES
<222> LOCATION: (3)..(3)
<223> OTHER INFORMATION: Glu, or a conservative amino acid substitution
      thereof, or any amino acid
<220> FEATURE:
<221> NAME/KEY: MOD_RES
<222> LOCATION: (4)..(4)
<223> OTHER INFORMATION: Leu, or a conservative amino acid substitution
      thereof, or any amino acid,
<220> FEATURE:
<221> NAME/KEY: MOD_RES
<222> LOCATION: (5)..(5)
<223> OTHER INFORMATION: Tyr, or a conservative amino acid substitution
      thereof, or any amino acid
<220> FEATURE:
<221> NAME/KEY: MOD_RES
<222> LOCATION: (6)..(6)
<223> OTHER INFORMATION: Arg, or a conservative amino acid substitution
      thereof, or any amino acid
<220> FEATURE:
<221> NAME/KEY: MOD_RES
<222> LOCATION: (7)..(7)
<223> OTHER INFORMATION: Gln, or a conservative amino acid substitution
      thereof, or any amino acid
<220> FEATURE:
<221> NAME/KEY: MOD_RES
<222> LOCATION: (8)..(8)
<223> OTHER INFORMATION: Ser, or a conservative amino acid substitution
      thereof, or any amino acid
<220> FEATURE:
<221> NAME/KEY: MOD_RES
<222> LOCATION: (9)..(9)
<223> OTHER INFORMATION: Leu, or a conservative amino acid substitution
      thereof, or any amino acid
<220> FEATURE:
<221> NAME/KEY: MOD_RES
<222> LOCATION: (10)..(10)
<223> OTHER INFORMATION: Glu, or a conservative amino acid substitution
      thereof, or any amino acid
<220> FEATURE:
<221> NAME/KEY: MOD_RES
<222> LOCATION: (11)..(11)
<223> OTHER INFORMATION: Ile, or a conservative amino acid substitution
      thereof, or any amino acid
<220> FEATURE:
<221> NAME/KEY: MOD_RES
<222> LOCATION: (12)..(12)
<223> OTHER INFORMATION: Ile, or a conservative amino acid substitution
      thereof, or any amino acid
<220> FEATURE:
<221> NAME/KEY: MOD_RES
<222> LOCATION: (13)..(13)
<223> OTHER INFORMATION: Ser, or a conservative amino acid substitution
      thereof, or any amino acid
<220> FEATURE:
<221> NAME/KEY: MOD_RES
<222> LOCATION: (14)..(14)
<223> OTHER INFORMATION: Arg, or a conservative amino acid substitution
      thereof, or any amino acid
<220> FEATURE:
<221> NAME/KEY: MOD_RES
<222> LOCATION: (15)..(15)
<223> OTHER INFORMATION: Tyr, or a conservative amino acid substitution
      thereof, or any amino acid
<220> FEATURE:
<221> NAME/KEY: MOD_RES
<222> LOCATION: (16)..(16)
<223> OTHER INFORMATION: Leu, or a conservative amino acid substitution
      thereof, or any amino acid
```

```
<220> FEATURE:
<221> NAME/KEY: MOD_RES
<222> LOCATION: (17)..(17)
<223> OTHER INFORMATION: Arg, or a conservative amino acid substitution
      thereof, or any amino acid
<220> FEATURE:
<221> NAME/KEY: MOD_RES
<222> LOCATION: (18)..(18)
<223> OTHER INFORMATION: Glu, or a conservative amino acid substitution
      thereof, or any amino acid
<220> FEATURE:
<221> NAME/KEY: MOD_RES
<222> LOCATION: (19)..(19)
<223> OTHER INFORMATION: Gln, or a conservative amino acid substitution
      thereof, or any amino acid
<220> FEATURE:
<221> NAME/KEY: MOD_RES
<222> LOCATION: (20)..(20)
<223> OTHER INFORMATION: Ala, or a conservative amino acid substitution
      thereof, or any amino acid
<220> FEATURE:
<221> NAME/KEY: MOD_RES
<222> LOCATION: (21)..(21)
<223> OTHER INFORMATION: Thr, or a conservative amino acid substitution
      thereof, or any amino acid
<220> FEATURE:
<221> NAME/KEY: MOD_RES
<222> LOCATION: (22)..(22)
<223> OTHER INFORMATION: Gly, or a conservative amino acid substitution
      thereof, or any amino acid
<220> FEATURE:
<221> NAME/KEY: MOD_RES
<222> LOCATION: (23)..(23)
<223> OTHER INFORMATION: Ala, or a conservative amino acid substitution
      thereof, or any amino acid
<220> FEATURE:
<221> NAME/KEY: MOD_RES
<222> LOCATION: (24)..(24)
<223> OTHER INFORMATION: Lys, or a conservative amino acid substitution
      thereof, or any amino acid
<220> FEATURE:
<221> NAME/KEY: MOD_RES
<222> LOCATION: (25)..(25)
<223> OTHER INFORMATION: Pro, or a conservative amino acid substitution
      thereof, or any amino acid
<220> FEATURE:
<221> NAME/KEY: MOD_RES
<222> LOCATION: (26)..(26)
<223> OTHER INFORMATION: Met, or a conservative amino acid substitution
      thereof, or any amino acid,
<220> FEATURE:
<221> NAME/KEY: MOD_RES
<222> LOCATION: (27)..(27)
<223> OTHER INFORMATION: Gly, or a conservative amino acid substitution
      thereof, or any amino acid;
<220> FEATURE:
<223> OTHER INFORMATION: see specification as filed for detailed
      description of substitutions and preferred embodiments

<400> SEQUENCE: 145

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 146
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Glu Asp Glu Leu Tyr Arg Gln Ser Leu Glu Ile Ile Ser Arg Tyr Leu
```

-continued

```
1               5                   10                  15

Arg Glu Gln Ala Thr Gly Ala Lys Pro Met Gly
            20                  25

<210> SEQ ID NO 147
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, or a conservative amino acid substitution
      thereof, or any amino acid
<220> FEATURE:
<221> NAME/KEY: MOD_RES
<222> LOCATION: (2)..(2)
<223> OTHER INFORMATION: Val, or a conservative amino acid substitution
      thereof, or any amino acid
<220> FEATURE:
<221> NAME/KEY: MOD_RES
<222> LOCATION: (3)..(3)
<223> OTHER INFORMATION: Ala, or a conservative amino acid substitution
      thereof, or any amino acid
<220> FEATURE:
<221> NAME/KEY: MOD_RES
<222> LOCATION: (4)..(4)
<223> OTHER INFORMATION: Gln, or a conservative amino acid substitution
      thereof, or any amino acid
<220> FEATURE:
<221> NAME/KEY: MOD_RES
<222> LOCATION: (5)..(5)
<223> OTHER INFORMATION: Ala, or a conservative amino acid substitution
      thereof, or any amino acid
<220> FEATURE:
<221> NAME/KEY: MOD_RES
<222> LOCATION: (6)..(6)
<223> OTHER INFORMATION: Lys, or a conservative amino acid substitution
      thereof, or any amino acid
<220> FEATURE:
<221> NAME/KEY: MOD_RES
<222> LOCATION: (7)..(7)
<223> OTHER INFORMATION: Ala, or a conservative amino acid substitution
      thereof, or any amino acid,
<220> FEATURE:
<221> NAME/KEY: MOD_RES
<222> LOCATION: (8)..(8)
<223> OTHER INFORMATION: Leu, or a conservative amino acid substitution
      thereof, or any amino acid
<220> FEATURE:
<221> NAME/KEY: MOD_RES
<222> LOCATION: (9)..(9)
<223> OTHER INFORMATION: Gly, or a conservative amino acid substitution
      thereof, or any amino acid
<220> FEATURE:
<221> NAME/KEY: MOD_RES
<222> LOCATION: (10)..(10)
<223> OTHER INFORMATION: Arg, or a conservative amino acid substitution
      thereof, or any amino acid
<220> FEATURE:
<221> NAME/KEY: MOD_RES
<222> LOCATION: (11)..(11)
<223> OTHER INFORMATION: Glu or a conservative amino acid substitution
      thereof, or any amino acid
<220> FEATURE:
<221> NAME/KEY: MOD_RES
<222> LOCATION: (12)..(12)
<223> OTHER INFORMATION: Tyr, or a conservative amino acid substitution
      thereof, or any amino acid
<220> FEATURE:
<221> NAME/KEY: MOD_RES
<222> LOCATION: (13)..(13)
<223> OTHER INFORMATION: Val, or a conservative amino acid substitution
      thereof, or any amino acid
<220> FEATURE:
```

```
<221> NAME/KEY: MOD_RES
<222> LOCATION: (14)..(14)
<223> OTHER INFORMATION: His, or a conservative amino acid substitution
      thereof, or any amino acid
<220> FEATURE:
<221> NAME/KEY: MOD_RES
<222> LOCATION: (15)..(15)
<223> OTHER INFORMATION: Ala, or a conservative amino acid substitution
      thereof, or any amino acid
<220> FEATURE:
<221> NAME/KEY: MOD_RES
<222> LOCATION: (16)..(16)
<223> OTHER INFORMATION: Arg, or a conservative amino acid substitution
      thereof, or any amino acid
<220> FEATURE:
<221> NAME/KEY: MOD_RES
<222> LOCATION: (17)..(17)
<223> OTHER INFORMATION: Leu, or a conservative amino acid substitution
      thereof, or any amino acid
<220> FEATURE:
<221> NAME/KEY: MOD_RES
<222> LOCATION: (18)..(18)
<223> OTHER INFORMATION: Leu, or a conservative amino acid substitution
      thereof, or any amino acid
<220> FEATURE:
<221> NAME/KEY: MOD_RES
<222> LOCATION: (19)..(19)
<223> OTHER INFORMATION: Arg, or a conservative amino acid substitution
      thereof, or any amino acid
<220> FEATURE:
<221> NAME/KEY: MOD_RES
<222> LOCATION: (20)..(20)
<223> OTHER INFORMATION: Ala, or a conservative amino acid substitution
      thereof, or any amino acid
<220> FEATURE:
<221> NAME/KEY: MOD_RES
<222> LOCATION: (21)..(21)
<223> OTHER INFORMATION: Gly, or a conservative amino acid substitution
      thereof, or any amino acid
<220> FEATURE:
<221> NAME/KEY: MOD_RES
<222> LOCATION: (22)..(22)
<223> OTHER INFORMATION: Leu, or a conservative amino acid substitution
      thereof, or any amino acid
<220> FEATURE:
<221> NAME/KEY: MOD_RES
<222> LOCATION: (23)..(23)
<223> OTHER INFORMATION: Ser, or a conservative amino acid substitution
      thereof, or any amino acid
<220> FEATURE:
<221> NAME/KEY: MOD_RES
<222> LOCATION: (24)..(24)
<223> OTHER INFORMATION: Trp, or a conservative amino acid substitution
      thereof, or any amino acid
<220> FEATURE:
<221> NAME/KEY: MOD_RES
<222> LOCATION: (25)..(25)
<223> OTHER INFORMATION: Ser, or a conservative amino acid substitution
      thereof, or any amino acid,
<220> FEATURE:
<221> NAME/KEY: MOD_RES
<222> LOCATION: (26)..(26)
<223> OTHER INFORMATION: Ala, or a conservative amino acid substitution
      thereof, or any amino acid;
<220> FEATURE:
<223> OTHER INFORMATION: see specification as filed for detailed
      description of substitutions and preferred embodiments

<400> SEQUENCE: 147

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 148
<211> LENGTH: 26
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Leu Val Ala Gln Ala Lys Ala Leu Gly Arg Glu Tyr Val His Ala Arg
1               5                   10                  15

Leu Leu Arg Ala Gly Leu Ser Trp Ser Ala
            20                  25

<210> SEQ ID NO 149
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, or a conservative amino acid substitution
      thereof, or any amino acid
<220> FEATURE:
<221> NAME/KEY: MOD_RES
<222> LOCATION: (2)..(2)
<223> OTHER INFORMATION: Glu, or a conservative amino acid substitution
      thereof, or any amino acid
<220> FEATURE:
<221> NAME/KEY: MOD_RES
<222> LOCATION: (3)..(3)
<223> OTHER INFORMATION: Gln, or a conservative amino acid substitution
      thereof, or any amino acid
<220> FEATURE:
<221> NAME/KEY: MOD_RES
<222> LOCATION: (4)..(4)
<223> OTHER INFORMATION: Ile, or a conservative amino acid substitution
      thereof, or any amino acid,
<220> FEATURE:
<221> NAME/KEY: MOD_RES
<222> LOCATION: (5)..(5)
<223> OTHER INFORMATION: Met, or a conservative amino acid substitution
      thereof, or any amino acid
<220> FEATURE:
<221> NAME/KEY: MOD_RES
<222> LOCATION: (6)..(6)
<223> OTHER INFORMATION: Lys, or a conservative amino acid substitution
      thereof, or any amino acid
<220> FEATURE:
<221> NAME/KEY: MOD_RES
<222> LOCATION: (7)..(7)
<223> OTHER INFORMATION: Thr, or a conservative amino acid substitution
      thereof, or any amino acid
<220> FEATURE:
<221> NAME/KEY: MOD_RES
<222> LOCATION: (8)..(8)
<223> OTHER INFORMATION: Gly, or a conservative amino acid substitution
      thereof, or any amino acid
<220> FEATURE:
<221> NAME/KEY: MOD_RES
<222> LOCATION: (9)..(9)
<223> OTHER INFORMATION: Ala, or a conservative amino acid substitution
      thereof, or any amino acid
<220> FEATURE:
<221> NAME/KEY: MOD_RES
<222> LOCATION: (10)..(10)
<223> OTHER INFORMATION: Leu, or a conservative amino acid substitution
      thereof, or any amino acid
<220> FEATURE:
<221> NAME/KEY: MOD_RES
<222> LOCATION: (11)..(11)
<223> OTHER INFORMATION: Leu, or a conservative amino acid substitution
      thereof, or any amino acid
<220> FEATURE:
<221> NAME/KEY: MOD_RES
```

```
<222> LOCATION: (12)..(12)
<223> OTHER INFORMATION: Leu, or a conservative amino acid substitution
      thereof, or any amino acid
<220> FEATURE:
<221> NAME/KEY: MOD_RES
<222> LOCATION: (13)..(13)
<223> OTHER INFORMATION: Gln, or a conservative amino acid substitution
      thereof, or any amino acid
<220> FEATURE:
<221> NAME/KEY: MOD_RES
<222> LOCATION: (14)..(14)
<223> OTHER INFORMATION: Gly, or a conservative amino acid substitution
      thereof, or any amino acid
<220> FEATURE:
<221> NAME/KEY: MOD_RES
<222> LOCATION: (15)..(15)
<223> OTHER INFORMATION: Phe, or a conservative amino acid substitution
      thereof, or any amino acid
<220> FEATURE:
<221> NAME/KEY: MOD_RES
<222> LOCATION: (16)..(16)
<223> OTHER INFORMATION: Ile, or a conservative amino acid substitution
      thereof, or any amino acid
<220> FEATURE:
<221> NAME/KEY: MOD_RES
<222> LOCATION: (17)..(17)
<223> OTHER INFORMATION: Gln, or a conservative amino acid substitution
      thereof, or any amino acid
<220> FEATURE:
<221> NAME/KEY: MOD_RES
<222> LOCATION: (18)..(18)
<223> OTHER INFORMATION: Asp, or a conservative amino acid substitution
      thereof, or any amino acid
<220> FEATURE:
<221> NAME/KEY: MOD_RES
<222> LOCATION: (19)..(19)
<223> OTHER INFORMATION: Arg, or a conservative amino acid substitution
      thereof, or any amino acid
<220> FEATURE:
<221> NAME/KEY: MOD_RES
<222> LOCATION: (20)..(20)
<223> OTHER INFORMATION: Ala, or a conservative amino acid substitution
      thereof, or any amino acid
<220> FEATURE:
<221> NAME/KEY: MOD_RES
<222> LOCATION: (21)..(21)
<223> OTHER INFORMATION: Gly, or a conservative amino acid substitution
      thereof, or any amino acid
<220> FEATURE:
<221> NAME/KEY: MOD_RES
<222> LOCATION: (22)..(22)
<223> OTHER INFORMATION: Arg, or a conservative amino acid substitution
      thereof, or any amino acid
<220> FEATURE:
<221> NAME/KEY: MOD_RES
<222> LOCATION: (23)..(23)
<223> OTHER INFORMATION: Met, or a conservative amino acid substitution
      thereof, or any amino acid
<220> FEATURE:
<221> NAME/KEY: MOD_RES
<222> LOCATION: (24)..(24)
<223> OTHER INFORMATION: Gly, or a conservative amino acid substitution
      thereof, or any amino acid
<220> FEATURE:
<221> NAME/KEY: MOD_RES
<222> LOCATION: (25)..(25)
<223> OTHER INFORMATION: Gly, or a conservative amino acid substitution
      thereof, or any amino acid
<220> FEATURE:
<221> NAME/KEY: MOD_RES
<222> LOCATION: (26)..(26)
<223> OTHER INFORMATION: Glu, or a conservative amino acid substitution
      thereof, or any amino acid,
<220> FEATURE:
<221> NAME/KEY: MOD_RES
<222> LOCATION: (27)..(27)
<223> OTHER INFORMATION: Ala, or a conservative amino acid substitution
      thereof, or any amino acid;
<220> FEATURE:
```

```
<223> OTHER INFORMATION: see specification as filed for detailed
      description of substitutions and preferred embodiments

<400> SEQUENCE: 149

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 150
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Glu Gln Ile Met Lys Thr Gly Ala Leu Leu Leu Gln Gly Phe Ile
1               5                   10                  15

Gln Asp Arg Ala Gly Arg Met Gly Gly Glu Ala
            20                  25

<210> SEQ ID NO 151
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(27)
<223> OTHER INFORMATION: Any amino acid

<400> SEQUENCE: 151

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 152
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Val Ala Gln Asp Thr Glu Glu Val Phe Arg Ser Tyr Val Phe Tyr Arg
1               5                   10                  15

His Gln Gln Glu Gln Glu Ala Glu Gly Val Ala
            20                  25

<210> SEQ ID NO 153
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, or a conservative amino acid substitution
      thereof, or any amino acid
```

```
-continued

<220> FEATURE:
<221> NAME/KEY: MOD_RES
<222> LOCATION: (2)..(2)
<223> OTHER INFORMATION: Glu, or a conservative amino acid substitution
      thereof, or any amino acid
<220> FEATURE:
<221> NAME/KEY: MOD_RES
<222> LOCATION: (3)..(3)
<223> OTHER INFORMATION: Arg, or a conservative amino acid substitution
      thereof, or any amino acid
<220> FEATURE:
<221> NAME/KEY: MOD_RES
<222> LOCATION: (4)..(4)
<223> OTHER INFORMATION: Thr, or a conservative amino acid substitution
      thereof, or any amino acid,
<220> FEATURE:
<221> NAME/KEY: MOD_RES
<222> LOCATION: (5)..(5)
<223> OTHER INFORMATION: Glu, or a conservative amino acid substitution
      thereof, or any amino acid
<220> FEATURE:
<221> NAME/KEY: MOD_RES
<222> LOCATION: (6)..(6)
<223> OTHER INFORMATION: Leu, or a conservative amino acid substitution
      thereof, or any amino acid
<220> FEATURE:
<221> NAME/KEY: MOD_RES
<222> LOCATION: (7)..(7)
<223> OTHER INFORMATION: Leu, or a conservative amino acid substitution
      thereof, or any amino acid
<220> FEATURE:
<221> NAME/KEY: MOD_RES
<222> LOCATION: (8)..(8)
<223> OTHER INFORMATION: Leu, or a conservative amino acid substitution
      thereof, or any amino acid
<220> FEATURE:
<221> NAME/KEY: MOD_RES
<222> LOCATION: (9)..(9)
<223> OTHER INFORMATION: Ala, or a conservative amino acid substitution
      thereof, or any amino acid
<220> FEATURE:
<221> NAME/KEY: MOD_RES
<222> LOCATION: (10)..(10)
<223> OTHER INFORMATION: Asp, or a conservative amino acid substitution
      thereof, or any amino acid
<220> FEATURE:
<221> NAME/KEY: MOD_RES
<222> LOCATION: (11)..(11)
<223> OTHER INFORMATION: Tyr, or a conservative amino acid substitution
      thereof, or any amino acid
<220> FEATURE:
<221> NAME/KEY: MOD_RES
<222> LOCATION: (12)..(12)
<223> OTHER INFORMATION: Leu, or a conservative amino acid substitution
      thereof, or any amino acid
<220> FEATURE:
<221> NAME/KEY: MOD_RES
<222> LOCATION: (13)..(13)
<223> OTHER INFORMATION: Gly, or a conservative amino acid substitution
      thereof, or any amino acid
<220> FEATURE:
<221> NAME/KEY: MOD_RES
<222> LOCATION: (14)..(14)
<223> OTHER INFORMATION: Tyr, or a conservative amino acid substitution
      thereof, or any amino acid
<220> FEATURE:
<221> NAME/KEY: MOD_RES
<222> LOCATION: (15)..(15)
<223> OTHER INFORMATION: Cys, or a conservative amino acid substitution
      thereof, or any amino acid
<220> FEATURE:
<221> NAME/KEY: MOD_RES
<222> LOCATION: (16)..(16)
<223> OTHER INFORMATION: Ala, or a conservative amino acid substitution
      thereof, or any amino acid
<220> FEATURE:
<221> NAME/KEY: MOD_RES
<222> LOCATION: (17)..(17)
<223> OTHER INFORMATION: Arg, or a conservative amino acid substitution
```

```
         thereof, or any amino acid
<220> FEATURE:
<221> NAME/KEY: MOD_RES
<222> LOCATION: (18)..(18)
<223> OTHER INFORMATION: Glu, or a conservative amino acid substitution
         thereof, or any amino acid
<220> FEATURE:
<221> NAME/KEY: MOD_RES
<222> LOCATION: (19)..(19)
<223> OTHER INFORMATION: Pro, or a conservative amino acid substitution
         thereof, or any amino acid
<220> FEATURE:
<221> NAME/KEY: MOD_RES
<222> LOCATION: (20)..(20)
<223> OTHER INFORMATION: Gly, or a conservative amino acid substitution
         thereof, or any amino acid
<220> FEATURE:
<221> NAME/KEY: MOD_RES
<222> LOCATION: (21)..(21)
<223> OTHER INFORMATION: Thr, or a conservative amino acid substitution
         thereof, or any amino acid
<220> FEATURE:
<221> NAME/KEY: MOD_RES
<222> LOCATION: (22)..(22)
<223> OTHER INFORMATION: Pro, or a conservative amino acid substitution
         thereof, or any amino acid
<220> FEATURE:
<221> NAME/KEY: MOD_RES
<222> LOCATION: (23)..(23)
<223> OTHER INFORMATION: Glu, or a conservative amino acid substitution
         thereof, or any amino acid
<220> FEATURE:
<221> NAME/KEY: MOD_RES
<222> LOCATION: (24)..(24)
<223> OTHER INFORMATION: Pro, or a conservative amino acid substitution
         thereof, or any amino acid
<220> FEATURE:
<221> NAME/KEY: MOD_RES
<222> LOCATION: (25)..(25)
<223> OTHER INFORMATION: Ala, or a conservative amino acid substitution
         thereof, or any amino acid
<220> FEATURE:
<221> NAME/KEY: MOD_RES
<222> LOCATION: (26)..(26)
<223> OTHER INFORMATION: Pro, or a conservative amino acid substitution
         thereof, or any amino acid,
<220> FEATURE:
<221> NAME/KEY: MOD_RES
<222> LOCATION: (27)..(27)
<223> OTHER INFORMATION: Ser, or a conservative amino acid substitution
         thereof, or any amino acid;
<220> FEATURE:
<223> OTHER INFORMATION: see specification as filed for detailed
         description of substitutions and preferred embodiments

<400> SEQUENCE: 153

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 154
<211> LENGTH: 27
<212> TYPE: PRT
<213> ORGANISM: Artificial Sequence
<220> FEATURE:
<223> OTHER INFORMATION: Description of Artificial Sequence: Synthetic
         peptide

<400> SEQUENCE: 154

Arg Glu Arg Thr Glu Leu Leu Leu Ala Asp Tyr Leu Gly Tyr Cys Ala
1               5                   10                  15

Arg Glu Pro Gly Thr Pro Glu Pro Ala Pro Ser
            20                  25
```

<210> SEQ ID NO 155
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Leu Arg Arg Ser Ser Val Phe Ala Ala Glu Ile Met Asp Ala Phe Asp
1               5                   10                  15

Arg Ser Pro Thr Asp Lys Glu Leu Val Ala Gln Ala Lys Ala Leu Gly
            20                  25                  30

Arg Glu Tyr Val His Ala Arg Leu Leu Arg Ala Gly Leu Ser Trp Ser
        35                  40                  45

Ala Pro Glu Arg Ala Ala Pro Val Pro Gly Arg Leu Ala Glu Val Cys
    50                  55                  60

Ala Val Leu
65

<210> SEQ ID NO 156
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr
    50                  55

<210> SEQ ID NO 157
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
        35                  40                  45

Ala Glu Gly Val Ala Ala Pro Ala Asp Pro Glu Met Val Thr Leu Pro
    50                  55                  60

Leu Gln Pro
65

<210> SEQ ID NO 158
<211> LENGTH: 26

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (19)..(19)
<223> OTHER INFORMATION: Any uncross-linked or cross-linked amino acid
      in R-or S-orientation
<220> FEATURE:
<221> NAME/KEY: MOD_RES
<222> LOCATION: (23)..(23)
<223> OTHER INFORMATION: Any uncross-linked or cross-linked amino acid
      in R-or S-orientation

<400> SEQUENCE: 158

His His His His His His Glu Ile Val Xaa Lys Tyr Ile His Tyr Lys
1               5                   10                  15

Leu Ser Xaa Arg Gly Tyr Xaa Trp Asp Ala
            20                  25

<210> SEQ ID NO 159
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (14)..(14)
<223> OTHER INFORMATION: Any uncross-linked or cross-linked amino acid
      in R-or S-orientation
<220> FEATURE:
<221> NAME/KEY: MOD_RES
<222> LOCATION: (19)..(19)
<223> OTHER INFORMATION: Any uncross-linked or cross-linked amino acid
      in R-or S-orientation

<400> SEQUENCE: 159

His His His His His His Glu Ile Val Xaa Lys Tyr Ile Xaa Tyr Lys
1               5                   10                  15

Leu Gln Xaa Arg Gly Tyr Glu Trp Asp Ala
            20                  25

<210> SEQ ID NO 160
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (19)..(19)
<223> OTHER INFORMATION: Any uncross-linked or cross-linked amino acid
      in R-or S-orientation
<220> FEATURE:
<221> NAME/KEY: MOD_RES
<222> LOCATION: (23)..(23)

<223> OTHER INFORMATION: Any uncross-linked or cross-linked amino acid
      in R-or S-orientation

<400> SEQUENCE: 160

His His His His His His Glu Ile Val Xaa Ala Tyr Ile His Tyr Lys
1               5                   10                  15

Leu Ser Xaa Arg Gly Tyr Xaa Trp Asp Ala
            20                  25

<210> SEQ ID NO 161
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (19)..(19)
<223> OTHER INFORMATION: Any uncross-linked or cross-linked amino acid
      in R-or S-orientation
<220> FEATURE:
<221> NAME/KEY: MOD_RES
<222> LOCATION: (23)..(23)
<223> OTHER INFORMATION: Any uncross-linked or cross-linked amino acid
      in R-or S-orientation

<400> SEQUENCE: 161

His His His His His His Glu Ile Val Xaa Lys Tyr Ile His Tyr Lys
1               5                   10                  15

Ala Ser Xaa Arg Gly Tyr Xaa Trp Asp Ala
            20                  25

<210> SEQ ID NO 162
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (19)..(19)
<223> OTHER INFORMATION: Any uncross-linked or cross-linked amino acid
      in R-or S-orientation
<220> FEATURE:
<221> NAME/KEY: MOD_RES
<222> LOCATION: (23)..(23)
<223> OTHER INFORMATION: Any uncross-linked or cross-linked amino acid
      in R-or S-orientation

<400> SEQUENCE: 162

His His His His His His Glu Ile Val Xaa Lys Tyr Ala His Tyr Lys
1               5                   10                  15

Ala Ser Xaa Arg Gly Tyr Xaa Trp Asp Ala
            20                  25

<210> SEQ ID NO 163
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 163

Glu Cys Val Xaa Lys Tyr Ile His Tyr Lys Leu Ser Xaa Arg Gly Tyr
1               5                  10                  15

Xaa Trp Asp Ala
            20

<210> SEQ ID NO 164
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation

<400> SEQUENCE: 164

Glu Ile Val Xaa Lys Tyr Ile His Tyr Cys Leu Ser Xaa Arg Gly Tyr
1               5                  10                  15

Xaa Trp Asp Ala
            20

<210> SEQ ID NO 165
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (13)..(13)
<223> OTHER INFORMATION: Any uncross-linked or cross-linked amino acid
      in R-or S-orientation
<220> FEATURE:
<221> NAME/KEY: MOD_RES
<222> LOCATION: (17)..(17)
<223> OTHER INFORMATION: Any uncross-linked or cross-linked amino acid
      in R-or S-orientation
```

-continued

```
<400> SEQUENCE: 165

Glu Ile Val Xaa Lys Tyr Ile His Tyr Lys Leu Ser Xaa Arg Gly Cys
1               5                   10                  15

Xaa Trp Asp Ala
            20

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any uncross-linked or cross-linked amino acid
      in R-or S-orientation
<220> FEATURE:
<221> NAME/KEY: MOD_RES
<222> LOCATION: (9)..(9)
<223> OTHER INFORMATION: Any uncross-linked or cross-linked amino acid
      in R-or S-orientation

<400> SEQUENCE: 166

Lys Tyr Ile His Xaa Lys Leu Ser Xaa Arg Gly Tyr Glu Trp Asp Ala
1               5                   10                  15

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: This sequence may encompass 2, 3, 4, 5, 6, 7,
      8 or 9 residues, wherein some positions may be absent

<400> SEQUENCE: 167

Arg Arg Arg Arg Arg Arg Arg Arg Arg
1               5

<210> SEQ ID NO 168
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Cys
<220> FEATURE:
<221> NAME/KEY: MOD_RES
<222> LOCATION: (3)..(3)
<223> OTHER INFORMATION: Glu or Ala
<220> FEATURE:
<221> NAME/KEY: MOD_RES
<222> LOCATION: (4)..(4)
<223> OTHER INFORMATION: Ile, Ala, or Selenocysteine
<220> FEATURE:
<221> NAME/KEY: MOD_RES
<222> LOCATION: (5)..(5)
<223> OTHER INFORMATION: Val or Ala
<220> FEATURE:
<221> NAME/KEY: MOD_RES
<222> LOCATION: (6)..(6)
<223> OTHER INFORMATION: Met, Asp, Asn, Ala, Cys, or Selenocysteine
```

```
<220> FEATURE:
<221> NAME/KEY: MOD_RES
<222> LOCATION: (7)..(7)
<223> OTHER INFORMATION: Lys, Ala, or Asp
<220> FEATURE:
<221> NAME/KEY: MOD_RES
<222> LOCATION: (8)..(8)
<223> OTHER INFORMATION: Tyr or Ala
<220> FEATURE:
<221> NAME/KEY: MOD_RES
<222> LOCATION: (9)..(9)
<223> OTHER INFORMATION: Ile, Ala, or Selenocysteine
<220> FEATURE:
<221> NAME/KEY: MOD_RES
<222> LOCATION: (10)..(10)
<223> OTHER INFORMATION: His, Ala, or Selenocysteine
<220> FEATURE:
<221> NAME/KEY: MOD_RES
<222> LOCATION: (11)..(11)
<223> OTHER INFORMATION: Tyr or Ala
<220> FEATURE:
<221> NAME/KEY: MOD_RES
<222> LOCATION: (13)..(13)
<223> OTHER INFORMATION: Leu or Ala
<220> FEATURE:
<221> NAME/KEY: MOD_RES
<222> LOCATION: (14)..(14)
<223> OTHER INFORMATION: Ser or Ala
<220> FEATURE:
<221> NAME/KEY: MOD_RES
<222> LOCATION: (16)..(16)
<223> OTHER INFORMATION: Arg, Ala, or Glu
<220> FEATURE:
<221> NAME/KEY: MOD_RES
<222> LOCATION: (17)..(17)
<223> OTHER INFORMATION: Gly, Ala, or Glu
<220> FEATURE:
<221> NAME/KEY: MOD_RES
<222> LOCATION: (18)..(18)
<223> OTHER INFORMATION: Tyr, Ala, Arg, or Selenocysteine
<220> FEATURE:
<221> NAME/KEY: MOD_RES
<222> LOCATION: (20)..(20)
<223> OTHER INFORMATION: Trp, Ala, Arg, or Selenocysteine
<220> FEATURE:
<221> NAME/KEY: MOD_RES
<222> LOCATION: (21)..(21)
<223> OTHER INFORMATION: Asp or Ala
<220> FEATURE:
<221> NAME/KEY: MOD_RES
<222> LOCATION: (22)..(22)
<223> OTHER INFORMATION: Ala or Glu
<220> FEATURE:
<221> NAME/KEY: MOD_RES
<222> LOCATION: (23)..(23)
<223> OTHER INFORMATION: Gly or Cys

<400> SEQUENCE: 168

Asn Xaa Xaa Xaa Xaa Xaa Xaa Xaa Xaa Xaa Xaa Lys Xaa Xaa Gln Xaa
1               5                   10                  15

Xaa Xaa Glu Xaa Xaa Xaa Xaa Asp
            20

<210> SEQ ID NO 169
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Val
<220> FEATURE:
<221> NAME/KEY: MOD_RES
```

```
<222> LOCATION: (5)..(5)
<223> OTHER INFORMATION: Val, Lys, or Selenocysteine
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (8)..(8)
<223> OTHER INFORMATION: Leu, Ala, or Selenocysteine
<220> FEATURE:
<221> NAME/KEY: MOD_RES
<222> LOCATION: (9)..(9)
<223> OTHER INFORMATION: Ser or Selenocysteine
<220> FEATURE:
<221> NAME/KEY: MOD_RES
<222> LOCATION: (17)..(17)
<223> OTHER INFORMATION: Tyr or Selenocysteine
<220> FEATURE:
<221> NAME/KEY: MOD_RES
<222> LOCATION: (20)..(20)
<223> OTHER INFORMATION: Ser or selenocystein
<220> FEATURE:
<221> NAME/KEY: MOD_RES
<222> LOCATION: (22)..(22)
<223> OTHER INFORMATION: Phe or Asp

<400> SEQUENCE: 169

Arg Glu Xaa Val Xaa Xaa Phe Xaa Xaa Tyr Lys Leu Ser Gln Lys Gly
1               5                   10                  15

Xaa Ser Trp Xaa Gln Xaa
            20

<210> SEQ ID NO 170
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Selenocysteine
<220> FEATURE:
<221> NAME/KEY: MOD_RES
<222> LOCATION: (4)..(4)
<223> OTHER INFORMATION: Cys or Val
<220> FEATURE:
<221> NAME/KEY: MOD_RES
<222> LOCATION: (5)..(5)
<223> OTHER INFORMATION: Ala or Selenocysteine
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (8)..(8)
<223> OTHER INFORMATION: Val or Selenocysteine
<220> FEATURE:
<221> NAME/KEY: MOD_RES
<222> LOCATION: (9)..(9)
<223> OTHER INFORMATION: Gly or Selenocysteine
<220> FEATURE:
<221> NAME/KEY: MOD_RES
<222> LOCATION: (12)..(12)
<223> OTHER INFORMATION: Leu or Ala
<220> FEATURE:
<221> NAME/KEY: MOD_RES
<222> LOCATION: (19)..(19)
<223> OTHER INFORMATION: Cys, Asp, or Asn
<220> FEATURE:
<221> NAME/KEY: MOD_RES
<222> LOCATION: (22)..(22)
<223> OTHER INFORMATION: Gly or Asp
```

```
<400> SEQUENCE: 170

Arg Ala Xaa Xaa Xaa Xaa Phe Xaa Xaa Tyr Lys Xaa Arg Gln Lys Gly
1               5                   10                  15

Tyr Val Xaa Gly Ala Xaa
            20

<210> SEQ ID NO 171
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asn Arg Glu Ile Val Met Lys Tyr Ile His Tyr Lys Leu Ser Gln Arg
1               5                   10                  15

Gly Tyr Glu Trp Asp Ala Gly Asp
            20

<210> SEQ ID NO 172
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Ala Leu Cys Ala Asp Phe Val Gly Tyr Lys Leu Arg Gln Lys Gly
1               5                   10                  15

Tyr Val Cys Gly Ala Gly
            20
```

BH4 STABILIZED PEPTIDES AND USES THEREOF

CROSS-REFERENCE TO RELATED APPLICATIONS

The present application is the National Phase of International Application Serial No. PCT/US2014/029318, filed on Mar. 14, 2014, which claims the benefit of U.S. Provisional Patent Application Ser. No. 61/792,188, filed on Mar. 15, 2013, both of which are herein incorporated by reference in their entirety.

FEDERALLY SPONSORED RESEARCH

This invention was made with Government support under grant numbers 5R01 GM090299-04 and 5R01 CA050239-23 awarded by the National Institutes of Health. The Government has certain rights in the invention.

BACKGROUND OF THE INVENTION

Cells are continually faced with the decision of whether to live or die in the context of development, homeostasis, stress, and injury. Ultimately, the cell's response is strongly influenced by protein interactions of the B-cell lymphoma 2 (BCL-2) family. Deregulation of these proteins can result in inappropriate cellular persistence or premature cell death, leading to a variety of diseases, such as cancer and neurodegenerative disorders, respectively. Since the initial discovery of BCL-2, numerous homologues have been identified that together form an intricate signaling network that regulates apoptosis. Family members are defined by the presence of at least one BCL-2 homology domain (BH1-4), and are classified as multidomain anti-apoptotic, multidomain pro-apoptotic, or BH3-only pro-apoptotic proteins (Youle et al., *Nature Reviews Mol. Cell Biol.* 9:47-59, 2008). The BH3-only proteins are death sentinels that transmit signals of cellular stress to multidomain members (Kuwana et al., *Mol. Cell* 17:525-535, 2005). The anti-apoptotic proteins can bind and sequester the BH3-only and multidomain pro-apoptotic proteins to block apoptosis (Sedlak et al., *Proc. Natl. Acad. Sci. U.S.A.* 92:7834-7838, 1995). However, sustained cell stress can overcome the anti-apoptotic reserve, leading to activation of a multidomain pro-apoptotic protein BCL-2-associated X protein (BAX), which forms toxic pores in the outer mitochondrial membrane (OMM) and releases cytochrome c and other apoptogenic factors (Chipuk et al., *Trends Cell. Biol.* 18:157-164, 2008; Dejean et al., *Mol. Biol. Cell.* 16:2424-2432, 2005; and Jürgensmeier et al., *Proc. Natl. Acad. Sci. U.S.A.* 95:4997-5002, 1998). Upon initiation of apoptosis by death signals or cytotoxic stress, cytosolic BAX is triggered to undergo a major conformational change, leading to translocation to the mitochondria and formation of oligomeric pores (Wolter et al., *J. Cell Biol.* 139:1281-1292, 1997; Nechushtan et al., *EMBO J.* 18:2330-2341, 1999; Gavathiotis et al., *Nature* 455:1076-1081, 2008; and Gavathiotis et al., *Molecular Cell* 40:481-492, 2010), which triggers apoptosis of the cell.

SUMMARY OF THE INVENTION

The invention is based, at least in part, on the design of internally cross-linked polypeptides and modified polypeptides that contain a sequence based on a BH4 domain of a BCL-2 family protein, and the discovery that these cross-linked polypeptides and modified polypeptides are capable of binding to BAX protein, potently inhibiting BAX protein activity, and inhibiting cytotoxic stress-induced cell death (e.g., apoptosis) in mammalian cells. In view of these discoveries, provided herein are internally cross-linked polypeptides and modified polypeptides that contain a sequence based on a BH4 domain of a BCL-2 family protein that targets, e.g., multidomain pro-apoptotic BCL-2 family members, such as BAX and its close homologues BAK and BOK, and perhaps other physiologic targets. Also provided herein are pharmaceutical compositions and kits that contain at least one of these internally cross-linked polypeptides or modified polypeptides, methods of using these internally cross-linked polypeptides or modified polypeptides to treat a cytotoxic disease in a subject, decrease stress-induced cell death (e.g., apoptosis) in a subject, increase cell death (e.g., apoptosis) in a subject, or treat a cell proliferative disorder (e.g., any of the cancers described herein or known in the art) in a subject, and methods for identifying agents that interact with BAX protein and/or its close homologues BAK and BOK, and/or modulate the activity of BAX protein and/or its close homologues BAK and BOK.

Provided herein are internally cross-linked polypeptides that include between 15 to 24 contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0$ (SEQ ID NO: 135) wherein:

$A_0$ is Asn, or a conservative amino acid substitution thereof, $B_0$ is Arg or Cys, or a conservative amino acid substitution thereof, $C_0$ is Glu or Ala, or a conservative amino acid substitution thereof, $D_0$ is Ile, Ala, or selenocysteine, or a conservative amino acid substitution thereof, $E_0$ is Val or Ala, or a conservative amino acid substitution thereof, $F_0$ is Met, Asp, Asn, Ala, or Cys, or selenocysteine, or a conservative amino acid substitution thereof, $G_0$ is Lys, Ala, or Asp, or a conservative amino acid substitution thereof, $H_0$ is Tyr or Ala, or a conservative amino acid substitution thereof, $I_0$ is Ile, Ala, or selenocysteine, or a conservative amino acid substitution thereof, $J_0$ is His, Ala, or selenocysteine, or a conservative amino acid substitution thereof, $K_0$ is Tyr or Ala, or a conservative amino acid substitution thereof, $L_0$ is Lys, or a conservative amino acid substitution thereof, $M_0$ is Leu or Ala, or a conservative amino acid substitution thereof, $N_0$ is Ser or Ala, or a conservative amino acid substitution thereof, $O_0$ is Gln, or a conservative amino acid substitution thereof, $P_0$ is Arg, Ala, or Glu, or a conservative amino acid substitution thereof, $Q_0$ is Gly, Ala, or Glu, or a conservative amino acid substitution thereof, $R_0$ is Tyr, Ala, Arg, or selenocysteine, or a conservative amino acid substitution thereof, $S_0$ is Glu, or a conservative amino acid substitution thereof, $T_0$ is Trp, Ala, Arg, or selenocysteine, or a conservative amino acid substitution thereof, $U_0$ is Asp or Ala, or a conservative amino acid substitution thereof, $V_0$ is Ala or Glu, or a conservative amino acid substitution thereof, $W_0$ is Gly or Cys, or a conservative amino acid substitution thereof, and $X_0$ is Asp, or a conservative amino acid substitution thereof, and wherein:

the side chains of two amino acids separated by two to six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some embodiments of these cross-linked polypeptides, $A_0$ is Asn, $B_0$ is Arg or Cys, $C_0$ is Glu or Ala, $D_0$ is Ile, Ala, or selenocysteine, $E_0$ is Val or Ala, $F_0$ is Met, Asp, Asn, Ala, Cys, or selenocysteine, $G_0$ is Lys, Ala, or Asp, $H_0$ is Tyr or Ala, $I_0$ is Ile, Ala, or selenocysteine, $J_0$ is His, Ala, or selenocysteine, $K_0$ is Tyr or Ala, $L_0$ is Lys, $M_0$ is Leu or Ala, $N_0$ is Ser or Ala, $O_0$ is Gln, $P_0$ is Arg, Ala, or Glu, $Q_0$ is Gly, Ala, or Glu, $R_0$ is Tyr, Ala, Arg, or selenocysteine, $S_0$ is Glu, $T_0$ is Trp, Ala, Arg, or selenocysteine, $U_0$ is Asp or Ala, $V_0$ is Ala or Glu, $W_0$ is Gly or Cys, and $X_0$ is Asp. In some cases the peptide consists of no more than 15, 16, 17, 18, 19, 20, 21, 22, 23, 24, 25, 26, 27, 28, 29 or 30 contiguous amino acids of the forgoing sequence, but can include a targeting moiety or a moiety that facilitates cell entry or 2, 3, 4, 5, 6, 7, 8 or 9 contiguous Arg at the amino or carboxy terminus.

In some embodiments of these cross-linked polypeptides, $A_0$ is Asn, $B_0$ is Arg or Cys, $C_0$ is Glu or Ala, $D_0$ is Ile, Ala, or selenocysteine, $E_0$ is Val or Ala, $F_0$ is Met, Asp, Asn, Ala, Cys, or selenocysteine, $G_0$ is Lys, Ala, or Asp, $H_0$ is Tyr or Ala, $I_0$ is Ile, Ala, or selenocysteine, $J_0$ is His, Ala, or selenocysteine, $K_0$ is Tyr or Ala, $L_0$ is Lys, $M_0$ is Leu or Ala, $N_0$ is Ser or Ala, $O_0$ is Gln, $P_0$ is Arg, Ala, or Glu, $Q_0$ is Gly, Ala, or Glu, $R_0$ is Tyr, Ala, Arg, or selenocysteine, $S_0$ is Glu, $T_0$ is Trp, Ala, Arg, or selenocysteine, $U_0$ is Asp or Ala, $V_0$ is Ala or Glu, $W_0$ is Gly or Cys, and $X_0$ is Asp, and wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, and $X_0$ are replaced by a conservative amino acid substitution that does not alter the binding face of the peptide; and/or the polypeptide contains a sequence that is at least 80% (e.g., 80%, 85%, 90%, 95%, 98%, 99%, 99.5%, or 100%) identical to the sequence of SEQ ID NO:1. In some embodiments of any of these internally cross-linked polypeptides, the internal staple replacing the side chains of the two amino acids separated by two to six amino acids comprises an internal staple selected from Table 1. In some embodiments of any of these internally cross-linked polypeptides, the internal staples and/or the internal stitch replacing the side chains of the three amino acids comprise an internal stitch selected from Table 1.

Also provided are internally cross-linked polypeptides that include (i) the amino acid sequence of EIVMKYI-HYKLSQRGYEWDA (SEQ ID NO: 1) or (ii) a sequence containing between one to six amino acid substitutions in the sequence of SEQ ID NO: 1, and wherein: the side chains of two amino acids separated by two to six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some embodiments of any of these internally cross-linked polypeptides, one or more of the side chains replaced by an internal staple and/or an internal stitch are selected from the group consisting of amino acid positions 5, 9, 13, 17, and 21 of SEQ ID NO: 1. In some embodiments of any of these internally cross-linked polypeptides, one or more of the side chains replaced by an internal staple and/or an internal stitch are selected from the group consisting of amino acid positions 4, 8, 12, 16, and 20 of SEQ ID NO: 1.

Also provided are internally cross-linked polypeptides that include 15 to 22 contiguous amino acids of the amino acid sequence $A_0B_0C_0D_0E_0F_0G_0H_0I_0J_0K_0L_0M_0N_0O_0P_0Q_0R_0S_0T_0U_0V_0$ (SEQ ID NO: 136) wherein:

$A_0$ is Arg, or a conservative amino acid substitution thereof, $B_0$ is Glu, or a conservative amino acid substitution thereof, $C_0$ is Leu or Val, or a conservative amino acid substitution thereof, $D_0$ is Val, or a conservative amino acid substitution thereof, $E_0$ is Val, Lys, or selenocysteine, or a conservative amino acid substitution thereof, $F_0$ is Asp or Lys, or a conservative amino acid substitution thereof, $G_0$ is Phe or a conservative amino acid substitution thereof, $H_0$ is Leu, Ala, or selenocysteine, or a conservative amino acid substitution thereof, $I_0$ is Ser or selenocysteine, or a conservative amino acid substitution thereof, $J_0$ is Tyr or a conservative amino acid substitution thereof, $K_0$ is Lys or a conservative amino acid substitution thereof, $L_0$ is Leu, or a conservative amino acid substitution thereof, $M_0$ is Ser or a conservative amino acid substitution thereof, $N_0$ is Gln or a conservative amino acid substitution thereof, $O_0$ is Lys or a conservative amino acid substitution thereof, $P_0$ is Gly or a conservative amino acid substitution thereof, $Q_0$ is Tyr or selenocysteine, or a conservative amino acid substitution thereof, $R_0$ is Ser or a conservative amino acid substitution thereof, $S_0$ is Trp or a conservative amino acid substitution thereof, $T_0$ is Ser or selenocysteine, or a conservative amino acid substitution thereof, $U_0$ is Gln or a conservative amino acid substitution thereof, and $V_0$ is Phe or Asp, or a conservative amino acid substitution thereof, and wherein: the side chains of two amino acids separated by two to six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some embodiments of any of these internally cross-linked polypeptides, $A_0$ is Arg, $B_0$ is Glu, $C_0$ is Leu or Val, $D_0$ is Val, $E_0$ is Val, Lys, or selenocysteine, $F_0$ is Asp or Lys, $G_0$ is Phe, $H_0$ is Leu, Ala, or selenocysteine, $I_0$ is Ser or selenocysteine, $J_0$ is Tyr, $K_0$ is Lys, $L_0$ is Leu, $M_0$ is Ser, $N_0$ is Gln, $O_0$ is Lys, $P_0$ is Gly, $Q_0$ is Tyr or selenocysteine, $R_0$ is Ser, $S_0$ is Trp, $T_0$ is Ser or selenocysteine, $U_0$ is Gln, and $V_0$ is Phe or Asp. In some cases the peptide consists of no more than 15, 16, 17, 18, 19, 20, 21, 22, 23, 24, 25, 26, 27, 28, 29 or 30 contiguous amino acids of the forgoing sequence, but can include a targeting moiety or a moiety that facilitates cell entry or 2, 3, 4, 5, 6, 7, 8 or 9 contiguous Arg at the amino or carboxy terminus.

In some embodiments of any of these internally cross-linked polypeptides, $A_0$ is Arg, $B_0$ is Glu, $C_0$ is Leu or Val, $D_0$ is Val, $E_0$ is Val, Lys, or selenocysteine, $F_0$ is Asp or Lys, $G_0$ is Phe, $H_0$ is Leu, Ala, or selenocysteine, $I_0$ is Ser or selenocysteine, $J_0$ is Tyr, $K_0$ is Lys, $L_0$ is Leu, $M_0$ is Ser, $N_0$ is Gln, $O_0$ is Lys, $P_0$ is Gly, $Q_0$ is Tyr or selenocysteine, $R_0$ is Ser, $S_0$ is Trp, $T_0$ is Ser or selenocysteine, $U_0$ is Gln, and $V_0$ is Phe or Asp, and wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, and $V_0$ are replaced by a conservative amino acid substitution that does not alter the binding face of the peptide; and/or the polypeptide contains a sequence that is at least 80% (e.g., 80%, 85%, 90%, 95%, 98%, 99%, 99.5%, or 100%) identical to the sequence of SEQ ID NO: 2. In some embodiments of any of these internally cross-linked polypeptides, the internal staple replacing the side chains of the two amino acids separated by two to six amino acids comprises an internal staple selected from Table 2. In some embodiments of any of these internally cross-linked polypeptides, the internal staples and/or the internal stitch replacing the side chains of the three amino acids comprise an internal stitch selected from Table 2.

Also provided are internally cross-linked polypeptides that include (i) the amino acid sequence of RELVVDFL-SYKLSQKGYSWSQF (SEQ ID NO: 2) or (ii) a sequence containing between one to six amino acid substitutions in the sequence of SEQ ID NO: 2, and wherein: the side chains of two amino acids separated by two to six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

Also provided are internally cross-linked polypeptides that include 15 to 22 contiguous amino acids of the amino acid sequence $A_0B_0C_0D_0E_0F_0G_0H_0I_0J_0K_0L_0M_0N_0O_0P_0Q_0R_0S_0T_0U_0V_0$ (SEQ ID NO: 137) wherein:

$A_0$ is Arg or a conservative amino acid substitution thereof, $B_0$ is Ala or a conservative amino acid substitution thereof, $C_0$ is Leu or selenocysteine, or a conservative amino acid substitution thereof, $D_0$ is Cys or Val, or a conservative amino acid substitution thereof, $E_0$ is Ala or selenocysteine, or a conservative amino acid substitution thereof, $F_0$ is Asp or Lys, or a conservative amino acid substitution thereof, $G_0$ is Phe or a conservative amino acid substitution thereof, $H_0$ is Val or selenocysteine, or a conservative amino acid substitution thereof, $I_0$ is Gly or selenocystine, or a conservative amino acid substitution thereof, $J_0$ is Tyr or a conservative amino acid substitution thereof, $K_0$ is Lys or a conservative amino acid substitution thereof, $L_0$ is Leu or Ala, or a conservative amino acid substitution thereof, $M_0$ is Arg or a conservative amino acid substitution thereof, $N_0$ is Gln or a conservative amino acid substitution thereof, $O_0$ is Lys or a conservative amino acid substitution thereof, $P_0$ is Gly or a conservative amino acid substitution thereof, $Q_0$ is Tyr or a conservative amino acid substitution thereof, $R_0$ is Val or a conservative amino acid substitution thereof, $S_0$ is Cys, Asp, or Asn, or a conservative amino acid substitution thereof, $T_0$ is Gly or a conservative amino acid substitution thereof, $U_0$ is Ala or a conservative amino acid substitution thereof, and $V_0$ is Gly or Asp, or a conservative amino acid substitution thereof, and wherein: the side chains of two amino acids separated by two to six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some embodiments of any of these internally cross-linked polypeptides, $A_0$ is Arg, $B_0$ is Ala, $C_0$ is Leu or selenocysteine, $D_0$ is Cys or Val, $E_0$ is Ala or selenocysteine, $F_0$ is Asp or Lys, $G_0$ is Phe, $H_0$ is Val or selenocysteine, $I_0$ is Gly or selenocystine, $J_0$ is Tyr, $K_0$ is Lys, $L_0$ is Leu or Ala, $M_0$ is Arg, $N_0$ is Gln, $O_0$ is Lys, $P_0$ is Gly, $Q_0$ is Tyr, $R_0$ is Val, $S_0$ is Cys, Asp, or Asn, $T_0$ is Gly, $U_0$ is Ala, and $V_0$ is Gly or Asp In some cases the peptide consists of no more than 15, 16, 17, 18, 19, 20, 21, 22, 23, 24, 25, 26, 27, 28, 29 or 30 contiguous amino acids of the forgoing sequence, but can include a targeting moiety or a moiety that facilitates cell entry or 2, 3, 4, 5, 6, 7, 8 or 9 contiguous Arg at the amino or carboxy terminus.

In some embodiments of any of these internally cross-linked polypeptides, $A_0$ is Arg, $B_0$ is Ala, $C_0$ is Leu or selenocysteine, $D_0$ is Cys or Val, $E_0$ is Ala or selenocysteine, $F_0$ is Asp or Lys, $G_0$ is Phe, $H_0$ is Val or selenocysteine, $I_0$ is Gly or selenocystine, $J_0$ is Tyr, $K_0$ is Lys, $L_0$ is Leu or Ala, $M_0$ is Arg, $N_0$ is Gln, $O_0$ is Lys, $P_0$ is Gly, $Q_0$ is Tyr, $R_0$ is Val, $S_0$ is Cys, Asp, or Asn, $T_0$ is Gly, $U_0$ is Ala, and $V_0$ is Gly or Asp, and wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, and $V_0$ are replaced by a conservative amino acid substitution that does not alter the binding face of the peptide; and/or the polypeptide contains a sequence that is at least 80% (e.g., 80%, 85%, 90%, 95%, 98%, 99%, 99.5%, or 100%) identical to the sequence of SEQ ID NO: 3. In some embodiments of any of these internally cross-linked polypeptides, the internal staple replacing the side chains of the two amino acids separated by two to six amino acids comprises an internal staple selected from Table 3. In some embodiments of any of these internally cross-linked polypeptides, the internal staples and/or the internal stitch replacing the side chains of the three amino acids comprise an internal stitch selected from Table 3.

Also provided are internally cross-linked polypeptides that include: (i) the amino acid sequence of ALVADFV-GYKLRQKGYVCGA (SEQ ID NO: 3) or (ii) a sequence containing between one to six amino acid substitutions in the sequence of SEQ ID NO: 3, and wherein: the side chains of two amino acids separated by two to six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

In any of the internally cross-linked polypeptides described herein, the one or six amino acid substitutions are conservative amino acid substitutions that do not alter the binding of the peptide. In any of the internally cross-linked polypeptides described herein, the internally cross-linked polypeptide comprises a sequence selected from the group of: SEQ ID NOs: 1-71. In some embodiments of any of the internally cross-linked polypeptides described herein, the internally cross-linked polypeptide comprises or consists of a sequence selected from the group of: SEQ ID NOs: 1-71.

In some embodiments of any of the internally cross-linked polypeptides described herein, the internal staples and/or the internal stitch replacing the side chains of the three amino acids comprises at least two internal staples. In some embodiments of any of the internally cross-linked polypeptides described herein, the internal staples and/or the internal stitch replacing the side chains of the three amino acids comprises a combination of at least one internal staple and an internal stitch. In some embodiments of any of the internally cross-linked polypeptides described herein, the internal stitch replaces the side chain of a first amino acid and a second and a third amino acid thereby cross-linking the first amino acid to the second and third amino acid via an internal cross-link, wherein the first and second amino acid are separated by two, three, five, or six amino acids, the first and the third amino acids are separated by two, three, six, seven, or eleven amino acids, and the second and third amino acids are distinct amino acids. In some embodiments of any of the internally cross-linked polypeptides described herein, the internal stitch replacing the side chains of the three amino acids cross-links a pair of amino acids separated by two, three, or six amino acids. In some embodiments of any of the internally cross-linked polypeptides described herein, the side chains of the four amino acids are replaced by two distinct internal staples. In some embodiments of any of the internally cross-linked polypeptides described herein, a first of the two distinct internal staples cross-links a first pair of amino acids separated by two, three, or six amino acids, and a second of the at least two distinct internal staples cross-links a second pair of amino acids separated by two, three, or six amino acids. In some embodiments of any of the internally cross-linked polypeptides described herein, the internal staples, internal stitches, or the combination of internal staples and internal stitches replacing the side chains of the at least four amino acids comprises at least one staple and at least one stitch. In some embodiments of any of the internally cross-linked polypeptides described herein, the at least one staple cross-links a pair of amino acids separated by two, three, five, or six amino acids and the at least one stitch cross-links a first amino acid to a second amino acid and a third amino acid, wherein the first and second amino acid are separated by two, three, five, or six amino acids, the first and the third amino acids are separated by two, three, six, seven, or eleven amino acids, and the second and third amino acids are distinct amino acids. In some embodiments of any of the internally cross-linked polypeptides described herein, the at least one staple is selected from Tables 1-3.

In some cases the internally cross-linked, stapled or stitched polypeptide consists of no more than 15, 16, 17, 18, 19, 20, 21, 22, 23, 24, 25, 26, 27, 28, 29 or 30 contiguous amino acids of a sequence specified herein, but can include a targeting moiety or a moiety that facilitates cell entry or 2, 3, 4, 5, 6, 7, 8 or 9 contiguous Arg at the amino or carboxy terminus.

Also provided are pharmaceutical compositions containing one or more of any of the internally cross-linked polypeptides described herein. Some embodiments of any of the pharmaceutical compositions described herein further include a cytoprotective agent. Also provided are cytoprotective compositions containing one or more of any of the internally cross-linked polypeptides described herein.

Also provided are kits for identifying agents that interact with and/or modulate the activity of BAX protein that contain one or more of any of the internally cross-linked polypeptides described herein and a polypeptide that includes the amino acid sequence of a BAX polypeptide.

Also provided are methods of treating a cytotoxic disease in a subject that include: selecting a subject having or suspected of having a cytotoxic disease; and administering to the subject an effective amount of one or more of any of the internally cross-linked polypeptides described herein. Some embodiments of any of the methods described herein further include assessing one or more symptoms associated with a cytotoxic disease in the subject before and after treatment; and continuing treatment until a decrease in the frequency, severity, or number of symptoms of a cytotoxic disease is observed.

Also provided are methods of reducing stress-induced cell death in a subject that include selecting a subject exposed to or suspected of having been exposed to a cytotoxic agent or exposure; and administering to the subject an effective amount of one or more of any the internally cross-linked polypeptides described herein. In some embodiments of any of the methods described herein, the administration is by inhalation or injection. In some embodiments of any of the methods described herein, the injection is cardiac injection or intracranial injection.

Also provided herein are methods for identifying agents that interact with BAX protein and/or modulate the activity of BAX protein that include determining a level of binding between any of the internally cross-linked polypeptide described herein and a polypeptide comprising the amino acid sequence of a BAX protein; and detecting the level of binding between the cross-linked polypeptide and a polypeptide comprising the amino acid sequence of a BAX protein in the presence of an agent; and identifying an agent that decreases the level of binding between the cross-linked polypeptide and the polypeptide comprising the amino acid sequence of a BAX protein as a candidate agent interacts with BAX protein and/or modulates the activity of BAX protein. Some embodiments of any of the methods described herein further include selecting the candidate agent. Some embodiments of any of the methods described herein further include administering the candidate agent to an animal model of a cytotoxic disease to determine if the agent reduces one or more symptoms of a cytotoxic disease in the animal model. In some embodiments of any of the compositions described herein, the composition comprises nanoparticles. In some embodiments of any of the compositions described herein, the composition is a liquid composition.

Also provided are compounds that include one or more of any of the internally cross-linked polypeptides described herein. In some embodiments of any of the compounds described herein, the compound includes polyethylene glycol or spermine. In some embodiments of any of the compounds described herein, the polyethylene glycol is linked to the cross-linked polypeptide through a biodegradable linker.

Definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1 is an alignment of the polypeptide sequences of anti-apoptotic proteins: BCL-2, BCL-XL, and BCL-W, an alignment of the polypeptide sequences of nine different BCL-2 family proteins. The alignments show a shared region of homology at the N-terminus of each of the proteins that includes α-helix 1. The sequences shown were aligned with ClustalW.

FIG. 2A is list of the different exemplary stabilized alpha-helices of BCL-2-family protein (SAHBs) modeled after the BH4 domain of BCL-2, BCL-XL, or BCL-W protein. The template sequences used to design these SAHBs each included the core BH4 region of homology at the N-terminus of the BCL-2 family of anti-apoptotic proteins.

FIG. 2B is a list of additional exemplary stabilized alpha-helices of BCL-2 BH4 SAHB compositions for inhibitory targeting and analysis of BAX.

FIG. 14A is a graph of the percentage of liposomal ANTS/DPX release following incubation of 0.75 μM BIM $SAHB_A$ and 0.75 μM recombinant BAX (normalized to 100% release); or incubation of 0.75 μM BCL-2 BH4 $SAHB_A$, 0.75 μM unmodified BH4 peptide, or 0.75 μM of various different point mutants of BH4 $SAHB_A$, 0.75 μM BIM $SAHB_A$, and 0.75 μM recombinant BAX, with liposomes containing entrapped fluorophore (ANTS) and quencher (DPX). The data shown are the mean of three experiments, and the error bars represent ±standard deviation.

FIG. 14B is a graph of the percent liposomal ANTS/DPX release following incubation of BCL-2 BH4 $SAHB_A$ or the L23A mutant version of BCL-2 BH4 $SAHB_A$ peptide with 1.5 µM BCL-2-like protein 11 (BIM) SAHB, 0.75 µM recombinant BAX, and 5 µL liposomes containing entrapped fluorophore (ANTS) and quencher (DPX). BAX alone and BAX/BIM SAHB conditions serve as negative and positive controls, respectively. The data shown are the mean of three experiments, and the error bars represent ±standard deviation.

FIG. 15A is a graph of the relative difference in deuterium level in Da over time in different BAX peptides from recombinant BAX labeled with deuterium in the absence or the presence of a two molar excess of BCL-2 BH4 $SAHB_A$ for 10 seconds (top bar in each set of four bars), 1 min (second bar from the top in each set of four bars), 10 minutes (third bar from the top in each set of four bars), and 2 hours (bottom bar in each set of four bars). The data shown are the average of two duplicate experiments where the relative difference (Da) for each peptide is equivalent to the relative deuterium uptake of the corresponding peptide in the BAX alone control minus the relative deuterium uptake of the peptide in the BCL-2 BH4 $SAHB_A$-bound BAX sample.

FIG. 16 is a graph of the crosslink occurrence of BH4 pSAHB 21 to individual amino acid residues of recombinant BAX protein as determined using LC-MS/MS, and three images (C-terminal view, bottom view, and N-terminal view) showing the binding site(s) of BH4 pSAHB 21 to recombinant BAX protein.

FIG. 17 is a graph of the crosslink occurrence of BH4 pSAHB 23 to individual amino acid residues of recombinant BAX protein as determined using LC-MS/MS, and three images (C-terminal view, bottom view, and N-terminal view) showing the binding site(s) of BH4 pSAHB 23 to recombinant BAX protein.

FIG. 18 is a graph of the crosslink occurrence of BH4 pSAHB 11 to individual amino acid residues of recombinant BAX protein as determined using LC-MS/MS, and three images (C-terminal view, bottom view, and N-terminal view) showing the binding site(s) of BH4 pSAHB 11 to recombinant BAX protein.

FIG. 21 is a table depicting various exemplary internally cross-linked polypeptides (Table 1).

FIG. 22 is a table depicting various exemplary internally cross-linked polypeptides (Table 2).

FIG. 23 is a table depicting various exemplary internally cross-linked polypeptides (Table 3).

DETAILED DESCRIPTION OF THE INVENTION

Figure 3:
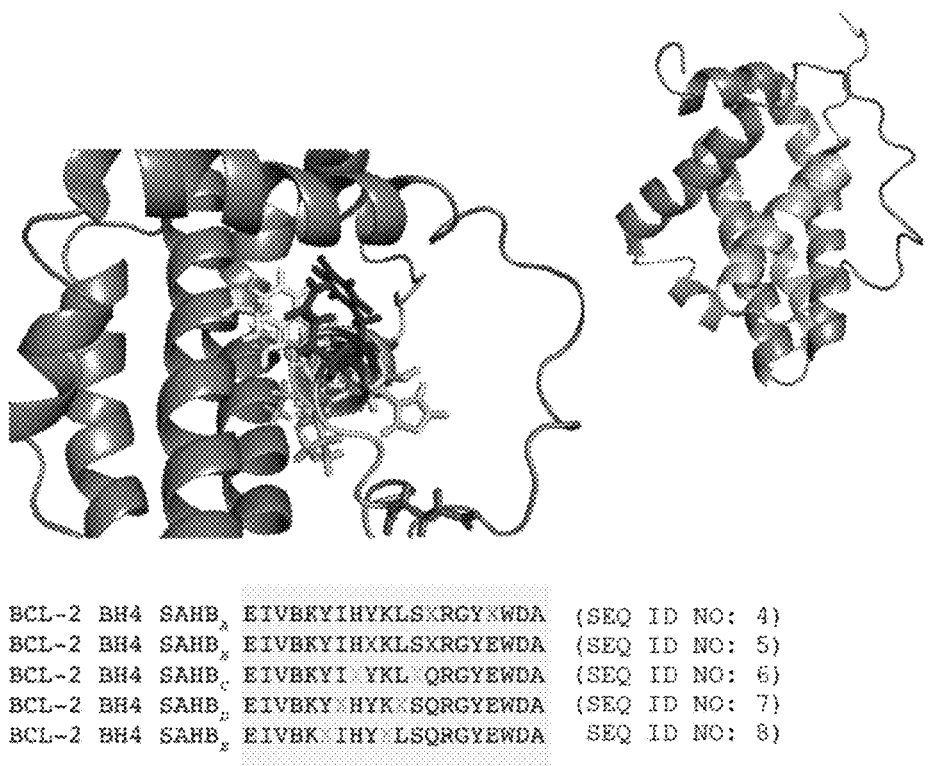
FIG. 3 is an image of exemplary SAHBs modeled after the BH4 domain of BCL-2 and the sequences of five different SAHBs modeled after the BH4 domain of BCL-2, which were designed to test the effect of the placement of the staple on different faces of the alpha-helix.

The invention is based, at least in part, on the design of internally cross-linked polypeptides and modified polypeptides that contain a sequence based on a BH4 domain of a BCL-2 family protein, and the discovery that these cross-linked polypeptides and modified polypeptides are capable of binding to BAX protein, potently inhibiting BAX protein activity, and inhibiting cytotoxic stress-induced cell death (e.g., apoptosis) in mammalian cells. In view of these discoveries, provided herein are internally cross-linked polypeptides and modified polypeptides that contain a sequence based on a BH4 domain of a BCL-2 family protein that targets, e.g., multidomain pro-apoptotic BCL-2 family members, such as BAX and its close homologues BAK and BOK, and perhaps other physiologic targets. Also provided herein are pharmaceutical compositions and kits that contain at least one of these internally cross-linked polypeptides and/or modified polypeptides, methods of using these internally cross-linked polypeptides and/or modified polypeptides to treat a cytotoxic disease in a subject, decrease stress-induced cell death (e.g., apoptosis) in a subject, increase cell death (e.g., apoptosis) in a subject, or treat a cell proliferative disorder (e.g., any of the cancers described herein or known in the art), and methods for identifying agents that interact with BAX protein and/or its close homologues BAK and BOK, and/or modulate the activity of BAX protein and/or its close homologues BAK and BOK. Non-limiting aspects and embodiments of these methods are described herein. Any of the aspects described below can be used in any combination in the methods described herein.

Internally Cross-Linked Polypeptides

The present disclosure provides internally cross-linked polypeptides and modified polypeptides that contain a sequence based on a BH4 domain of a BCL-2 family protein that include at least two modified amino acids joined by an internal (intramolecular) cross-link (or staple), wherein the at least two amino acids are separated by 2 to 6 amino acids (e.g., 2, 3, or 6 amino acids). Stabilized peptides herein include stapled and/or stitched peptides.

Amino acids are the building blocks of the peptides herein. The term "amino acid" refers to a molecule containing both an amino group and a carboxyl group. Amino acids include alpha-amino acids and beta-amino acids. Amino acids suitable for inclusion in the peptides disclosed herein include, without limitation, natural alpha-amino acids, such as D- and L-isomers of the 20 common naturally-occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids. Amino acids used in the construction of the internally cross-linked polypeptides and modified polypeptides of the present invention can be prepared by organic synthesis, or obtained by other routes, such as, for example, degradation of or isolation from a natural source.

There are many known unnatural amino acids any of which may be included in the internally cross-linked polypeptides and modified polypeptides of the present invention. See for example, S. Hunt, The Non-Protein Amino Acids: In Chemistry and Biochemistry of the Amino Acids, edited by G C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and /para-substituted phenylalanines (e.g., substituted with —C(=O)C6H5; —CF3; —CN; -halo; —NO2; CH3), disubstituted phenylalanines, substituted tyrosines (e.g., further substituted with -Q=O)C6H5; —CF3; —CN; -halo; —NO2; CH3), and statine. Additionally, amino acids can be derivatized to include amino acid residues that are hydroxylated, phosphorylated, sulfonated, acylated, and glycosylated, to name a few.

A "peptide" or "polypeptide" contains (includes) a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally-occurring protein or peptide. A peptide or polypeptide may be naturally-occurring, recombinant, or synthetic, or any combination thereof "Dipeptide" refers to two covalently linked amino acids.

Exemplary peptides that can be used to generate the internally cross-linked polypeptides described herein can include a sequence (e.g., at least 10, 11, 12, 13, 14, 15, 16, 17, 18, 19, 20, 21, 22, 23, 24, 25, 26, 27, 28, 29, or 30 amino acids, or between 10-30, 15-24, 15-25, 17-25, or 15-22 amino acids) that is at least 70% (e.g., at least 75%, 80%, 85%, 90%, 95%, 96%, 97%, 98%, 99%, or 100%) identical to a BH4 domain of a BCL-2 family protein (e.g., a sequence within any one of SEQ ID NOS: 1-3, 144, 146, 148, 150, 152, and 154) that inherently possess or can be induced to have alpha-helical secondary structure. Additional exemplary peptides that can be used to generate the internally cross-linked polypeptides described herein can contain one or more additional amino acids present in a BCL-2 family protein that are N- and/or C-terminal to the conserved BH4 domain. Additional exemplary peptides that can be used to generate the internally cross-linked polypeptides described herein a one, two, three, or four amino acid N-terminal and/or a one, two, three, of four amino acid C-terminal truncation of the sequence of any one of SEQ ID NOS: 1-3, 144, 146, 148, 150, 152, and 154).

In some instances, the internally cross-linked polypeptides include (e.g., comprise, consist essentially of, or consist of) (i) the amino acid sequence of EIVMKYIHYKLSQ RGYEWDA (SEQ ID NO: 1) or (ii) a sequence containing between one to six amino acid substitutions in the sequence of SEQ ID NO: 1, and where: the side chains of two amino acids separated by two to six (inclusive) (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, or 23) or between 15 to 24 (e.g., 15, 16, 17, 18, 19, 20, 21, 22, 23, or 24) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0W_0X_0$ (SEQ ID NO: 135) wherein:

$A_0$ is Asn, or a conservative amino acid substitution thereof, or any amino acid, $B_0$ is Arg or Cys, or a conservative amino acid substitution thereof, or any amino acid, $C_0$ is Glu or Ala, or a conservative amino acid substitution thereof, or any amino acid, $D_0$ is Ile, Ala, or selenocysteine, or a conservative amino acid substitution thereof, or any amino acid, $E_0$ is Val or Ala, or a conservative amino acid substitution thereof, or any amino acid, $F_0$ is Met, Asp, Asn, Ala, Cys, or selenocysteine, or a conservative amino acid substitution thereof, or any amino acid, $G_0$ is Lys, Ala, Asp, or a conservative amino acid substitution thereof, or any amino acid, $H_0$ is Tyr or Ala, or a conservative amino acid substitution thereof, or any amino acid, $I_0$ is Ile, Ala, or selenocysteine, or a conservative amino acid substitution thereof, or any amino acid, $J_0$ is His, Ala, or selenocysteine, or a conservative amino acid substitution thereof, or any amino acid, $K_0$ is Tyr or Ala, or a conservative amino acid substitution thereof, or any amino acid, $L_0$ is Lys or a conservative amino acid substitution thereof, or any amino acid, $M_0$ is Leu or Ala, or a conservative amino acid substitution thereof, or any amino acid, $N_0$ is Ser or Ala, or a conservative amino acid substitution thereof, or any amino acid, $O_0$ is Gln or a conservative amino acid substitution thereof, or any amino acid, $P_0$ is Arg, Ala, or Glu, or a conservative amino acid substitution thereof, or any amino acid, $Q_0$ is Gly, Ala, or Glu, or a conservative amino acid substitution thereof, or any amino acid, $R_0$ is Tyr, Ala, Arg, or selenocysteine, or a conservative amino acid substitution thereof, or any amino acid, $S_0$ is Glu or a conservative amino acid substitution thereof, or any amino acid, $T_0$ is Trp, Ala, Arg, or selenocysteine, or a conservative amino acid substitution thereof, or any amino acid, $U_0$ is Asp or Ala, or a conservative amino acid substitution thereof, or any amino acid, $V_0$ is Ala or Glu, or a conservative amino acid substitution thereof, or any amino acid, $W_0$ is Gly or Cys, or a conservative amino acid substitution thereof, or any amino acid, and $X_0$ is Asp or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0W_0X_0$ (SEQ ID NO: 135) wherein:

$A_0$ is Asn, or a conservative amino acid substitution thereof, $B_0$ is Arg or Cys, or a conservative amino acid substitution thereof, $C_0$ is Glu or Ala, or a conservative amino acid substitution thereof, $D_0$ is Ile, Ala, or selenocysteine, or a conservative amino acid substitution thereof, $E_0$ is Val or Ala, or a conservative amino acid substitution thereof, $F_0$ is Met, Asp, Asn, Ala, Cys, or selenocysteine, or a conservative amino acid substitution thereof, $G_0$ is Lys, Ala, Asp, or a conservative amino acid substitution thereof, $H_0$ is Tyr or Ala, or a conservative amino acid substitution thereof, $I_0$ is Ile, Ala, or selenocysteine, or a conservative amino acid substitution thereof, $J_0$ is His, Ala, or selenocysteine, or a conservative amino acid substitution thereof, $K_0$ is Tyr or Ala, or a conservative amino acid substitution thereof, $L_0$ is Lys or a conservative amino acid substitution thereof, $M_0$ is Leu or Ala, or a conservative amino acid substitution thereof, $N_0$ is Ser or Ala, or a conservative amino acid substitution thereof, $O_0$ is Gln or a conservative amino acid substitution thereof, $P_0$ is Arg, Ala, or Glu, or a conservative amino acid substitution thereof, $Q_0$ is Gly, Ala, or Glu, or a conservative amino acid substitution thereof, $R_0$ is Tyr, Ala, Arg, or selenocysteine, or a conservative amino acid substitution thereof, $S_0$ is Glu or a conservative amino acid substitution thereof, $T_0$ is Trp, Ala, Arg, or selenocysteine, or a conservative amino acid substitution thereof, $U_0$ is Asp or Ala, or a conservative amino acid substitution thereof, $V_0$ is Ala or Glu, or a conservative amino acid substitution thereof, $W_0$ is Gly or Cys, or a conservative amino acid substitution thereof, and $X_0$ is Asp or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure.

The internally cross-linked polypeptides described herein can also include at least seven (e.g., at least 8, 9, 10, 11, 12, 13, 14, 15, 16, 17, 18, 19, 20, or 22) or 15 to 22 (e.g., 15, 16, 17, 18, 19, 20, 21, or 22) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0$ (SEQ ID NO:135) wherein:

$A_0$ is Asn,
$B_0$ is Arg or Cys,
$C_0$ is Glu or Ala,
$D_0$ is Ile, Ala, or selenocysteine,
$E_0$ is Val or Ala,
$F_0$ is Met, Asp, Asn, Ala, Cys, or selenocysteine,
$G_0$ is Lys, Ala, or Asp,
$H_0$ is Tyr or Ala,
$I_0$ is Ile, Ala, or selenocysteine,
$J_0$ is His, Ala, or selenocysteine,
$K_0$ is Tyr or Ala,
$L_0$ is Lys,
$M_0$ is Leu or Ala,
$N_0$ is Ser or Ala,
$O_0$ is Gln,
$P_0$ is Arg, Ala, or Glu,
$Q_0$ is Gly, Ala, or Glu,
$R_0$ is Tyr, Ala, Arg, or selenocysteine,
$S_0$ is Glu,
$T_0$ is Trp, Ala, Arg, or selenocysteine,
$U_0$ is Asp or Ala,
$V_0$ is Ala or Glu,
$W_0$ is Gly or Cys, and
$X_0$ is Asp, and wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, and $X_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO:1; and/or the polypeptide has a reinforced or stabilized alpha helical secondary structure (e.g., wherein the peptide includes at least one internal crosslink and/or stitch).

In some embodiments, the internally cross-linked polypeptide includes a sequence selected from one of SEQ ID NOs: 1 and 4-50. In some instances, the internally cross-linked polypeptide consists or consists essentially of the sequence of one of SEQ ID NOs: 1 and 4-50. In some instances, internally cross-linked polypeptide includes a sequence that is at least 70% (e.g., at least 80%, 85%, 90%, 95%, 98%, 99%, 99.5%, or 100% identical) identical to any one of SEQ ID NOs: 1 and 4-50 or can include a sequence of one of SEQ ID NOs:1 and 4-50 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of any one of SEQ ID NOs:1 and 4-50 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides include (e.g., comprise, consist essentially of, or consist of): (i) the amino acid sequence of RELVVDFL-SYKLSQK GYSWSQF (SEQ ID NO: 2) or (ii) a sequence containing between one to six (e.g., 1, 2, 3, 4, 5, or 6) amino acid substitutions in the sequence of SEQ ID NO: 2, and wherein: the side chains of two amino acids separated by two to six (e.g., two, three, or six) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, or 21) or between 15 and 22 (e.g., 15, 16, 17, 18, 19, 20, 21, or 22) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0$ (SEQ ID NO: 136) wherein:

$A_0$ is Arg, or a conservative amino acid substitution thereof, or any amino acid, $B_0$ is Glu, or a conservative amino acid substitution thereof, or any amino acid, $C_0$ is Leu or Val, or a conservative amino acid substitution thereof, or any amino acid, $D_0$ is Val or a conservative amino acid substitution thereof, or any amino acid, $E_0$ is Val, Lys, or selenocysteine, or a conservative amino acid substitution thereof, or any amino acid, $F_0$ is Asp or Lys, or a conservative amino acid substitution thereof, or any amino acid, $G_0$ is Phe or a conservative amino acid substitution thereof, or any amino acid, $H_0$ is Leu, Ala, or selenocysteine, or a conservative amino acid substitution thereof, or any amino acid, $I_0$ is Ser or selenocysteine, or a conservative amino acid substitution thereof, or any amino acid, $J_0$ is Tyr or a conservative amino acid substitution thereof, or any amino acid, $K_0$ is Lys or a conservative amino acid substitution thereof, or any amino acid, $L_0$ is Leu or a conservative amino acid substitution thereof, or any amino acid, $M_0$ is Ser or a conservative amino acid substitution thereof, or any amino acid, $N_0$ is Gln or a conservative amino acid substitution thereof, or any amino acid, $O_0$ is Lys or a conservative amino acid substitution thereof, or any amino acid, $P_0$ is Gly or a conservative amino acid substitution thereof, or any amino acid, $Q_0$ is Tyr or selenocysteine, or a conservative amino acid substitution thereof, or any amino acid, $R_0$ is Ser or a conservative amino acid substitution thereof, or any amino acid, $S_0$ is Trp or a conservative amino acid substitution thereof, or any amino acid, $T_0$ is Ser or selenocysteine, or a conservative amino acid substitution thereof, or any amino acid, $U_0$ is Gln or a conservative amino acid substitution thereof, or any amino acid, and $V_0$ is Phe or Asp, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0$ (SEQ ID NO: 136) wherein:

$A_0$ is Arg, or a conservative amino acid substitution thereof, $B_0$ is Glu, or a conservative amino acid substitution thereof, $C_0$ is Leu or Val, or a conservative amino acid substitution thereof, $D_0$ is Val or a conservative amino acid substitution thereof, $E_0$ is Val, Lys, or selenocysteine, or a conservative amino acid substitution thereof, $F_0$ is Asp or Lys, or a conservative amino acid substitution thereof, $G_0$ is Phe or a conservative amino acid substitution thereof, $H_0$ is Leu, Ala, or selenocysteine, or a conservative amino acid substitution thereof, $I_0$ is Ser or selenocysteine, or a conservative amino acid substitution thereof, $J_0$ is Tyr or a conservative amino acid substitution thereof, $K_0$ is Lys or a conservative amino acid substitution thereof, $L_0$ is Leu or a conservative amino acid substitution thereof, $M_0$ is Ser or a conservative amino acid substitution thereof, $N_0$ is Gln or a conservative amino acid substitution thereof, $O_0$ is Lys or a conservative amino acid substitution thereof, $P_0$ is Gly or a conservative amino acid substitution thereof, $Q_0$ is Tyr or selenocysteine, or a conservative amino acid substitution thereof, $R_0$ is Ser or a conservative amino acid substitution thereof, $S_0$ is Trp or a conservative amino acid substitution thereof, $T_0$ is Ser or selenocysteine, or a conservative amino acid substitution thereof, $U_0$ is Gln or a conservative amino acid substitution thereof, and $V_0$ is Phe or Asp, or a conservative amino acid substitution thereof;

wherein the polypeptide has a reinforced or stabilized alpha helical secondary structure (e.g., wherein the side chains of two amino acids separated by two to six (e.g., two, three, or six) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure.

The internally cross-linked polypeptides described herein can also include at least seven (e.g., at least 8, 9, 10, 11, 12, 13, 14, 15, 16, 17, 18, 19, 20, or 21) or between 15 to 22 (e.g., 15, 16, 17, 18, 19, 20, 21, or 22) contiguous amino acids of the amino acid sequence $A_0B_0C_0D_0E_0F_0G_0H_0I_0J_0K_0L_0M_0N_0O_0P_0Q_0R_0S_0T_0U_0V_0$ (SEQ ID NO: 136) wherein:

$A_0$ is Arg, $B_0$ is Glu, $C_0$ is Leu or Val, $D_0$ is Val, $E_0$ is Val, Lys, or selenocysteine, $F_0$ is Asp or Lys, $G_0$ is Phe, $H_0$ is Leu, Ala, or selenocysteine, $I_0$ is Ser or selenocysteine, $J_0$ is Tyr, $K_0$ is Lys, $L_0$ is Leu, $M_0$ is Ser, $N_0$ is Gln, $O_0$ is Lys, $P_0$ is Gly, $Q_0$ is Tyr or selenocysteine, $R_0$ is Ser, $S_0$ is Trp, $T_0$ is Ser or selenocysteine, $U_0$ is Gln, and $V_0$ is Phe or Asp, wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $J_0$, $J_0$, $K_0$, $L_0$, $M_0$, $N_0$, $O_0$, $P_0$, $Q_0$, $R_0$, $S_0$, $T_0$, $U_0$, and $V_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 2; and/or the polypeptide has a reinforced or stabilized alpha helical secondary structure (e.g., wherein the peptide includes at least one internal crosslink and/or stitch).

In some embodiments, the internally cross-linked polypeptide includes a sequence selected from one of SEQ ID NOs: 2 and 51-61. In some instances, the internally cross-linked polypeptide consists or consists essentially of the sequence of one of SEQ ID NOs: 2 and 51-61. In some instances, internally cross-linked polypeptide includes a sequence that is at least 70% (e.g., at least 80%, 85%, 90%, 95%, 98%, 99%, 99.5%, or 100% identical) identical to any one of SEQ ID NOs: 2 and 51-61 or can include a sequence of one of SEQ ID NOs: 2 and 51-61 with one or more (e.g., 1, 2, 3, 4, 5, 6, 7, 8, 9, 10, 11, 12, 13, 14, 15, 16, 17, or 18) conservative amino acid substitutions. In some cases, the internally cross-linked polypeptide has the sequence of any one of SEQ ID NOs: 2 and 51-61 with one or two staples (e.g., one staple between two amino acids separated by between 2 to 6 amino acids (e.g., 2, 3 or 6 amino acids), or two staples each between two amino acids that are separated by between 2 to 6 amino acids (e.g., 2, 3 or 6 amino acids)). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides include (e.g., comprise, consist essentially of, or consist of): (i) the amino acid sequence of ALVADFVGYKL-RQKGYVCGAG (SEQ ID NO: 3) or (ii) a sequence containing between one to six amino acid substitutions in the sequence of SEQ ID NO: 3, and wherein: the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, or 21) or between 15 and 22 (e.g., 15, 16, 17, 18, 19, 20, 21, 22, 23, or 24) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0$ (SEQ ID NO:137) wherein:

$A_0$ is Arg or a conservative amino acid substitution thereof, or any amino acid, $B_0$ is Ala or a conservative amino acid substitution thereof, or any amino acid, $C_0$ is Leu or selenocysteine, or a conservative amino acid substitution thereof, or any amino acid, $D_0$ is Cys or Val, or a conservative amino acid substitution thereof, or any amino acid, $E_0$ is Ala or selenocysteine, or a conservative amino acid substitution thereof, or any amino acid, $F_0$ is Asp or Lys, or a conservative amino acid substitution thereof, or any amino acid, $G_0$ is Phe or a conservative amino acid substitution thereof, or any amino acid, $H_0$ is Val or selenocysteine, or a conservative amino acid substitution thereof, or any amino acid, $I_0$ is Gly or selenocystine, or a conservative amino acid substitution thereof, or any amino acid, $J_0$ is Tyr or a conservative amino acid substitution thereof, or any amino acid, $K_0$ is Lys or a conservative amino acid substitution thereof, or any amino acid, $L_0$ is Leu or Ala, or a conservative amino acid substitution thereof, or any amino acid, $M_0$ is Arg or a conservative amino acid substitution thereof, or any amino acid, $N_0$ is Gln or a conservative amino acid substitution thereof, or any amino acid, $O_0$ is Lys or a conservative amino acid substitution thereof, or any amino acid, $P_0$ is Gly or a conservative amino acid substitution thereof, or any amino acid, $Q_0$ is Tyr or a conservative amino acid substitution thereof, or any amino acid, $R_0$ is Val or a conservative amino acid substitution thereof, or any amino acid, $S_0$ is Cys, Asp, or Asn, or a conservative amino acid substitution thereof, or any amino acid, $T_0$ is Gly or a conservative amino acid substitution thereof, or any amino acid, $U_0$ is Ala or a conservative amino acid substitution thereof, or any amino acid, and $V_0$ is Gly or Asp, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0$ (SEQ ID NO:137) wherein:

$A_0$ is Arg or a conservative amino acid substitution thereof, $B_0$ is Ala or a conservative amino acid substitution thereof, $C_0$ is Leu or selenocysteine, or a conservative amino acid substitution thereof, $D_0$ is Cys or Val, or a conservative amino acid substitution thereof, $E_0$ is Ala or selenocysteine, or a conservative amino acid substitution thereof, $F_0$ is Asp or Lys, or a conservative amino acid substitution thereof, $G_0$ is Phe or a conservative amino acid substitution thereof, $H_0$ is Val or selenocysteine, or a conservative amino acid substitution thereof, $I_0$ is Gly or selenocystine, or a conservative amino acid substitution thereof, $J_0$ is Tyr or a conservative amino acid substitution thereof, $K_0$ is Lys or a conservative amino acid substitution thereof, $L_0$ is Leu or Ala, or a conservative amino acid substitution thereof, $M_0$ is Arg or a conservative amino acid substitution thereof, $N_0$ is Gln or a conservative amino acid substitution thereof, $O_0$ is Lys or a conservative amino acid substitution thereof, $P_0$ is Gly or a conservative amino acid substitution thereof, $Q_0$ is Tyr or a conservative amino acid substitution thereof, $R_0$ is Val or a conservative amino acid substitution thereof, $S_0$ is Cys, Asp, or Asn, or a conservative amino acid substitution thereof, $T_0$ is Gly or a conservative amino acid substitution thereof, $U_0$ is Ala or a conservative amino acid substitution thereof, and $V_0$ is Gly or Asp, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure.

The internally cross-linked polypeptides described herein can also include at least seven (e.g., at least 8, 9, 10, 11, 12, 13, 14, 15, 16, 17, 18, 19, 20, or 21) or between 15 and 22 (e.g., 15, 16, 17, 18, 19, 20, 21, or 22) contiguous amino acids of the amino acid sequence $A_0B_0C_0D_0E_0F_0G_0H_0I_0J_0K_0L_0M_0N_0O_0P_0Q_0R_0S_0T_0U_0V_0$ (SEQ ID NO: 137) wherein:

$A_0$ is Arg,
$B_0$ is Ala,
$C_0$ is Leu or selenocysteine,
$D_0$ is Cys or Val,
$E_0$ is Ala or selenocysteine,
$F_0$ is Asp or Lys,
$G_0$ is Phe,
$H_0$ is Val or selenocysteine,
$I_0$ is Gly or selenocystine,
$J_0$ is Tyr,
$K_0$ is Lys,
$L_0$ is Leu or Ala,
$M_0$ is Arg,
$N_0$ is Gln,
$O_0$ is Lys,
$P_0$ is Gly,
$Q_0$ is Tyr,
$R_0$ is Val,
$S_0$ is Cys, Asp, or Asn,
$T_0$ is Gly,
$U_0$ is Ala, and
$V_0$ is Gly or Asp, wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, or $V_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 3; and/or the polypeptide has a reinforced or stabilized alpha helical secondary structure (e.g., wherein the peptide includes at least one internal crosslink and/or stitch).

In some embodiments, the internally cross-linked polypeptide includes a sequence selected from one of SEQ ID NOs: 3 and 62-71. In some instances, the internally cross-linked polypeptide consists or consists essentially of the sequence of one of SEQ ID NOs: 3 and 62-71. In some instances, internally cross-linked polypeptide includes a sequence that is at least 70% (e.g., at least 80%, 85%, 90%, 95%, 98%, 99%, 99.5%, or 100% identical) identical to any one of SEQ ID NOs: 3 and 62-71 or can include a sequence of any one of SEQ ID NOs: 3 and 62-71 with one or more (e.g., 1, 2, 3, 4, 5, 6, 7, 8, 9, 10, 11, 12, 13, 14, 15, 16, 17, or 18) conservative amino acid substitutions. In some cases, the internally cross-linked polypeptide has the sequence of any one of SEQ ID NOs: 3 and 62-71 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6 amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, 23, 24, 25, or 26) or between 15 to 27 (e.g., 15, 16, 17, 18, 19, 20, 21, 22, 23, 24, 25, 26, or 27) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 143) wherein:

$A_0$ is Thr, or a conservative amino acid substitution thereof, or any amino acid,
$B_0$ is Asp, or a conservative amino acid substitution thereof, or any amino acid,
$C_0$ is Cys, or a conservative amino acid substitution thereof, or any amino acid,
$D_0$ is Glu, or a conservative amino acid substitution thereof, or any amino acid,
$E_0$ is Phe, or a conservative amino acid substitution thereof, or any amino acid,
$F_0$ is Gly, or a conservative amino acid substitution thereof, or any amino acid,
$G_0$ is Tyr, or a conservative amino acid substitution thereof, or any amino acid,
$H_0$ is Ile, or a conservative amino acid substitution thereof, or any amino acid,
$I_0$ is Tyr, or a conservative amino acid substitution thereof, or any amino acid,
$J_0$ is Arg, or a conservative amino acid substitution thereof, or any amino acid,
$K_0$ is Leu, or a conservative amino acid substitution thereof, or any amino acid,
$L_0$ is Ala, or a conservative amino acid substitution thereof, or any amino acid,
$M_0$ is Gln, or a conservative amino acid substitution thereof, or any amino acid,
$N_0$ is Asp, or a conservative amino acid substitution thereof, or any amino acid,
$O_0$ is Tyr, or a conservative amino acid substitution thereof, or any amino acid,
$P_0$ is Leu, or a conservative amino acid substitution thereof, or any amino acid,
$Q_0$ is Gln, or a conservative amino acid substitution thereof, or any amino acid,
$R_0$ is Cys, or a conservative amino acid substitution thereof, or any amino acid,
$S_0$ is Val, or a conservative amino acid substitution thereof, or any amino acid
$T_0$ is Leu, or a conservative amino acid substitution thereof, or any amino acid,
$U_0$ is Gln, or a conservative amino acid substitution thereof, or any amino acid,
$V_0$ is Ile, or a conservative amino acid substitution thereof, or any amino acid,
$W_0$ is Pro, or a conservative amino acid substitution thereof, or any amino acid,
$X_0$ is Gln, or a conservative amino acid substitution thereof, or any amino acid,
$Y_0$ is Pro, or a conservative amino acid substitution thereof, or any amino acid,
$Z_0$ is Gly, or a conservative amino acid substitution thereof, or any amino acid, and
$A'_0$ is Ser, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 143) wherein:

$A_0$ is Thr, or a conservative amino acid substitution thereof, $B_0$ is Asp, or a conservative amino acid substitution thereof, $C_0$ is Cys, or a conservative amino acid substitution thereof, $D_0$ is Glu, or a conservative amino acid substitution thereof, $E_0$ is Phe, or a conservative amino acid substitution thereof, $F_0$ is Gly, or a conservative amino acid substitution thereof, $G_0$ is Tyr, or a conservative amino acid substitution thereof, $H_0$ is Ile, or a conservative amino acid substitution thereof, $I_0$ is Tyr, or a conservative amino acid substitution thereof, $J_0$ is Arg, or a conservative amino acid substitution thereof, $K_0$ is Leu, or a conservative amino acid substitution thereof, $L_0$ is Ala, or a conservative amino acid substitution thereof, $M_0$ is Gln, or a conservative amino acid substitution thereof, $N_0$ is Asp, or a conservative amino acid substitution thereof, $O_0$ is Tyr, or a conservative amino acid substitution thereof, $P_0$ is Leu, or a conservative amino acid substitution thereof, $Q_0$ is Gln, or a conservative amino acid substitution thereof, $R_0$ is Cys, or a conservative amino acid substitution thereof, $S_0$ is Val, or a conservative amino acid substitution thereof, $T_0$ is Leu, or a conservative amino acid substitution thereof, $U_0$ is Gln, or a conservative amino acid substitution thereof, $V_0$ is Ile, or a conservative amino acid substitution thereof, $W_0$ is Pro, or a conservative amino acid substitution thereof, $X_0$ is Gln, or a conservative amino acid substitution thereof, $Y_0$ is Pro, or a conservative amino acid substitution thereof, $Z_0$ is Gly, or a conservative amino acid substitution thereof, and $A'_0$ is Ser, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

The internally cross-linked polypeptides described herein can also include at least seven (e.g., at least 8, 9, 10, 11, 12, 13, 14, 15, 16, 17, 18, 19, 20, 22, 23, 24, 25, or 26) or 15 to 27 (e.g., 15, 16, 17, 18, 19, 20, 21, 22, 23, 24, 25, 26, or 27) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO:144) wherein:

$A_0$ is Thr,
$B_0$ is Asp,
$C_0$ is Cys,
$D_0$ is Glu,
$E_0$ is Phe,
$F_0$ is Gly,
$G_0$ is Tyr,
$H_0$ is Ile,
$I_0$ is Tyr,
$J_0$ is Arg,
$K_0$ is Leu,
$L_0$ is Ala,
$M_0$ is Gln,
$N_0$ is Asp,
$O_0$ is Tyr,
$P_0$ is Leu,
$Q_0$ is Gln,
$R_0$ is Cys,
$S_0$ is Val,
$T_0$ is Leu,
$U_0$ is Gln,
$V_0$ is Ile,
$W_0$ is Pro,
$X_0$ is Gln,
$Y_0$ is Pro,
$Z_0$ is Gly, and
$A'_0$ is Ser;

and wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, $X_0$, $Y_0$, $Z_0$, and $A'_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 144; and/or the polypeptide has a reinforced or stabilized alpha helical secondary structure (e.g., wherein the peptide includes at least one internal crosslink and/or stitch).

In some instances, internally cross-linked polypeptide includes a sequence that is at least 70% (e.g., at least 80%, 85%, 90%, 95%, 98%, 99%, 99.5%, or 100% identical) identical to SEQ ID NO: 144 or can include a sequence of SEQ ID NO:144 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of SEQ ID NO: 143 or 144 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, 23, 24, 25, or 26) or between 15 to 27 (e.g., 15, 16, 17, 18, 19, 20, 21, 22, 23, 24, 25, 26, or 27) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 145) wherein:

$A_0$ is Glu, or a conservative amino acid substitution thereof, or any amino acid, $B_0$ is Asp, or a conservative amino acid substitution thereof, or any amino acid, $C_0$ is Glu, or a conservative amino acid substitution thereof, or any amino acid, $D_0$ is Leu, or a conservative amino acid substitution thereof, or any amino acid, $E_0$ is Tyr, or a conservative amino acid substitution thereof, or any amino acid, $F_0$ is Arg, or a conservative amino acid substitution thereof, or any amino acid, $G_0$ is Gln, or a conservative amino acid substitution thereof, or any amino acid, $H_0$ is Ser, or a conservative amino acid substitution thereof, or any amino acid, $I_0$ is Leu, or a conservative amino acid substitution thereof, or any amino acid, $J_0$ is Glu, or a conservative amino acid substitution thereof, or any amino acid, $K_0$ is Ile, or a conservative amino acid substitution thereof, or any amino acid, $L_0$ is Ile, or a conservative amino acid substitution thereof, or any amino acid, $M_0$ is Ser, or a conservative amino acid substitution thereof, or any amino acid, $N_0$ is Arg, or a conservative amino acid substitution thereof, or any amino acid, $O_0$ is Tyr, or a conservative amino acid substitution thereof, or any amino acid, $P_0$ is Leu, or a conservative amino acid substitution thereof, or any amino acid, $Q_0$ is Arg, or a conservative amino acid substitution thereof, or any amino acid, $R_0$ is Glu, or a conservative amino acid substitution thereof, or any amino acid, $S_0$ is Gln, or a conservative amino acid substitution thereof, or any amino acid, $T_0$ is Ala, or a conservative amino acid substitution thereof, or any amino acid, $U_0$ is Thr, or a conservative amino acid substitution thereof, or any amino acid, $V_0$ is Gly, or a conservative amino acid substitution thereof, or any amino acid, $W_0$ is Ala, or a conservative amino acid substitution thereof, or any amino acid, $X_0$ is Lys, or a conservative amino acid substitution thereof, or any amino acid, $Y_0$ is Pro, or a conservative amino acid substitution thereof, or any amino acid, $Z_0$ is Met, or a conservative amino acid substitution thereof, or any amino acid, and $A'_0$ is Gly, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 145) wherein:

$A_0$ is Glu, or a conservative amino acid substitution thereof, $B_0$ is Asp, or a conservative amino acid substitution thereof, $C_0$ is Glu, or a conservative amino acid substitution thereof, $D_0$ is Leu, or a conservative amino acid substitution thereof, $E_0$ is Tyr, or a conservative amino acid substitution thereof, $F_0$ is Arg, or a conservative amino acid substitution thereof, $G_0$ is Gln, or a conservative amino acid substitution thereof, $H_0$ is Ser, or a conservative amino acid substitution thereof, $I_0$ is Leu, or a conservative amino acid substitution thereof, $J_0$ is Glu, or a conservative amino acid substitution thereof, $K_0$ is Ile, or a conservative amino acid substitution thereof, $L_0$ is Ile, or a conservative amino acid substitution thereof, $M_0$ is Ser, or a conservative amino acid substitution thereof, $N_0$ is Arg, or a conservative amino acid substitution thereof, $O_0$ is Tyr, or a conservative amino acid substitution thereof, $P_0$ is Leu, or a conservative amino acid substitution thereof, $Q_0$ is Arg, or a conservative amino acid substitution thereof, $R_0$ is Glu, or a conservative amino acid substitution thereof, $S_0$ is Gln, or a conservative amino acid substitution thereof, $T_0$ is Ala, or a conservative amino acid substitution thereof, $U_0$ is Thr, or a conservative amino acid substitution thereof, $V_0$ is Gly, or a conservative amino acid substitution thereof, $W_0$ is Ala, or a conservative amino acid substitution thereof, $X_0$ is Lys, or a conservative amino acid substitution thereof, $Y_0$ is Pro, or a conservative amino acid substitution thereof, $Z_0$ is Met, or a conservative amino acid substitution thereof, and $A'_0$ is Gly, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

The internally cross-linked polypeptides described herein can also include at least seven (e.g., at least 8, 9, 10, 11, 12, 13, 14, 15, 16, 17, 18, 19, 20, 22, 23, 24, 25, or 26) or 15 to 27 (e.g., 15, 16, 17, 18, 19, 20, 21, 22, 23, 24, 25, 26, or 27) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO:146) wherein:

$A_0$ is Glu,
$B_0$ is Asp,
$C_0$ is Glu,
$D_0$ is Leu,
$E_0$ is Tyr,
$F_0$ is Arg,
$G_0$ is Gln,
$H_0$ is Ser,
$I_0$ is Leu,
$J_0$ is Glu,
$K_0$ is Ile,
$L_0$ is Ile,
$M_0$ is Ser,
$N_0$ is Arg,
$O_0$ is Tyr,
$P_0$ is Leu,
$Q_0$ is Arg,
$R_0$ is Glu,
$S_0$ is Gln,
$T_0$ is Ala,
$U_0$ is Thr,
$V_0$ is Gly,
$W_0$ is Ala,
$X_0$ is Lys,
$Y_0$ is Pro,
$Z_0$ is Met, and
$A'_0$ is Gly; and wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, $X_0$, $Y_0$, $Z_0$, and $A'_0$ are replaced by a conservative amino acid substitution that does not alter the binding face of the peptide; the polypeptide contains a sequence that is at least 80% (e.g., 80%, 85%, 90%, 95%, 98%, 99%, 99.5%, or 100%) identical to the sequence of SEQ ID NO: 146; and/or the polypeptide has a reinforced or stabilized alpha helical secondary structure (e.g., wherein the peptide includes at least one internal crosslink and/or stitch).

In some instances, internally cross-linked polypeptide includes a sequence that is at least 70% (e.g., at least 80%, 85%, 90%, 95%, 98%, 99%, 99.5%, or 100% identical) identical to SEQ ID NO: 146 or can include a sequence of SEQ ID NO:146 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of SEQ ID NO: 145 or 146 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, 23, 24, or 25) or between 15 to 26 (e.g., 15, 16, 17, 18, 19, 20, 21, 22, 23, 24, 25, or 26) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0$ (SEQ ID NO: 147) wherein:

$A_0$ is Leu, or a conservative amino acid substitution thereof, or any amino acid,
$B_0$ is Val, or a conservative amino acid substitution thereof, or any amino acid,
$C_0$ is Ala, or a conservative amino acid substitution thereof, or any amino acid,
$D_0$ is Gln, or a conservative amino acid substitution thereof, or any amino acid,
$E_0$ is Ala, or a conservative amino acid substitution thereof, or any amino acid,
$F_0$ is Lys, or a conservative amino acid substitution thereof, or any amino acid,
$G_0$ is Ala, or a conservative amino acid substitution thereof, or any amino acid,
$H_0$ is Leu, or a conservative amino acid substitution thereof, or any amino acid,
$I_0$ is Gly, or a conservative amino acid substitution thereof, or any amino acid,
$J_0$ is Arg, or a conservative amino acid substitution thereof, or any amino acid,
$K_0$ is Glu or a conservative amino acid substitution thereof, or any amino acid,
$L_0$ is Tyr, or a conservative amino acid substitution thereof, or any amino acid,
$M_0$ is Val, or a conservative amino acid substitution thereof, or any amino acid,
$N_0$ is His, or a conservative amino acid substitution thereof, or any amino acid,
$O_0$ is Ala, or a conservative amino acid substitution thereof, or any amino acid,
$P_0$ is Arg, or a conservative amino acid substitution thereof, or any amino acid,
$Q_0$ is Leu, or a conservative amino acid substitution thereof, or any amino acid,
$R_0$ is Leu, or a conservative amino acid substitution thereof, or any amino acid,
$S_0$ is Arg, or a conservative amino acid substitution thereof, or any amino acid,
$T_0$ is Ala, or a conservative amino acid substitution thereof, or any amino acid,
$U_0$ is Gly, or a conservative amino acid substitution thereof, or any amino acid,
$V_0$ is Leu, or a conservative amino acid substitution thereof, or any amino acid,
$W_0$ is Ser, or a conservative amino acid substitution thereof, or any amino acid,
$X_0$ is Trp, or a conservative amino acid substitution thereof, or any amino acid,
$Y_0$ is Ser, or a conservative amino acid substitution thereof, or any amino acid, and
$Z_0$ is Ala, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0$ (SEQ ID NO: 147) wherein:

$A_0$ is Leu, or a conservative amino acid substitution thereof,
$B_0$ is Val, or a conservative amino acid substitution thereof,
$C_0$ is Ala, or a conservative amino acid substitution thereof, $D_0$ is Gln, or a conservative amino acid substitution thereof, $E_0$ is Ala, or a conservative amino acid substitution thereof, $F_0$ is Lys, or a conservative amino acid substitution thereof, $G_0$ is Ala, or a conservative amino acid substitution thereof, $H_0$ is Leu, or a conservative amino acid substitution thereof, $I_0$ is Gly, or a conservative amino acid substitution thereof, $J_0$ is Arg, or a conservative amino acid substitution thereof, $K_0$ is Glu or a conservative amino acid substitution thereof, $L_0$ is Tyr, or a conservative amino acid substitution thereof, $M_0$ is Val, or a conservative amino acid substitution thereof, $N_0$ is His, or a conservative amino acid substitution thereof, $O_0$ is Ala, or a conservative amino acid substitution thereof, $P_0$ is Arg, or a conservative amino acid substitution thereof, $Q_0$ is Leu, or a conservative amino acid substitution thereof, $R_0$ is Leu, or a conservative amino acid substitution thereof, $S_0$ is Arg, or a conservative amino acid substitution thereof, $T_0$ is Ala, or a conservative amino acid substitution thereof, $U_0$ is Gly, or a conservative amino acid substitution thereof, $V_0$ is Leu, or a conservative amino acid substitution thereof, $W_0$ is Ser, or a conservative amino acid substitution thereof, $X_0$ is Trp, or a conservative amino acid substitution thereof, $Y_0$ is Ser, or a conservative amino acid substitution thereof, and $Z_0$ is Ala, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

The internally cross-linked polypeptides described herein can also include at least seven (e.g., at least 8, 9, 10, 11, 12, 13, 14, 15, 16, 17, 18, 19, 20, 22, 23, 24, or 25) or 15 to 26 (e.g., 15, 16, 17, 18, 19, 20, 21, 22, 23, 24, 25, or 26) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0Y_0Z_0$ (SEQ ID NO:148) wherein:

$A_0$ is Leu,
$B_0$ is Val,
$C_0$ is Ala,
$D_0$ is Gln,
$E_0$ is Ala,
$F_0$ is Lys,
$G_0$ is Ala,
$H_0$ is Leu,
$I_0$ is Gly,
$J_0$ is Arg,
$K_0$ is Glu,
$L_0$ is Tyr,
$M_0$ is Val,
$N_0$ is His,
$O_0$ is Ala,
$P_0$ is Arg,
$Q_0$ is Leu,
$R_0$ is Leu,
$S_0$ is Arg,
$T_0$ is Ala,
$U_0$ is Gly,
$V_0$ is Leu,
$W_0$ is Ser,
$X_0$ is Trp,
$Y_0$ is Ser, and
$Z_0$ is Ala, wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $J_0$, $J_0$, $K_0$, $L_0$, $M_0$, $N_0$, $O_0$, $P_0$, $Q_0$, $R_0$, $S_0$, $T_0$, $U_0$, $V_0$, $W_0$, $X_0$, $Y_0$, and $Z_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 148; and/or the polypeptide has a reinforced or stabilized alpha helical secondary structure (e.g., wherein the peptide includes at least one internal crosslink and/or stitch).

In some instances, internally cross-linked polypeptide includes a sequence that is at least 70% (e.g., at least 80%, 85%, 90%, 95%, 98%, 99%, 99.5%, or 100% identical) identical to SEQ ID NO: 148 or can include a sequence of SEQ ID NO:148 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of SEQ ID NO: 147 or 148 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, 23, 24, 25, or 26) or between 15 to 27 (e.g., 15, 16, 17, 18, 19, 20, 21, 22, 23, 24, 25, 26, or 27) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 149) wherein:

$A_0$ is Ser, or a conservative amino acid substitution thereof, or any amino acid, $B_0$ is Glu, or a conservative amino acid substitution thereof, or any amino acid, $C_0$ is Gln, or a conservative amino acid substitution thereof, or any amino acid, $D_0$ is Ile, or a conservative amino acid substitution thereof, or any amino acid, $E_0$ is Met, or a conservative amino acid substitution thereof, or any amino acid, $F_0$ is Lys, or a conservative amino acid substitution thereof, or any amino acid, $G_0$ is Thr, or a conservative amino acid substitution thereof, or any amino acid, $H_0$ is Gly, or a conservative amino acid substitution thereof, or any amino acid, $I_0$ is Ala, or a conservative amino acid substitution thereof, or any amino acid, $J_0$ is Leu, or a conservative amino acid substitution thereof, or any amino acid, $K_0$ is Leu, or a conservative amino acid substitution thereof, or any amino acid, $L_0$ is Leu, or a conservative amino acid substitution thereof, or any amino acid, $M_0$ is Gln, or a conservative amino acid substitution thereof, or any amino acid, $N_0$ is Gly, or a conservative amino acid substitution thereof, or any amino acid, $O_0$ is Phe, or a conservative amino acid substitution thereof, or any amino acid, $P_0$ is Ile, or a conservative amino acid substitution thereof, or any amino acid, $Q_0$ is Gln, or a conservative amino acid substitution thereof, or any amino acid, $R_0$ is Asp, or a conservative amino acid substitution thereof, or any amino acid, $S_0$ is Arg, or a conservative amino acid substitution thereof, or any amino acid, $T_0$ is Ala, or a conservative amino acid substitution thereof, or any amino acid, $U_0$ is Gly, or a conservative amino acid substitution thereof, or any amino acid, $V_0$ is Arg, or a conservative amino acid substitution thereof, or any amino acid, $W_0$ is Met, or a conservative amino acid substitution thereof, or any amino acid, $X_0$ is Gly, or a conservative amino acid substitution thereof, or any amino acid, $Y_0$ is Gly, or a conservative amino acid substitution thereof, or any amino acid, $Z_0$ is Glu, or a conservative amino acid substitution thereof, or any amino acid, and $N_0$ is Ala, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 149) wherein:

$A_0$ is Ser, or a conservative amino acid substitution thereof, $B_0$ is Glu, or a conservative amino acid substitution thereof, $C_0$ is Gln, or a conservative amino acid substitution thereof, $D_0$ is Ile, or a conservative amino acid substitution thereof, $E_0$ is Met, or a conservative amino acid substitution thereof, $F_0$ is Lys, or a conservative amino acid substitution thereof, $G_0$ is Thr, or a conservative amino acid substitution thereof, $H_0$ is Gly, or a conservative amino acid substitution thereof, $I_0$ is Ala, or a conservative amino acid substitution thereof, $J_0$ is Leu, or a conservative amino acid substitution thereof, $K_0$ is Leu, or a conservative amino acid substitution thereof, $L_0$ is Leu, or a conservative amino acid substitution thereof, $M_0$ is Gln, or a conservative amino acid substitution thereof, $N_0$ is Gly, or a conservative amino acid substitution thereof, $O_0$ is Phe, or a conservative amino acid substitution thereof, $P_0$ is Ile, or a conservative amino acid substitution thereof, $Q_0$ is Gln, or a conservative amino acid substitution thereof, $R_0$ is Asp, or a conservative amino acid substitution thereof, $S_0$ is Arg, or a conservative amino acid substitution thereof, $T_0$ is Ala, or a conservative amino acid substitution thereof, $U_0$ is Gly, or a conservative amino acid substitution thereof, $V_0$ is Arg, or a conservative amino acid substitution thereof, $W_0$ is Met, or a conservative amino acid substitution thereof, $X_0$ is Gly, or a conservative amino acid substitution thereof, $Y_0$ is Gly, or a conservative amino acid substitution thereof, $Z_0$ is Glu, or a conservative amino acid substitution thereof, and $A'_0$ is Ala, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

The internally cross-linked polypeptides described herein can also include at least seven (e.g., at least 8, 9, 10, 11, 12, 13, 14, 15, 16, 17, 18, 19, 20, 22, 23, 24, 25, or 26) or 15 to 27 (e.g., 15, 16, 17, 18, 19, 20, 21, 22, 23, 24, 25, 26, or 27) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 150) wherein:

$A_0$ is Ser, $B_0$ is Glu, $C_0$ is Gln, $D_0$ is Ile,
$E_0$ is Met,
$F_0$ is Lys,
$G_0$ is Thr,
$H_0$ is Gly,
$I_0$ is Ala,
$J_0$ is Leu,
$K_0$ is Leu,
$L_0$ is Leu,
$M_0$ is Gln,
$N_0$ is Gly,
$O_0$ is Phe,
$P_0$ is Ile,
$Q_0$ is Gln,
$R_0$ is Asp,
$S_0$ is Arg,
$T_0$ is Ala,
$U_0$ is Gly,
$V_0$ is Arg,
$W_0$ is Met,
$X_0$ is Gly,
$Y_0$ is Gly,
$Z_0$ is Glu, and
$A'_0$ is Ala;
wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, $X_0$, $Y_0$, $Z_0$, and $A'_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 150; and/or the polypeptide has a reinforced or stabilized alpha helical secondary structure (e.g., wherein the peptide includes at least one internal crosslink and/or stitch).

In some instances, internally cross-linked polypeptide includes a sequence that is at least 70% (e.g., at least 80%, 85%, 90%, 95%, 98%, 99%, 99.5%, or 100% identical) identical to SEQ ID NO: 150 or can include a sequence of SEQ ID NO:150 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of SEQ ID NO: 149 or 150 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, 23, 24, 25, or 26) or between 15 to 27 (e.g., 15, 16, 17, 18, 19, 20, 21, 22, 23, 24, 25, 26, or 27) contiguous amino acids of:

(i) the amino acid sequence of $A_0B_0C_0D_0E_0F_0G_0H_0I_0J_0$ $K_0L_0M_0N_0O_0P_0Q_0R_0S_0T_0U_0V_0W_0X_0Y_0Z_0A'_0$ (SEQ ID NO: 151) wherein:

$A_0$ is Val, or a conservative amino acid substitution thereof, or any amino acid, $B_0$ is Ala, or a conservative amino acid substitution thereof, or any amino acid, $C_0$ is Gln, or a conservative amino acid substitution thereof, or any amino acid, $D_0$ is Asp, or a conservative amino acid substitution thereof, or any amino acid, $E_0$ is Thr, or a conservative amino acid substitution thereof, or any amino acid, $F_0$ is Glu, or a conservative amino acid substitution thereof, or any amino acid, $G_0$ is Glu, or a conservative amino acid substitution thereof, or any amino acid, $H_0$ is Val, or a conservative amino acid substitution thereof, or any amino acid, $I_0$ is Phe, or a conservative amino acid substitution thereof, or any amino acid, $J_0$ is Arg, or a conservative amino acid substitution thereof, or any amino acid, $K_0$ is Ser, or a conservative amino acid substitution thereof, or any amino acid, $L_0$ is Tyr, or a conservative amino acid substitution thereof, or any amino acid, $M_0$ is Val, or a conservative amino acid substitution thereof, or any amino acid, $N_0$ is Phe, or a conservative amino acid substitution thereof, or any amino acid, $O_0$ is Tyr, or a conservative amino acid substitution thereof, or any amino acid, $P_0$ is Arg, or a conservative amino acid substitution thereof, or any amino acid, $Q_0$ is His, or a conservative amino acid substitution thereof, or any amino acid, $R_0$ is Gln, or a conservative amino acid substitution thereof, or any amino acid, $S_0$ is Gln, or a conservative amino acid substitution thereof, or any amino acid, $T_0$ is Glu, or a conservative amino acid substitution thereof, or any amino acid, $U_0$ is Gln, or a conservative amino acid substitution thereof, or any amino acid, $V_0$ is Glu, or a conservative amino acid substitution thereof, or any amino acid, $W_0$ is Ala, or a conservative amino acid substitution thereof, or any amino acid, $X_0$ is Glu, or a conservative amino acid substitution thereof, or any amino acid, $Y_0$ is Gly, or a conservative amino acid substitution thereof, or any amino acid, $Z_0$ is Val, or a conservative amino acid substitution thereof, or any amino acid, and $A'_0$ is Ala, or a conservative amino acid substitution thereof, or any amino acid; or (ii) the amino acid sequence of $A_0B_0C_0D_0E_0F_0G_0$ $H_0I_0J_0K_0L_0M_0N_0O_0P_0Q_0R_0S_0T_0U_0V_0W_0X_0Y_0Z_0A'_0$ (SEQ ID NO: 151) wherein:

$A_0$ is Val, or a conservative amino acid substitution thereof, $B_0$ is Ala, or a conservative amino acid substitution thereof, $C_0$ is Gln, or a conservative amino acid substitution thereof, $D_0$ is Asp, or a conservative amino acid substitution thereof, $E_0$ is Thr, or a conservative amino acid substitution thereof, $F_0$ is Glu, or a conservative amino acid substitution thereof, $G_0$ is Glu, or a conservative amino acid substitution thereof, $H_0$ is Val, or a conservative amino acid substitution thereof, $I_0$ is Phe, or a conservative amino acid substitution thereof, $J_0$ is Arg, or a conservative amino acid substitution thereof, $K_0$ is Ser, or a conservative amino acid substitution thereof, $L_0$ is Tyr, or a conservative amino acid substitution thereof, $M_0$ is Val, or a conservative amino acid substitution thereof, $N_0$ is Phe, or a conservative amino acid substitution thereof, $O_0$ is Tyr, or a conservative amino acid substitution thereof, $P_0$ is Arg, or a conservative amino acid substitution thereof, $Q_0$ is His, or a conservative amino acid substitution thereof, $R_0$ is Gln, or a conservative amino acid substitution thereof, $S_0$ is Gln, or a conservative amino acid substitution thereof, $T_0$ is Glu, or a conservative amino acid substitution thereof, $U_0$ is Gln, or a conservative amino acid substitution thereof, $V_0$ is Glu, or a conservative amino acid substitution thereof, $W_0$ is Ala, or a conservative amino acid substitution thereof, $X_0$ is Glu, or a conservative amino acid substitution thereof, $Y_0$ is Gly, or a conservative amino acid substitution thereof, $Z_0$ is Val, or a conservative amino acid substitution thereof, and $A'_0$ is Ala, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

The internally cross-linked polypeptides described herein can also include at least seven (e.g., at least 8, 9, 10, 11, 12, 13, 14, 15, 16, 17, 18, 19, 20, 22, 23, 24, 25, or 26) or 15 to 27 (e.g., 15, 16, 17, 18, 19, 20, 21, 22, 23, 24, 25, 26, or 27) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 152) wherein:

$A_0$ is Val,
$B_0$ is Ala,
$C_0$ is Gln,
$D_0$ is Asp,
$E_0$ is Thr,
$F_0$ is Glu,
$G_0$ is Glu,
$H_0$ is Val,
$I_0$ is Phe,
$J_0$ is Arg,
$K_0$ is Ser,
$L_0$ is Tyr,
$M_0$ is Val,
$N_0$ is Phe,
$O_0$ is Tyr,
$P_0$ is Arg,
$Q_0$ is His,
$R_0$ is Gln,
$S_0$ is Gln,
$T_0$ is Glu,
$U_0$ is Gln,
$V_0$ is Glu,
$W_0$ is Ala,
$X_0$ is Glu,
$Y_0$ is Gly,
$Z_0$ is Val, and
$A'_0$ is Ala;

wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, $X_0$, $Y_0$, $Z_0$, and $A'_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 152; and/or the polypeptide has a reinforced or stabilized alpha helical secondary structure (e.g., wherein the peptide includes at least one internal crosslink and/or stitch).

In some instances, internally cross-linked polypeptide includes a sequence that is at least 70% (e.g., at least 80%, 85%, 90%, 95%, 98%, 99%, 99.5%, or 100% identical) identical to SEQ ID NO: 152 or can include a sequence of SEQ ID NO:152 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of SEQ ID NO: 151 or 152 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

In some instances, the internally cross-linked polypeptides can include (e.g., comprise, consist essentially of, or consist of) at least seven (e.g., at least 8, 9, 10, 11, 12, 13, 14, 15, 16, 17, 18, 19, 20, 21, 22, 23, 24, 25, or 26) or between 15 to 27 (e.g., 15, 16, 17, 18, 19, 20, 21, 22, 23, 24, 25, 26, or 27) contiguous amino acids of:

(i) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 153) wherein:

$A_0$ is Arg, or a conservative amino acid substitution thereof, or any amino acid, $B_0$ is Glu, or a conservative amino acid substitution thereof, or any amino acid, $C_0$ is Arg, or a conservative amino acid substitution thereof, or any amino acid, $D_0$ is Thr, or a conservative amino acid substitution thereof, or any amino acid, $E_0$ is Glu, or a conservative amino acid substitution thereof, or any amino acid,
$F_0$ is Leu, or a conservative amino acid substitution thereof, or any amino acid,
$G_0$ is Leu, or a conservative amino acid substitution thereof, or any amino acid,
$H_0$ is Leu, or a conservative amino acid substitution thereof, or any amino acid,
$I_0$ is Ala, or a conservative amino acid substitution thereof, or any amino acid,
$J_0$ is Asp, or a conservative amino acid substitution thereof, or any amino acid,
$K_0$ is Tyr, or a conservative amino acid substitution thereof, or any amino acid,
$L_0$ is Leu, or a conservative amino acid substitution thereof, or any amino acid,
$M_0$ is Gly, or a conservative amino acid substitution thereof, or any amino acid,
$N_0$ is Tyr, or a conservative amino acid substitution thereof, or any amino acid,
$O_0$ is Cys, or a conservative amino acid substitution thereof, or any amino acid,
$P_0$ is Ala, or a conservative amino acid substitution thereof, or any amino acid,
$Q_0$ is Arg, or a conservative amino acid substitution thereof, or any amino acid,
$R_0$ is Glu, or a conservative amino acid substitution thereof, or any amino acid,
$S_0$ is Pro, or a conservative amino acid substitution thereof, or any amino acid,
$T_0$ is Gly, or a conservative amino acid substitution thereof, or any amino acid,
$U_0$ is Thr, or a conservative amino acid substitution thereof, or any amino acid,
$V_0$ is Pro, or a conservative amino acid substitution thereof, or any amino acid,
$W_0$ is Glu, or a conservative amino acid substitution thereof, or any amino acid,
$X_0$ is Pro, or a conservative amino acid substitution thereof, or any amino acid,
$Y_0$ is Ala, or a conservative amino acid substitution thereof, or any amino acid,
$Z_0$ is Pro, or a conservative amino acid substitution thereof, or any amino acid, and
$A'_0$ is Ser, or a conservative amino acid substitution thereof, or any amino acid; or (ii) the amino acid sequence of $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 153) wherein:
$A_0$ is Arg, or a conservative amino acid substitution thereof,
$B_0$ is Glu, or a conservative amino acid substitution thereof,
$C_0$ is Arg, or a conservative amino acid substitution thereof,
$D_0$ is Thr, or a conservative amino acid substitution thereof,
$E_0$ is Glu, or a conservative amino acid substitution thereof,
$F_0$ is Leu, or a conservative amino acid substitution thereof,
$G_0$ is Leu, or a conservative amino acid substitution thereof,
$H_0$ is Leu, or a conservative amino acid substitution thereof,
$I_0$ is Ala, or a conservative amino acid substitution thereof,
$J_0$ is Asp, or a conservative amino acid substitution thereof,
$K_0$ is Tyr, or a conservative amino acid substitution thereof,
$L_0$ is Leu, or a conservative amino acid substitution thereof,
$M_0$ is Gly, or a conservative amino acid substitution thereof,
$N_0$ is Tyr, or a conservative amino acid substitution thereof,
$O_0$ is Cys, or a conservative amino acid substitution thereof,
$P_0$ is Ala, or a conservative amino acid substitution thereof,
$Q_0$ is Arg, or a conservative amino acid substitution thereof,
$R_0$ is Glu, or a conservative amino acid substitution thereof,
$S_0$ is Pro, or a conservative amino acid substitution thereof,
$T_0$ is Gly, or a conservative amino acid substitution thereof,
$U_0$ is Thr, or a conservative amino acid substitution thereof,
$V_0$ is Pro, or a conservative amino acid substitution thereof,
$W_0$ is Glu, or a conservative amino acid substitution thereof,
$X_0$ is Pro, or a conservative amino acid substitution thereof,
$Y_0$ is Ala, or a conservative amino acid substitution thereof,
$Z_0$ is Pro, or a conservative amino acid substitution thereof, and
$A'_0$ is Ser, or a conservative amino acid substitution thereof;

wherein the polypeptide has a reinforced or stabilized alpha helical secondary structure (e.g., wherein the side chains of two amino acids separated by two to six (e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches). In some instances, the peptide has or can be induced to have alpha-helical secondary structure. In some cases the internally stapled or stitched polypeptide includes a targeting moiety or a moiety that facilitates cell entry (e.g., 2, 3, 4, 5, 6, 7, 8 or 9 contiguous Arg) at the amino or carboxy terminus.

The internally cross-linked polypeptides described herein can also include at least seven (e.g., at least 8, 9, 10, 11, 12, 13, 14, 15, 16, 17, 18, 19, 20, 22, 23, 24, 25, or 26) or 15 to 27 (e.g., 15, 16, 17, 18, 19, 20, 21, 22, 23, 24, 25, 26, or 27) contiguous amino acids of the amino acid sequence $A_0B_0C_0D_0E_0F_0G_0H_0I_0J_0K_0L_0M_0N_0O_0P_0Q_0R_0S_0T_0U_0V_0W_0X_0Y_0Z_0A'_0$ (SEQ ID NO: 154) wherein:

$A_0$ is Arg, $B_0$ is Glu, $C_0$ is Arg, $D_0$ is Thr, $E_0$ is Glu, $F_0$ is Leu, $G_0$ is Leu, $H_0$ is Leu, $I_0$ is Ala,
$J_0$ is Asp,
$K_0$ is Tyr,
$L_0$ is Leu,
$M_0$ is Gly,
$N_0$ is Tyr,
$O_0$ is Cys,
$P_0$ is Ala,
$Q_0$ is Arg,
$R_0$ is Glu,
$S_0$ is Pro,
$T_0$ is Gly,
$U_0$ is Thr,
$V_0$ is Pro,
$W_0$ is Glu,
$X_0$ is Pro,
$Y_0$ is Ala,
$Z_0$ is Pro, and
$A'_0$ is Ser;
wherein: one or more (e.g., 1, 2, 3, 4, 5, 6, 7, 8, 9, 10, 11, 12, 13, 14, 15, 16, 17, or 18) of $A_0$, $B_0$, $C_0$, $D_0$, $E_0$, $F_0$, $G_0$, $H_0$, $E_0$, $F_0$, $G_0$, $H_0$, $I_0$, $J_0$, $K_0$, $L_0$, $M_0$, $N_0$, $O_0$, $P_0$, $Q_0$, $R_0$, $S_0$, $T_0$, $U_0$, $V_0$, $W_0$, $X_0$, $Y_0$, $Z_0$, and $A'_0$ are replaced by a conservative amino acid substitution that does not alter the binding face of the peptide;

the polypeptide contains a sequence that is at least 80% (e.g., 80%, 85%, 90%, 95%, 98%, 99%, 99.5%, or 100%) identical to the sequence of SEQ ID NO: 154; and/or the polypeptide has a reinforced or stabilized alpha helical secondary structure (e.g., wherein the peptide includes at least one internal crosslink and/or stitch).

In some instances, internally cross-linked polypeptide includes a sequence that is at least 70% (e.g., at least 80%, 85%, 90%, 95%, 98%, 99%, 99.5%, or 100% identical) identical to SEQ ID NO: 152 or can include a sequence of SEQ ID NO:154 with one or more (e.g., 1, 2, 3, 4, 5, 6, 7, 8, 9, 10, 11, 12, 13, 14, 15, 16, 17, 18) conservative amino acid substitutions. In some cases, the internally cross-linked polypeptide has the sequence of SEQ ID NO: 153 or 154 with one or two staples (e.g., one staple between two amino acids separated by between 2 to 6 (e.g., 2, 3, or 6) amino acids, or two staples each between two amino acids that are separated by between 2 to 6 (e.g., 2, 3, or 6) amino acids). In addition, 1, 2, 3, 4, 5, 6, 7, 8, 9, 10, 11, 12, 13, 14, 15, 16, 17, or 18 of the amino acids (whose side chains are not replaced with a staple) can, in this internally cross-linked polypeptide can be replaced by a conservative substitution.

The "interacting face" of the internally cross-linked polypeptides described herein includes those amino acid residues of the alpha helix that interact (e.g., interact specifically or bind specifically) with a BAX protein. In the context of the amino acids in the interacting face of the internally cross-linked polypeptides or modified polypeptides, a conservative amino acid substitution is an amino acid substitution that does not alter the chemical makeup of the interacting face of the peptide.

A conservative amino acid substitution is an amino acid substitution that does not reduce (e.g., substantially reduce) binding of the internally cross-linked polypeptide or modified polypeptide to its target protein, e.g., BAX protein, and may, in some circumstances, improve binding activity. Methods for detecting any reduction in binding can include comparing binding affinity following conservative amino acid substitution, wherein any amino acid substitution that reduces (e.g., substantially reduces) binding are not conservative amino acid substitutions. In some embodiments, substantially reduced binding can include binding that is 10% or less, 20% or less, 30% or less, 40% or less, 50% or less, 60% or less, 70% or less, 80% or less, 90% or less, 95% or less, 98% or less, 99% or less, or 100% less than binding of the unsubstituted internally cross-linked polypeptide or modified polypeptide to its target protein, e.g., a BAX protein. Methods for assessing interaction between an internally cross-linked polypeptide or modified polypeptide and a target protein, e.g., a BAX protein, are disclosed herein. Methods for identifying the interactive face of a peptide are known in the art (see, e.g., Broglia et al., *Protein Sci.*, 14(10):2668-81, 2005; Hammond et al., *J. Pharm. Sci.*, 98(1):4589-603, 2009; Ng et al., *J. Phys. Chem. B.*, 111(50): 13886-93, 2007; and Bird et al., *Proc. Natl. Acad. Sci. U.S.A.* 197:14093, 2010).

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), beta-branched side chains (e.g., threonine, valine, and isoleucine) and aromatic side chains (e.g., tyrosine, phenylalanine, tryptophan, and histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (*Nucleic Acids Res.* 25:3389-3402, 1997).

Figure 24A:
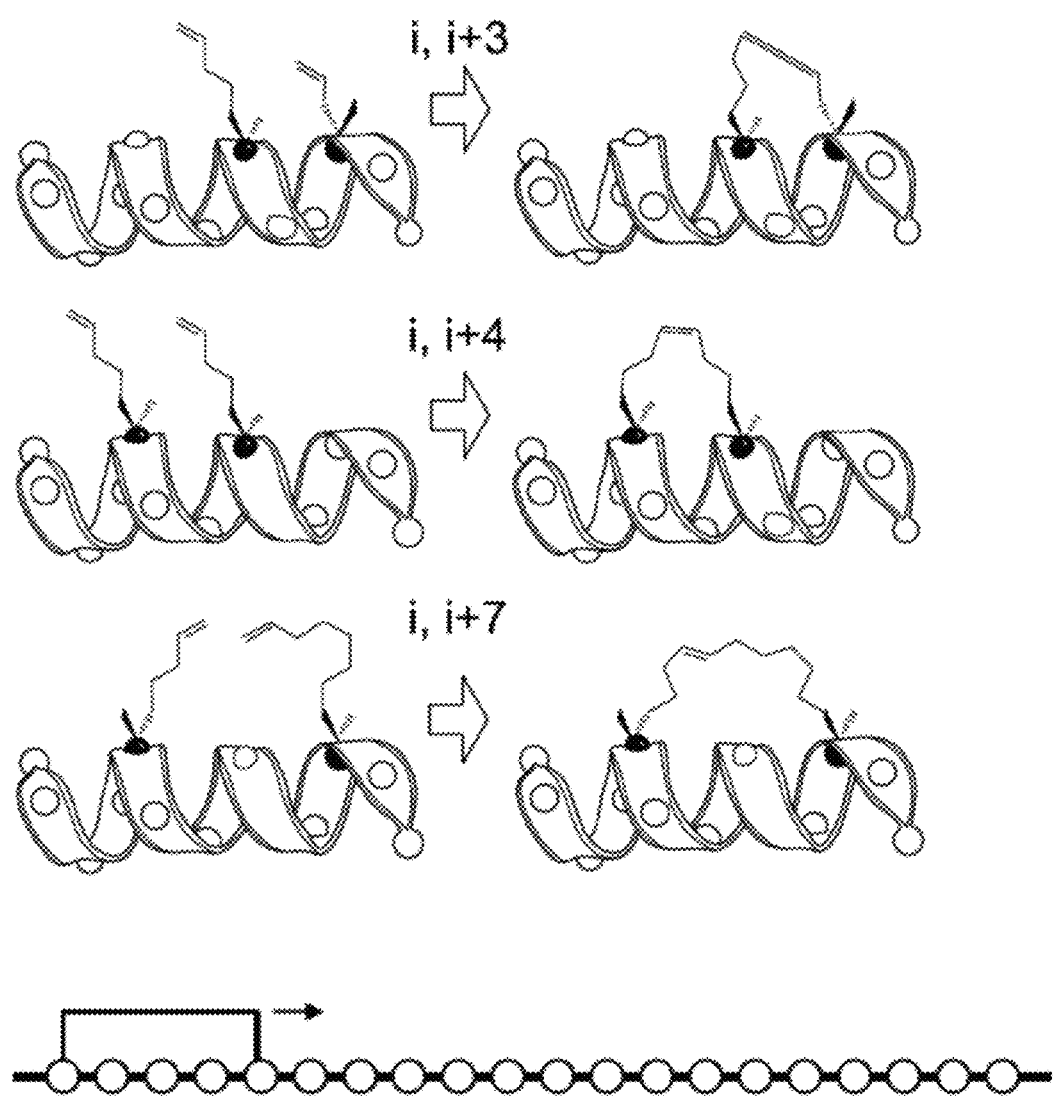
FIGS. 24A-C are graphics showing exemplary relative positions of staples and/or stitches that can be used in any of the internally cross-linked polypeptides and modified polypeptides described here.
Figure 24B:
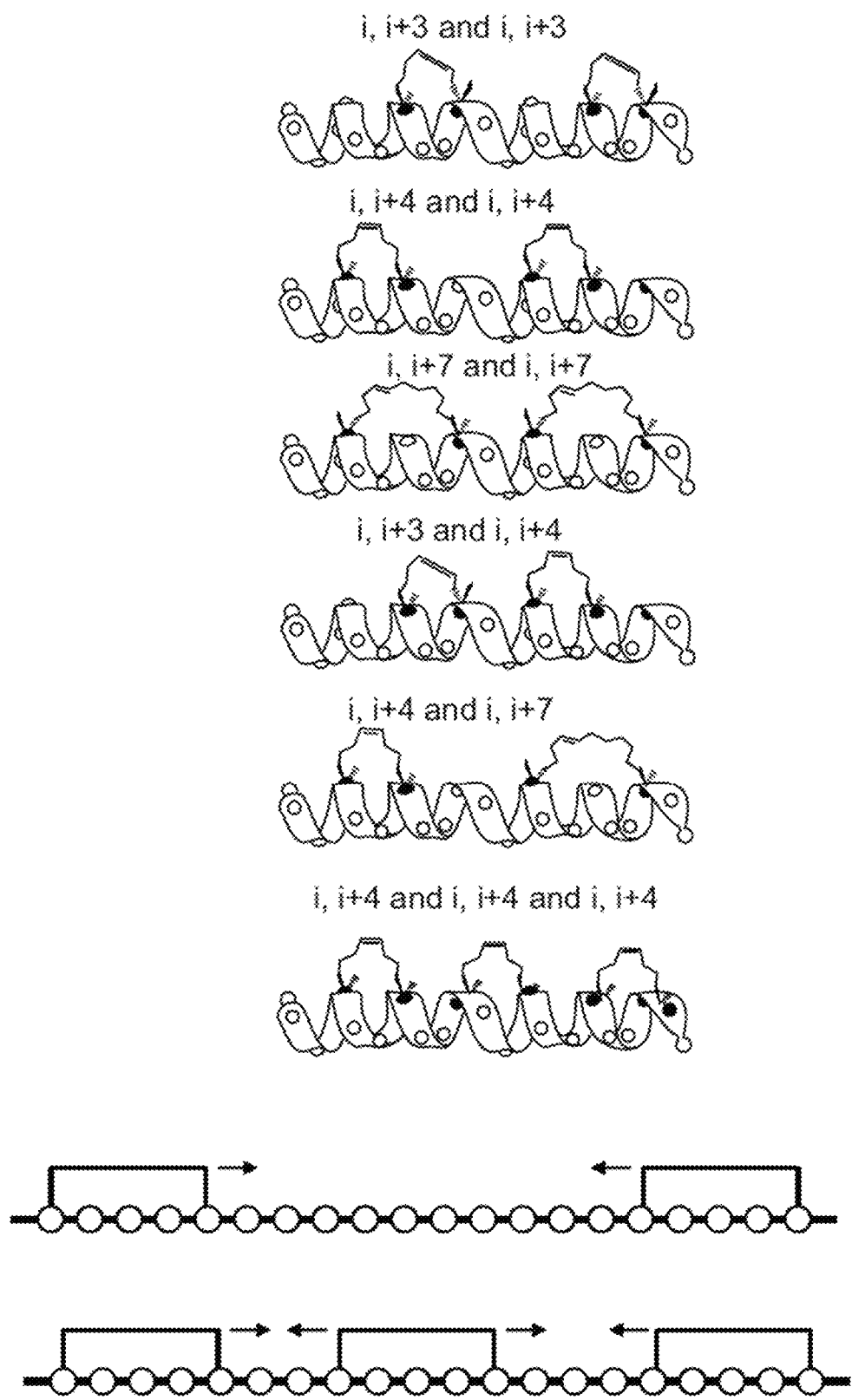
Figure 24C:
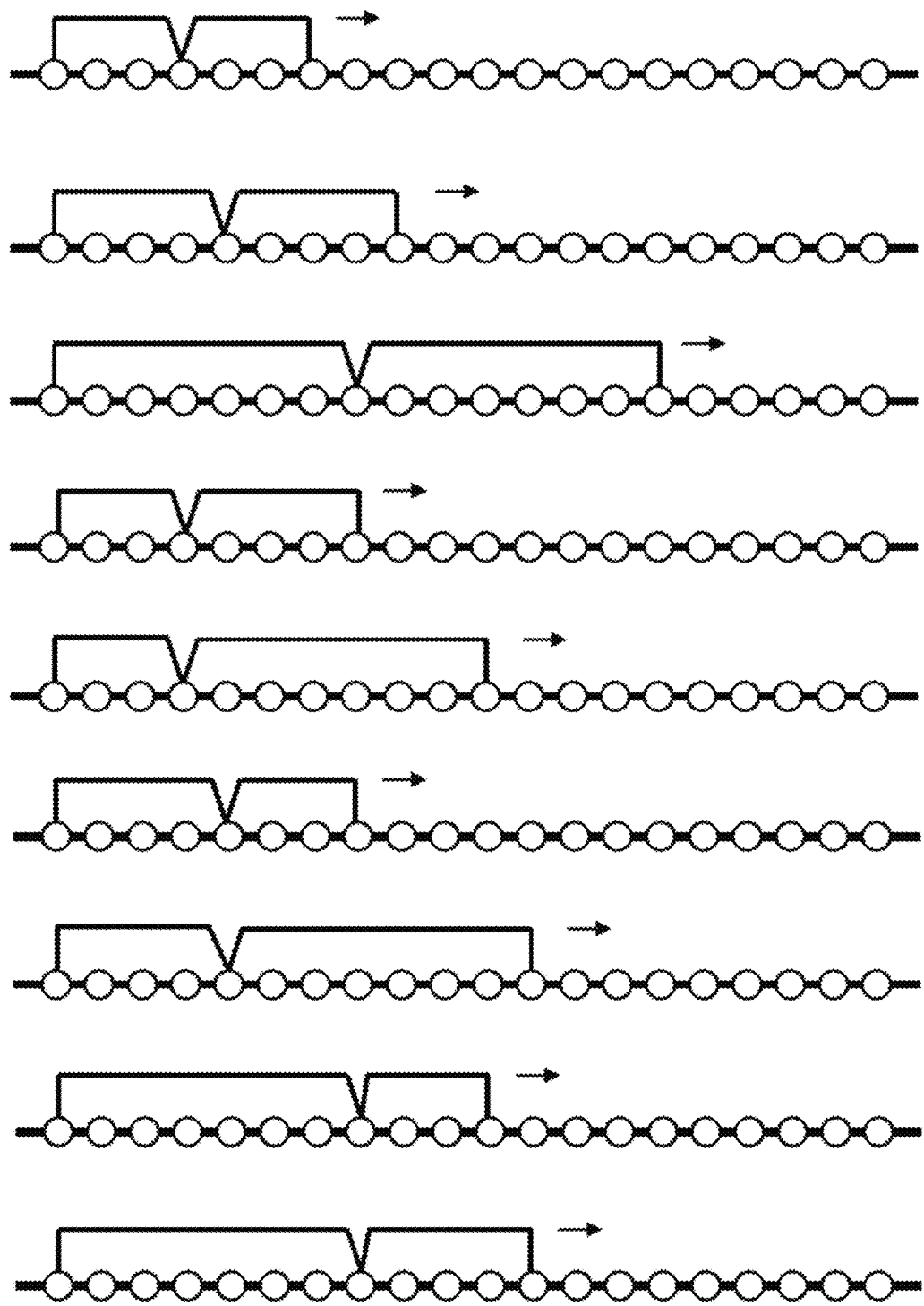

As disclosed above, internally cross-linked polypeptides or modified polypeptides herein include at least two modified amino acids that together form an internal (intramolecular) cross-link (or staple), wherein the at least two modified amino acids are separated by 2 (i.e., i, i+3, shown in Table 1 (FIG. 21), Table 2 (FIG. 22), or Table 3 (FIG. 23) as ☐), 3 (i.e., i, i+4, shown in Table 1 (FIG. 21), Table 2 (FIG. 22), or Table 3 (FIG. 23) as ○), or, 6 (i.e., i, i+7, shown in Table 1 (FIG. 22), Table 2 (FIG. 23), or Table 3 (FIGS. 24A-C) as ▲) amino acids. Additional exemplary relative positions of staple(s) and/or stitch(es) that can be introduced in any of the internally cross-linked polypeptides and modified polypeptides described herein are shown in FIGS. 24A-C.

In the case of a cross-link between i and i+3 the cross-link can be a C7 alkylene or alkenylene. In the case of a cross-link between i and i+4 the cross-link can be a C8 alkylene or alkenylene. In the case of a cross-link between i and i+7 the cross-link can be a C11, C12, or C13 alkylene or alkenylene. When the cross-link is an alkenylene, there can be one or more double bonds.

In the case of a cross-link between i and i+3 the cross-link can be a C6, C7, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12, or C13 alkyl or alkene (e.g., a C11 alkene having a single double bond). When the cross-link is an alkene, there can be one or more double bonds.

"Peptide stapling" is a term coined from a synthetic methodology, wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., *J. Org. Chem.*, 66: 5291-5302, 2001; Angew et al., *Chem. Int. Ed.* 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008/121767 and in WO 2010/068684, which are both hereby incorporated by reference in their entirety. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g, 1, 4 triazole or 1, 5 triazole) crosslinks can be used (Kawamoto et al., *J. Med. Chem.* 55:1137-1146, 2012; WO 2010/060112).

Stapling of a peptide using an all-hydrocarbon cross-link has been shown to help maintain its native conformation and/or secondary structure, particularly under physiologically relevant conditions (Schafmiester et al., *J. Am. Chem. Soc.* 122:5891-5892, 2000; Walensky et al., *Science* 305: 1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism, such as pinocytosis), and/or may lead to an improvement in the peptide's biological activity relative to the corresponding uncross-linked (e.g., "unstitched" or "unstapled") peptide. Such constraints have also been introduced into HIV gp41 domains (see, e.g., Bird et al., *Proc. Natl. Acad. Sci. U.S.A.*, 2010; WO 2010/148335), resulting in optimized anti-HIV fusion inhibitors with enhanced pharmacologic properties and stabilization of HIV epitopes for vaccine development.

Internally cross-linked polypeptides and modified polypeptides described herein include at least two internally cross-linked or stapled amino acids, wherein the at least two amino acids are separated by 2 (i.e., i, i+3, shown in Table 1 (FIG. 21), Table 2 (FIG. 22), and Table 3 (FIG. 23) as □), 3 (i.e., i, i+4, shown in Table 1 (FIG. 21), Table 2 (FIG. 22), and Table 3 (FIG. 23) as ○), or, 6 (i.e., i, i+7, shown in Table 1 (FIG. 21), Table 2 (FIG. 22), and FIG. 23 (Table 3) as ▲) amino acids. While at least two amino acids are required to support an internal cross-link (e.g., a staple), additional pairs of internally cross-linked amino acids can be included in a internally cross-linked polypeptide or modified polypeptide, e.g., to support additional internal cross-links (e.g., staples). For example internally cross-linked polypeptides and modified polypeptides can include 1, 2, 3, 4, 5, or more staples. Examples of peptide staples are illustrated in the Figures. Internally cross-linked polypeptides and modified polypeptides (e.g., stapled and/or stitched peptides) are generally referred to herein as SAHB peptides.

Alternatively or in addition, internally cross-linked polypeptides and modified polypeptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid and shown in Table 1 (FIG. 21), Table 2 (FIG. 22), and Table 3 (FIG. 23) as "i") forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g., i, i−3, i, i−4, i, i−7 (shown in Table 1 (FIG. 21), Table 2 (FIG. 22), and Table 23 (FIG. 23) as ■, ●, and ▼, respectively), i, i+3, i, i+4, i, i+7 (shown in Table 1 (FIG. 21), Table 2 (FIG. 22), and Table 3 (FIG. 23) as □, ○, and ▲, respectively), where "i" is the core amino acid). The number of amino acids on either side of the core (e.g., between the core amino acid and an amino acid cross-linked to the core) can be the same or different. In some instances, a stitch can include 3, 4, 5, or more internally cross-linked amino acids. In some instances, internally cross-linked polypeptides and modified polypeptides can include 1, 2, 3, 4, 5, or more stitches.

In some embodiments, internally cross-linked polypeptides or modified polypeptides described herein can include a combination of at least one (e.g., 1, 2, 3, 4, or 5) staple and at least one (e.g., 1, 2, 3, 4, or 5) stitch.

Internally cross-linked polypeptides or modified polypeptides (e.g., stapled and/or stitched peptides) are generally referred to herein as SAHB peptides. Internally cross-linked polypeptides and modified polypeptides can include cross-linked amino acids at one or more of the positions illustrated in Tables 1-3 (FIGS. 21-23).

In Tables 1-3 (FIGS. 21-23), the positions of cross-links are indicated by symbols and the letter "i". Two or more cross-links can be made in any of the positions indicated in Table 1 (FIG. 21) in the internally cross-linked polypeptides or modified polypeptides described herein. For example, in Table 1 (FIG. 21), $i_{15}$ ($O_0$ in SEQ ID NO: 135 or amino acid position 13 in SEQ ID NO: 1) can be linked via a i+4 staple to $i_{19}$ ($S_0$ in SEQ ID NO: 135 or amino acid position 17 in SEQ ID NO: 1) and/or to $i_{11}$ ($K_0$ in SEQ ID NO: 135 or amino acid position 9 in SEQ ID NO: 1)) via a i−4 staple. In another example, in Table 1 (FIG. 21), $i_{14}$ ($N_0$ in SEQ ID NO: 135 or amino acid position 12 in SEQ ID NO: 1) can be linked via a i+4 staple to $i_{18}$ ($R_0$ in SEQ ID NO: 135 or amino acid position 16 in SEQ ID NO: 1) and/or to $i_{10}$ ($J_0$ in SEQ ID NO: 135 or amino acid position 8 in SEQ ID NO: 1) via a i−4 staple. For example, in Table 2 (FIG. 22), $i_{14}$ ($N_0$ in SEQ ID NO: 136 or amino acid position 14 in SEQ ID NO: 2) can be linked via a i+4 staple to $i_{18}$ ($R_0$ in SEQ ID NO: 136 or amino acid position 18 in SEQ ID NO: 2) and/or to $i_{10}$ ($J_0$ in SEQ ID NO: 136 or amino acid position 10 in SEQ ID NO: 2) via a i−4 staple. For example, in Table 2 (FIG. 22), $i_{13}$ ($M_0$ in SEQ ID NO: 136 or amino acid position 13 in SEQ ID NO: 2) can be linked via a i+4 staple to $i_{17}$ ($Q_0$ in SEQ ID NO: 136 or amino acid position 17 in SEQ ID NO: 2), and/or to $i_9$ ($I_0$ in SEQ ID NO: 136 or amino acid position 9 in SEQ ID NO: 2) via a i−4 staple. For example in Table 3 (FIG. 23), $i_{13}$ ($M_0$ in SEQ ID NO: 3 or amino acid position 12 in SEQ ID NO: 3) can be linked via a i+4 staple to $i_{17}$ ($Q_0$ in SEQ ID NO: 137 or amino acid position 16 in SEQ ID NO: 3) and/or to $i_9$ ($I_0$ in SEQ ID NO: 137 or amino acid position 8 in SEQ ID NO: 3) via a i−4 staple. For example in Table 3 (FIG. 23), $i_{14}$ ($N_0$ in SEQ ID NO: 137 or amino acid position 13 in SEQ ID NO: 3) can be linked via a i+4 staple to $i_{18}$ ($R_0$ in SEQ ID NO: 137 or amino acid position 17 in SEQ ID NO: 3) and/or to $i_{10}$ ($J_0$ in SEQ ID NO: 137 or amino acid position 9 in SEQ ID NO: 3) via a i−4 staple.

Any of the internally cross-linked polypeptides in Tables 1-3 (FIGS. 21-23) can be modified to include a targeting moiety or a moiety that facilitates cell entry (e.g., 2, 3, 4, 5, 6, 7, 8 or 9 contiguous Arg) at the amino or carboxy terminus.

Internal cross-links (e.g., staples and/or stitches) can be positioned on amino acids within an internally cross-linked polypeptide or modified polypeptide to conserve the structural relationship of amino acids in the binding or interacting face of the peptide (e.g., to preserve the binding interface of a peptide). Alternatively, staples can placed on the interacting face as long as binding affinity or activity is not altered. In some embodiments, the staple or staples can be placed such that they partially or completely engage the target and enhance binding activity. For example, one or more of $i_1$-$i_{24}$ in Table 1 (FIG. 21), $i_1$-$i_{22}$ in Table 2 (FIG. 22), or $i_1$-$i_{22}$ in Table 3 (FIG. 23) can be stapled or stitched to at least one other amino acid to conserve the structural relationship of amino acids in an interaction face of the internally cross-stitched polypeptide or modified polypeptide. Such internal cross-links can include: one or more staples; one or more stitches; and/or a combination of one or more staples with one or more stitches. Exemplary internally cross-linked polypeptides and modified polypeptides include SEQ ID NOs: 4-71. In some instances, internally cross-linked polypeptides and modified polypeptides can include SEQ ID NO: 4 or SEQ ID NO: 6.

Selection of amino acids for modification (e.g., to support an internal cross-link) can also be facilitated by staple scanning. The term "staple scan" refers to the synthesis of a library of stapled peptides whereby the location of the i and i+3; i and i+4; i and i+7; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the Examples and Figures.

In some embodiments, the tethers, e.g., hydrocarbon staples are used to stabilize structures other than helices. In such cases, the ends of the tethers can be placed at intervals other than at i, i+3, i+4, and i+7.

Structurally constrained peptides and the like are understood to include modified peptides having any (i.e., at least one) chemical modification, e.g., mutation of the original or native sequence with a natural or non-natural amino acid; chemical modification to incorporate a molecular tether, chemical modification to promote the formation of a disulfide bridge, etc., such that the structurally constrained peptide adopts a more limited number of structures than the unmodified peptide. A structurally constrained peptide can include 1, 2, 3, 4, 5, 6, 7, 8, 9, 10, 11, 12, or more mutations as compared to the native, wild-type sequence. For example, molecular tethers can include hydrocarbon staples to promote the formation of stable helical structures, especially alpha-helical and $3_{10}$ structures, or kinks depending on the positions of the ends of the tethers and the lengths of the tethers. Natural or non-natural amino acids can be employed to promote kinks (e.g. bends in the structure as defined by the variable angles between the two adjoining structures) or other preferred confirmations. For example, the natural amino acid proline can induce a kink in a peptide due to the structure of the amino acid R group and the lack of a hydrogen-bond donor. Non-natural amino acids, particularly those having large and/or charged R groups, or N-methylated amides, N-substituted glycines, cyclic alpha, alpha-disubstitution, cyclic N,N-disubstitution, and beta-amino acids can promote specific, desired confirmations. It is understood that a population of "structurally constrained" peptides in solution may not all have the desired confirmation all of the time. Instead, in a population of structurally constrained peptides in solution, the desired confirmation is present at least about 30%, 40%, 50%, 60%, 70%, 80%, 90%, 100%, or more of the time than the native or original peptide sequence in solution prior to chemical modification. The structure of a population of peptides in solution can be determined by various methods known to those of skill in the art including, but not limited to, circular dichroism and NMR spectroscopy. X-ray crystallography can be applied to determine the structure of a constrained peptide when packed in the form of a crystal.

Suitable tethers are described herein and in U.S. Patent Application Publication No. 2005/0250680, WO 2008/121767, U.S. Patent Application Publication No. 2011/0318352, WO 2009/108261, and WO 2010/148335, each of which are herein incorporated by reference in their entirety.

Amino acid side chains suitable for use in the internally cross-linked polypeptides and modified polypeptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in cross-linking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking (see, Tables 1-3 in FIGS. 21-23). Thus, for example, where a peptide has the sequence . . . Xaa$_1$, Xaa$_2$, Xaa$_3$, Xaa$_4$, Xaa$_5$, Xaa$_6$, Xaa$_7$, Xaa$_8$, Xaa$_9$ . . . (wherein, " . . . " indicates the optional presence of additional amino acids), cross-links between Xaa$_1$ and Xaa$_4$, or between Xaa$_1$ and Xaa$_5$, or between Xaa$_1$ and Xaa$_8$ are useful, as are cross-links between Xaa$_2$ and Xaa$_5$, or between Xaa$_2$ and Xaa$_6$, or between Xaa$_2$ and Xaa$_9$, etc.

Internally cross-linked polypeptides and modified polypeptides can include more than one crosslink within the polypeptide sequence to either further stabilize the sequence or facilitate the stabilization of longer polypeptide stretches. If the polypeptides are too long to be readily synthesized in one part, independently synthesized, internally cross-linked polypeptides or modified polypeptides can be conjoined by a technique called native chemical ligation (Bang, et al., *J. Am. Chem. Soc.* 126:1377-1383, 2004). Alternately, large peptides are routinely synthesized using a convergent approach, whereby fully protected fragments are specifically and sequentially reacted to form the full length desired product, after final deprotection, such as in the industrial synthesis of Fuzeon.

The invention features a modified polypeptide of Formula (I),

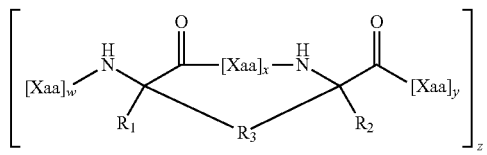

Formula (I)

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene, or alkynylene (e.g., a $C_6$, $C_7$, $C_8$, $C_{11}$, $C_{12}$ or $C_{13}$ alkylene), or [$R_4$'—K—$R_4$]$_n$; each of which is substituted with 0-6 $R_5$;

$R_4$ and $R_4$' are independently alkylene, alkenylene, or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, OR$_6$, N(R$_6$)$_2$, SR$_6$, SOR$_6$, SO$_2$R$_6$, CO$_2$R$_6$, R$_6$, a fluorescent moiety, or a radioisotope;

K is O, S, SO, SO$_2$, CO, CO$_2$, CONR$_6$,

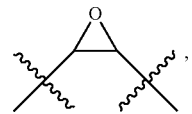 [SMILES: *C1OC1*]

aziridine, episulfide, diol, or amino alcohol;

$R_6$ is H, alkyl, or a therapeutic agent;

n is 2, 3, 4 or 6;

x is an integer from 2-10;

w and y are independently an integer from 0-100;

z is an integer from 1-10 (e.g., 1, 2, 3, 4, 5, 6, 7, 8, 9, or 10); and each Xaa is independently an amino acid (e.g., one of the 20 naturally occurring amino acids or any naturally occurring non-naturally occurring amino acid);

wherein the polypeptide comprises at least 8 (e.g., at least 9, 10, 11, 12, 13, 14, 15, 16, 17, 18, 19, 20, 21, 22, or 23) contiguous amino acids of any one of SEQ ID NOS:1-3 or a variant thereof (e.g., one, two, three, four, five, six, or seven amino acid substitutions), or another polypeptide sequence described herein, except that: (a) within the 8 contiguous (e.g., 9, 10, 11, 12, 13, 14, 15, 16, 17, 18, 19, 20, 21, 22, 23, or 24) amino acids of any one of SEQ ID NOS:1-3 the side chains of at least one pair (e.g., one, two, three, or four pairs) of amino acids separated by 2 to 6 amino acids (e.g., 2, 3, or 6 amino acids) is replaced by the linking group, $R_3$, which connects the alpha carbons of the pair of amino acids as depicted in Formula I; and (b) the alpha carbon of the first of the pair of amino acids is substituted with $R_1$ as depicted in Formula I and the alpha carbon of the second of the pair of amino acids is substituted with $R_2$ as depicted in Formula I.

In another aspect, the invention features a modified polypeptide of Formula (II),

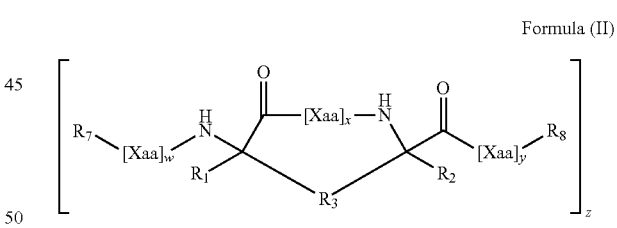

Formula (II)

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene, or alkynylene (e.g., a $C_6$, $C_7$, $C_8$, $C_{11}$, $C_{12}$ or $C_{13}$ alkylene) or [$R_4$'—K—$R_4$]$_n$; each of which is substituted with 0-6 $R_5$;

$R_4$ and $R_4$' are independently alkylene, alkenylene, or alkynylene (e.g., each are independently a $C_1$, $C_2$, $C_3$, $C_4$, $C_5$, $C_6$, $C_7$, $C_8$, $C_9$, or $C_{10}$ alkylene, alkenylene or alkynylene);

$R_5$ is halo, alkyl, OR$_6$, NHR$_6$, N(R$_6$)$_2$, SR$_6$, SOR$_6$, SO$_2$R$_6$, CO$_2$R$_6$, R$_6$, a fluorescent moiety, or a radioisotope;

K is O, S, SO, $SO_2$, CO, $CO_2$, $CONR_6$,

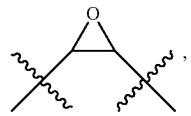 [SMILES: *C1OC1*]

aziridine, episulfide, diol, amino alcohol, or diamine;
$R_6$ is H, alkyl, or a therapeutic agent;
n is 2, 3, 4, 5, or 6;
x is an integer from 2-10;
w and y are independently an integer from 0-100;
z is an integer from 1-10 (e.g., 1, 2, 3, 4, 5, 6, 7, 8, 9, or 10); and
each Xaa is independently an amino acid (e.g., one of the 20 naturally occurring amino acids or any naturally occurring non-naturally occurring amino acid);
$R_7$ is selected from: a) PEG, b) a tat protein, c) an affinity label, d) a targeting moiety, e) a fatty acid-derived acyl group, f) a biotin moiety, g) a fluorescent probe (e.g., fluorescein or rhodamine) linked via, e.g., a thiocarbamate or carbamate linkage, or h) a sequence of 2, 3, 4, 5, 6, 6, 8 or 9 contiguous Arg;
$R_8$ is H, OH, $NH_2$, $NHR_{8a}$, or $NR_{8a}R_{8b}$;
wherein the polypeptide comprises at least 8 contiguous amino acids (e.g., 9, 10, 11, 12, 13, 14, 15, 16, 17, 18, 19, 20, 21, 22, 23, or 24) of any one of SEQ ID NOS:1-3 or a variant thereof (e.g., one, two, three, four, five, six, or seven amino acid substitutions), or another polypeptide sequence described herein except that: (a) within the at least 8 (e.g., 9, 10, 11, 12, 13, 14, 15, 16, 17, 18, 19, 20, 21, 22, 23, or 24) contiguous amino acids of any one of SEQ ID NOS:1-3, the side chains of at least one (e.g., 2, 3, 4, or 5) pair of amino acids separated by 2 to 6 amino acids (e.g., 2, 3, or 6 amino acids) is replaced by the linking group, $R_3$, which connects the alpha carbons of the pair of amino acids as depicted in Formula I; and (b) the alpha carbon of the first of the pair of amino acids is substituted with $R_1$ as depicted in Formula II and the alpha carbon of the second of the pair of amino acids is substituted with $R_2$ as depicted in Formula II.

In the case of Formula I or Formula II, the following embodiments are among those disclosed.

In cases where x=2 (i.e., i+3 linkage), R3 can be a C7 alkylene or alkenylene. Where it is an alkenylene, there can one or more double bonds. In cases where x=6 (i.e., i+4 linkage), $R_3$ can be a C11, C12, or C13 alkylene or alkenylene. Where it is an alkenylene, there can one or more double bonds. In cases where x=3 (i.e., i+4 linkage), $R_3$ can be a C8 alkylene or alkenylene. Where it is an alkenylene, there can one or more double bonds.

In certain instances, the two alpha, alpha-disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

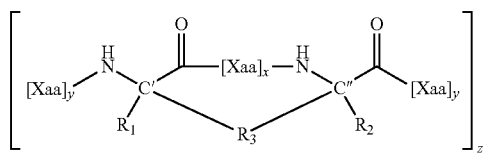

the C' and C'' disubstituted stereocenters can both be in the R configuration or they can both be in the S configuration, for example, when x is 3. When x is 6, the C' disubstituted stereocenter is in the R configuration and the C'' disubstituted stereocenter is in the S configuration or the C' disubstituted stereocenter is in the S configuration and the C'' disubstituted stereocenter is in the R configuration. The $R_3$ double bond may be in the E or Z stereochemical configuration. Similar configurations are possible for the carbons in Formula II corresponding to C' and C'' in the formula depicted immediately above.

In some instances $R_3$ is $[R_4—K—R_4']_n$; and $R_4$ and $R_4'$ are independently alkylene, alkenylene, or alkynylene (e.g., each are independently a C1, C2, C3, C4, C5, C6, C7, C8, C9 or C10 alkylene, alkenylene or alkynylene.

In some instances of any of the modified polypeptides described herein, the modified polypeptide includes an amino acid sequence which, in addition to the amino acids side chains that are replaced by a cross-link, have 1, 2, 3, 4, 5, 6, 7, 8, 9, 10, 11, or 12 amino acid changes (e.g., conservative amino acid changes) in any of SEQ ID NOs: 1-3.

The tether can include an alkyl, alkenyl, or alkynyl moiety (e.g., $C_6$, $C_8$, or $C_{11}$ alkyl or a $C_6$, $C_8$, or $C_{ii}$ alkenyl, or $C_5$, $C_8$, or $C_{ii}$ alkynyl). The tethered amino acid can be alpha disubstituted (e.g., $C_1$-$C_3$ or methyl). $[Xaa]_y$ and $[Xaa]_w$ are peptides that can independently comprise at least 1, 2, 3, 4, 5, 6, 7, 8, 9, 10, 11, 12, 13, 14, 15, 16, 17, 18, 19, 20, 21, 22, or 23 contiguous amino acids of any one of SEQ ID NOS: 1-3 and $[Xaa]_x$ is a peptide that can comprise between 2 to 7 (e.g., 2, 3, 6, or 7) contiguous amino acids of acids of any one of SEQ ID NOS: 1-3.

The internally cross-linked polypeptides and modified polypeptides can contain one or more asymmetric centers and thus occur as racemates and racemic mixtures, single enantiomers, individual diastereomers, and diastereomeric mixtures and geometric isomers (e.g., Z or cis and E or trans) of any olefins present. For example, internally cross-linked polypeptides or modified polypeptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al., Enantiomers, Racemates and Resolutions (Wiley Interscience, New York, 1981); Wilen, S. H. et al., *Tetrahedron* 33:2725 (1977); Eliel, EX, Stereochemistry of Carbon Compounds (McGraw-Hill, N Y, 1962); Wilen, S. H., Tables of Resolving Agents and Optical Resolutions p. 268 (EX. Eliel, Ed., Univ. of Notre Dame Press, Notre Dame, Ind., 1972). All such isomeric forms of these internally cross-linked polypeptides and modified polypeptides are expressly included in the present invention.

The internally cross-linked polypeptides or modified polypeptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the internally cross-linked polypeptides or modified polypeptides disclosed herein (the invention expressly includes all such reaction products). All such isomeric forms of such internally cross-linked polypeptides or modified polypeptides are included, as are all crystal forms.

The symbol " ⌇ " when used as part of a molecular structure, refers to a single bond or a trans or cis double bond.

The term "halo" refers to any radical of fluorine, chlorine, bromine, or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl, and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross-links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

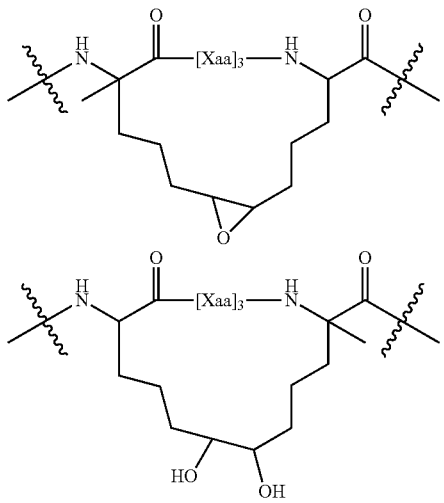

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., a cytoprotective agent). Such derivatization can alternatively be achieved by synthetic manipulation of the amino or carboxy-terminus of the internally cross-linked polypeptide or modified polypeptide, or via the amino acid side chain. Other agents can be attached to the functionalized tether, e.g., an agent that facilitates entry of the internally cross-linked polypeptide or modified polypeptide into cells.

While hydrocarbon tethers (cross-links) have been described, other tethers (cross-links) are also envisioned. For example, the tether can include one or more of an ether, thioether, ester, amine, or amide moiety. In some cases, a naturally-occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally-occurring amino acids rather than using a tether that is made by coupling two non-naturally occurring amino acids. It is also possible to use a single non-naturally occurring amino acid together with a naturally occurring amino acid.

It is further envisioned that the length of the tether (cross-link) can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers (cross-links) spanning from amino acids i to i+3, i to i+4; and i to i+7 have been described in order to provide a tether that is primarily on a single face of the alpha helix, the tethers can be synthesized to span any combinations of numbers of amino acids (e.g., i to i+7).

In some instances, alpha-disubstituted amino acids are used in the internally cross-linked polypeptide or modified polypeptide to improve the stability of the alpha-helical secondary structure. However, alpha-disubstituted amino acids are not required, and instances using mono-alpha substituents (e.g., in the tethered amino acids) are also envisioned.

In some instances it can be useful to create an inactive internally cross-linked polypeptide or modified polypeptide by introducing an alanine at position 12 in SEQ ID NO: 135 (e.g., $L_0$ of SEQ ID NO:135). In some instances, it can be useful to replace an amino acid on the interacting face of any one of SEQ ID NOS: 1-3 with another amino acid, e.g., Ala. Such inactive internally cross-linked polypeptides or modified polypeptides can be useful, for example, as negative controls.

The internally cross-linked polypeptides or modified polypeptides can include a drug (e.g., an additional cytotoxic agent or a cancer therapeutic), a toxin, a derivative of polyethylene glycol; a second polypeptide; a carbohydrate, etc. Where a polymer or other agent is linked to the internally cross-linked polypeptide or modified polypeptide it can be desirable for the composition containing these internally cross-linked polypeptides or modified polypeptides to be substantially homogeneous.

The addition of polyethelene glycol (PEG) molecules can improve the pharmacokinetic and pharmacodynamic properties of the modified polypeptide or internally cross-linked polypeptide. For example, PEGylation can reduce renal clearance and can result in a more stable plasma concentration. PEG is a water soluble polymer and can be represented as linked to the polypeptide as formula:

XO—$(CH_2CH_2O)_n$—$CH_2CH_2$—Y where n is 2 to 10,000 and X is H or a terminal modification, e.g., a $C_{1-4}$ alkyl; and Y is an amide, carbamate, or urea linkage to an amine group (including but not limited to, the epsilon amine of lysine or the N-terminus) of the internally cross-linked polypeptide or modified polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to a modified polypeptide or internally cross-linked polypeptide described herein through an intermediate linker. In certain embodiments, the linker is made up of from 1 to 20 amino acids linked by peptide bonds, wherein the amino acids are selected from the 20 naturally-occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —$NH(CH_2)_nC(O)$—, wherein n=2-20 can be used. These alkyl linkers may further be substituted by any non-sterically hindering group such as lower alkyl (e.g., $C_1$-$C_6$), lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The internally cross-linked polypeptides or modified polypeptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity, and/or decreases the needed frequency of administration. In some embodiments, the internally cross-linked polypeptides or modified polypeptides disclosed herein have an enhanced ability to penetrate cell membranes (e.g., relative to non-stapled peptides).

Methods of synthesizing the internally cross-linked polypeptides or modified polypeptides described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the internally cross-linked polypeptides and modified polypeptides described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The internally cross-linked polypeptides and modified polypeptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

One manner of making of the cross-linked polypeptides or modified polypeptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods. The peptides can be made in a high-throughput, combinatorial fashion, e.g., using a high-throughput multiple channel combinatorial synthesizer available from Advanced Chemtech.

One or more peptide bonds can be replaced, e.g., to increase physiological stability of the internally cross-linked polypeptide or modified polypeptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O), wherein R is H or CH$_3$; and a fluoro-ketomethylene bond (C(O)—CFR or CFR—C(O), wherein R is H, F, or CH$_3$.

The internally cross-linked polypeptides or modified polypeptides can be further modified by one or more of: acetylation, amidation, biotinylation, cinnamoylation, farnesylation, fluoresceination, formylation, myristoylation, palmitoylation, phosphorylation (Ser, Tyr, or Thr), stearoylation, succinylation, and sulfurylation. As indicated above, internally cross-linked polypeptides and modified polypeptides can be conjugated to, for example, polyethylene glycol (PEG); alkyl groups (e.g., C1-C20 straight or branched alkyl groups); fatty acid radicals; and combinations thereof.

α,α-Disubstituted non-natural amino acids containing olefinic side chains of varying length can be synthesized by known methods (Williams et al., *J. Am. Chem. Soc.* 113: 9276, 1991; Schafmeister et al., *J. Am. Chem Soc.* 122:5891, 2000; Bird et al., *Methods Enzymol.,* 446:369, 2008; Bird et al, *Current Protocols in Chemical Biology,* 2011). For internally cross-linked polypeptides or modified polypeptides, where an i linked to i+7 staple is used (two turns of the helix stabilized), either one S5 amino acid and one R8 is used, or one S8 amino acid and one R5 amino acid is used. R8 is synthesized using the same route, except that the starting chiral auxiliary confers the R-alkyl-stereoisomer. Also, 8-iodooctene is used in place of 5-iodopentene Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-S$_5$—OH, Fmoc-R$_8$—OH, Fmoc-R$_8$—OH, Fmoc-S$_8$—OH, and Fmoc-R$_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., *Org. Synth.,* 80:31, 2003).

In some instances, the internally cross-linked polypeptides and modified polypeptides can include a detectable label. As used herein, a "label" refers to a moiety that has at least one element, isotope, or functional group incorporated into the moiety which enables detection of the peptide (e.g., internally cross-linked polypeptide or modified polypeptide) to which the label is attached. Labels can be directly attached (i.e., via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to an internally cross-linked polypeptide or modified polypeptide at any position that does not interfere with the biological activity or characteristic of the inventive internally cross-linked polypeptide or modified polypeptide that is being detected.

Labels can include: labels that contain isotopic moieties, which may be radioactive or heavy isotopes, including, but not limited to $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; labels that include immune or immunoreactive moieties, which may be antibodies or antigens, which may be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA, and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}O$, $^{32}P$ $^{33}P$, and $^{18}F$.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally-occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase and aequorin, and derivatives thereof. Numerous fluorescent and luminescent dyes and proteins are known in the art (see, e.g., U.S. Patent Application Publication No. 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the internally cross-linked polypeptides and modified polypeptides disclosed herein are also known in the art (see, e.g., Bird et. al., *Methods in Enzymology* 446:369-386 (2008); Bird et al, *Current Protocols in Chemical Biology* 2011; Walensky et al., *Science* 305:1466-1470 (2004); Schafmeister et al., *J. Am. Chem. Soc.* 122: 5891-5892 (2000); U.S. Patent Application Publication No. 2010/0168388; and U.S. Pat. No. 7,723,468, each of which are hereby incorporated by reference in their entirety).

In some embodiments, the internally cross-linked polypeptides or modified polypeptides are substantially free of non-stapled peptide contaminants or are isolated. Methods for purifying internally cross-linked polypeptides or modified polypeptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the internally cross-linked polypeptides and modified polypeptides of the invention can be assayed, for example, using the methods described below. For example, any of the cross-linked polypeptides and polypeptides described herein can be tested for their ability to prevent or decrease stress-induced cell death (e.g., using methods described herein or known in the art) or to increase or induce cell death (e.g., apoptosis) (e.g., using fluorescence-assisted cell sorting, terminal deoxynucleotidyl transferase dUTP nick end labeling (TUNEL), and/or immunofluorescence microscopy, or any other methods known in the art for detecting cellular apoptosis or cell death). Additional exemplary methods for assaying the structure, binding activity, and biological activity of the internally cross-linked polypeptides and modified polypeptides are described in the Examples.

Assays to Determine α-Helicity:

Internally cross-linked polypeptides or modified polypeptides are dissolved in an aqueous solution (e.g. 5 mM potassium phosphate solution at pH 7, or distilled $H_2O$, to concentrations of 25-50 µM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each internally cross-linked polypeptide or modified polypeptide is calculated by dividing the mean residue ellipticity by the reported value for a model helical decapeptide (Yang et al., *Methods Enzymol.* 130:208 (1986)).

Assays to Determine Melting Temperature (Tm):

Internally cross-linked polypeptides/modified polypeptides or the unmodified template peptides are dissolved in distilled $H_2O$ or other buffer or solvent (e.g., at a final concentration of 50 µM) and Tm is determined by measuring the change in ellipticity over a temperature range (e.g., 4 to 95° C.) on a spectropolarimeter (e.g., Jasco J-710, Aviv) using standard parameters (e.g., wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone, and therefore may prevent or substantially retard proteolytic cleavage. The internally cross-linked polypeptides or modified polypeptides of the present invention may be subjected to in vitro enzymatic proteolysis (e.g., trypsin, chymotrypsin, and pepsin) to assess for any change in degradation rate compared to a corresponding uncross-linked or alternatively stapled polypeptide. For example, the internally cross-linked or modified polypeptide and a corresponding uncross-linked polypeptide are incubated with trypsin agarose and the reactions quenched at various time points by centrifugation and subsequent HPLC injection to quantitate the residual substrate by ultraviolet absorption at 280 nm. Briefly, the internally cross-linked polypeptide or modified polypeptide and the control uncross-linked polypeptide or alternatively stapled polypeptide (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Internally cross-linked polypeptides or modified polypeptides and/or a corresponding uncross-linked polypeptide can be each incubated with fresh mouse, rat, and/or human serum (e.g. 1-2 mL) at 37° C. for, e.g., 0, 1, 2, 4, 8, and 24 hours. Samples of differing internally cross-linked polypeptide or modified polypeptide concentration may be prepared by serial dilution with serum. To determine the level of intact internally cross-linked polypeptide or modified polypeptide, the following procedure may be used: The samples are extracted, for example, by transferring 100 μL of sera to 2-mL centrifuge tubes followed by the addition of 10 μL of 50% formic acid and 500 μL acetonitrile and centrifugation at 14,000 RPM for 10 min at 4+/−2° C. The supernatants are then transferred to fresh 2-mL tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays:

A key benefit of peptide stapling is the translation of in vitro protease resistance into markedly improved pharmacokinetics in vivo. Liquid chromatography/mass spectrometry-based analytical assays can be used to detect and quantitate the levels of internally cross-linked polypeptides or modified polypeptides in plasma. For pharmacokinetic analysis, internally cross-linked polypeptides or modified polypeptides are dissolved in sterile aqueous 5% dextrose (1 mg/mL) and administered to C57BL/6 mice (Jackson Laboratory) by bolus tail vein or intraperitoneal injection (e.g., 5, 10, 25, or 50 mg/kg). Blood is collected by retro-orbital puncture at 5, 30, 60, 120, and 240 minutes after dosing 5 animals at each time point. Plasma is harvested after centrifugation (2,500×g, 5 minutes, 4° C.) and stored at −70° C. until assayed. Peptide concentrations in plasma are determined by reversed-phase high performance liquid chromatography with electrospray ionization mass spectrometric detection (Aristoteli et al., *Journal of Proteome Res.* 6:571-581, 2007; Walden et al., *Analytical and Bioanalytical Chemistry* 378:883-897, 2004). Study samples are assayed together with a series of 7 calibration standards of internally cross-linked polypeptide or modified polypeptide in plasma at concentrations ranging from 1.0 to 50.0 μg/mL, drug-free plasma assayed with and without addition of an internal standard, and 3 quality control samples (e.g., 3.75, 15.0, and 45.0 μg/mL). Standard curves are constructed by plotting the analyte/internal standard chromatographic peak area ratio against the known internally cross-linked polypeptide or modified polypeptide concentration in each calibration standard. Linear least squares regression is performed with weighting in proportion to the reciprocal of the analyte concentration normalized to the number of calibration standards. Values of the slope and y-intercept of the best-fit line are used to calculate the internally cross-linked polypeptide or modified polypeptide in study samples. Plasma concentration-time curves are analyzed by standard noncompartmental methods using WinNonlin Professional 5.0 software (Pharsight Corp., Cary, N.C.), yielding pharmacokinetic parameters such as initial and terminal phase plasma half-life, peak plasma levels, total plasma clearance, and apparent volume of distribution.

In Vitro Binding Assays:

To assess the binding and affinity of internally cross-linked polypeptides or modified polypeptides to acceptor proteins (e.g., a BAX protein), a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled internally cross-linked polypeptides or modified polypeptides bound to a large protein) emit higher levels of polarized fluorescence due to their slower rates of rotation as compared to fluorescent tracers attached to smaller molecules (e.g. FITC-labeled internally cross-linked polypeptides or modified polypeptides that are free in solution).

In Vitro Displacement Assays to Characterize Antagonists of Peptide-Protein Interactions:

To assess the binding and affinity of compounds that antagonize the interaction between an internally cross-linked polypeptide or modified polypeptide and an acceptor protein (e.g., BAX protein), a fluorescence polarization assay (FPA) utilizing a fluoresceinated internally cross-linked polypeptide or modified polypeptide is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled internally cross-linked polypeptides or modified polypeptides bound to a large protein (e.g., BAX protein) emit higher levels of polarized fluorescence due to their slower rates of rotation as compared to fluorescent tracers attached to smaller molecules (e.g. FITC-labeled internally cross-linked polypeptides or modified polypeptides that are free in solution). A compound that antagonizes the interaction between the fluoresceinated internally cross-linked polypeptide or modified polypeptide and an acceptor protein will be detected in a competitive binding FPA experiment.

Binding Assays in Intact Cells:

It is possible to measure binding of peptides or internally cross-linked polypeptides or modified polypeptides to their natural acceptors (e.g., a BAX protein) on or in intact cells by immunoprecipitation experiments, e.g., as described herein in the Examples.

Cellular Penetrability Assays:

To measure the cell penetrability of the internally cross-linked polypeptides or modified polypeptides, intact cells are incubated with fluoresceinated internally cross-linked polypeptides (10 μM) for 4 hours in serum-free media or in media supplemented with human serum at 37° C., washed twice with media and incubated with trypsin (0.25%) for 10 minutes at 37° C. The cells are washed again and resuspended in PBS. Cellular fluorescence is analyzed, for example, by using either a FACSCalibur flow cytometer or Cellomics' KineticScan® HCS Reader.

Clinical Trials:

To determine the suitability of the internally cross-linked polypeptides, modified polypeptides, compounds, or pharmaceutical compositions of the invention for treatment of humans, clinical trials can be performed. For example, patients having a cytotoxic disease or suspected of having a cytotoxic disease are selected and separated into treatment and one or more control groups, wherein the treatment group is administered an internally cross-linked polypeptide, modified polypeptide, compound, or pharmaceutical composition of the invention, while the control groups receive a placebo or a known cytoprotective drug. The treatment safety and efficacy of the internally cross-linked polypeptides, modified polypeptides, compounds, or pharmaceutical compositions of the invention can thus be evaluated by performing comparisons of the patient groups with respect to factors, such as prevention of symptoms, time to resolution of symptoms, and/or time to a decrease in the number, severity, or frequency of one or more symptoms of a cytotoxic disease. In some embodiments, subject administered an internally cross-linked polypeptide, modified polypeptide, compound, or pharmaceutical composition of the invention can have a reduced number of symptoms of a cytotoxic disease as compared to a subject in a control group receiving a placebo.

Pharmaceutical Compositions

One or more of the internally cross-linked polypeptides or modified polypeptides disclosed herein (e.g., one or more of SEQ ID NOs: 4-71) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more internally cross-linked polypeptides or modified polypeptides. The terms "effective amount" and "effective to treat," as used herein, refer to an amount or a concentration of one or more internally cross-linked polypeptides and/or modified polypeptides or a pharmaceutical composition described herein utilized for a period of time (including acute or chronic administration and periodic or continuous administration) that is effective within the context of its administration for causing an intended effect or physiological outcome (e.g., prophylaxis or treatment of a cytotoxic disease, or prophylaxis or treatment of a cell proliferative disorder).

Pharmaceutical compositions of this invention can include one or more internally cross-linked polypeptides and/or modified polypeptides and any pharmaceutically acceptable carrier, adjuvant and/or vehicle. In some instances, pharmaceuticals can further include one or more additional therapeutic agents (e.g., one or more other cytoprotective agents, or one or more anti-cancer therapeutics) in amounts effective for achieving a modulation of disease or disease symptoms.

In some instances, some pharmaceuticals of the present disclosure can include one or more other cytoprotective agents and/or one or more agents for the alleviation of symptoms associated with a cytotoxic disease (e.g., one or more medicaments approved or awaiting approval by the Federal Drug Administration). In these instances, the internally cross-linked polypeptide or modified polypeptide has the activity of preventing or decreasing stress-induced cell death. Exemplary medicaments can include, for example, antioxidants, Szeto-Schiller peptides, ascorbic acid, and nitrite.

In some instances, some pharmaceuticals of the present disclosure can include one or more anti-cancer therapeutics and/or one or more agents for the alleviation of symptoms of a cell proliferative disorder (e.g., agents for the alleviation of symptoms of any of the various types of cancer described herein). In these instances, the internally cross-linked polypeptide or modified polypeptide has the activity of increasing or inducing cell death (e.g., apoptosis). Exemplary pharmaceuticals can include one or more analgesics, one or more anti-inflammatory agents (e.g., a non-steroidal anti-inflammatory drug, e.g., celecoxib, ketoprofen, ibuprofen, etodolac, naproxen, prioxicam, rofecoxib, sodium salicylate, diclonfenac, diflusinal, fenoprofen, and oxaprozin), one or more anti-convulsants (e.g., phenobarbital, methylphenobarbital, barbexaclone, clobazam, clonazepam, diazepam, midazolam, lorazepm, felbamate, carbamazepine, and oxcarbazepine), and one/or more steroids (e.g., hydrocortisone, prednisolone, methylprednisolone, prednisone, budesonide, betamethasone, and fluocortolone). Non-limiting examples of anti-cancer therapeutics include: alkylating agents (e.g., mechlorethamine, chlorambucil, cyclophosamide, ifosfamide, melphalan, streptozocin, carmustin, lomustine, busulfan, dacarbazine, temozolomide, thiotepa, and altretamine), antimetabolites (e.g., 5-fluorouracil, capecitabine, 6-mercaptopurine, methotrexate, gemcitabine, cytarabine, fludarabine, and premetrexed), anthracyclines (e.g., daunorubicin, doxorubicin, epirubicin, and idarubicin), topoisomerase inhibitors (e.g., topotecan, irinotecan, etoposide, and teniposode), mitotic inhibitors (e.g., paclitaxel, docetaxel, ixaberpilone, vinblastine, vincristine, vinorelbine, and estramustine), corticosteroids (e.g., dexamethasone, prednisolone, and methyl prednisolone), and therapeutic antibodies (e.g., bevacizumab, brentuximab vedotin, cetuximab, ibritumomab tiuxetan, ipilimumab, panitumumab, rituximab, tositumomab, and trastuzumab).

The term "pharmaceutically acceptable carrier or adjuvant" refers to a carrier or adjuvant that may be administered to a patient, together with one or more internally cross-linked polypeptides and/or modified polypeptides of this invention, and which does not destroy the pharmacological activity thereof and is nontoxic when administered in doses sufficient to deliver a therapeutic amount of the one or more internally cross-linked polypeptide and/or one or more modified polypeptide.

Pharmaceutically acceptable carriers and vehicles that may be used in the pharmaceutical compositions of this invention include, but are not limited to, ion exchangers, alumina, aluminum stearate, lecithin, self-emulsifying drug delivery systems (SEDDS), such as d-α-tocopherol polyethyleneglycol 1000 succinate, surfactants used in pharmaceutical dosage forms such as Tweens or other similar polymeric delivery matrices, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat. Cyclodextrins, such as α-, β-, and γ-cyclodextrin, may also be advantageously used to enhance delivery of the internally cross-linked polypeptides and/or modified polypeptides described herein.

The pharmaceutical compositions of this invention may contain any conventional non-toxic pharmaceutically-acceptable carriers, adjuvants, or vehicles. In some cases, the pH of the formulation may be adjusted with pharmaceutically acceptable acids, bases, or buffers to enhance the stability of the formulated internally cross-linked polypeptide(s) and/or modified polypeptide(s), or its delivery form. The term parenteral as used herein includes subcutaneous, intra-cutaneous, intra-venous, intra-muscular, intra-articular, intra-arterial, intra-synovial, intra-sternal, intra-thecal, intra-lesional, and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents, which are commonly used in the formulation of pharmaceutically acceptable dosage forms, such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions, and aqueous suspensions, dispersions, and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the internally cross-linked polypeptides, modified polypeptides, compounds, or pharmaceutical compositions (indicated below as 'X') disclosed herein in the following methods:

Substance X for use as a medicament in the treatment of one or more cytotoxic diseases disclosed herein (e.g., any of the exemplary cytotoxic diseases described herein or known in the art). Use of substance X for the manufacture of a medicament for the treatment of a cytotoxic disease (e.g., any of the exemplary cytotoxic diseases described herein or known in the art); and substance X for use in the treatment of a cytotoxic disease (e.g., any of the exemplary cytotoxic diseases described herein or known in the art).

Substance X for use as a medicament in the treatment of one or more cell proliferative disorders disclosed herein (e.g., any of the exemplary cell proliferative disorders, e.g., cancers, described herein or known in the art). Use of substance X for the manufacture of a medicament for the treatment of a cell proliferative disorder (e.g., any of the exemplary cell proliferative disorders, e.g., cancers, described herein or known in the art); and substance X for use in the treatment of a cell proliferative disorder (e.g., any of the exemplary cell proliferative disorders, e.g., cancers, described herein or known in the art).

In some instances, one or more of the internally cross-linked polypeptides and/or modified polypeptides described herein can be formulated as a cytoprotective composition (e.g., a pharmaceutical composition suitable for parenteral administration). In these examples, the internally cross-linked polypeptide or modified polypeptide has cytoprotective activity (e.g., reduces or prevents stress-induced cell death).

In some instances, one or more of the internally cross-linked polypeptides and/or modified polypeptides described herein can be formulated as an anti-cancer composition (e.g., a pharmaceutical composition suitable for parenteral administration). In these examples, the internally cross-linked polypeptide or modified polypeptide induces or increased cell death (e.g., apoptotic cell death).

Cytoprotective or anti-cancer compositions can include preservatives and additives. Preservatives can be included to limit or prevent microbial growth or contamination in a cytoprotective composition. Exemplary preservatives can include, but are not limited to, Thimerosal, Benzethonium chloride (Phemerol), Phenol, 2-phenoxyethanol. Exemplary additives can include human serum albumin, gelatin, and antibiotics.

In some instances, one or more of the internally cross-linked polypeptides and/or modified polypeptides disclosed herein can be conjugated, for example, to a carrier protein. Such conjugated compositions can be monovalent or multivalent. For example, conjugated compositions can include one internally cross-linked polypeptide or modified polypeptide disclosed herein conjugated to a carrier protein. Alternatively, conjugated compositions can include two or more internally cross-linked polypeptides or modified polypeptides disclosed herein conjugated to a carrier. In such instances, additional cytoprotective components or anti-cancer therapeutics can also be coupled to the carrier protein.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances a cell cytoprotection in a subject. Polymeric carriers can be a natural or a synthetic material containing one or more primary and/or secondary amino groups, azido groups, or carboxyl groups. Carriers can be water soluble.

Although effective amounts can depend, among other things, on the species of subject treated, the body weight of the subject, and the chosen treatment regimen, effective amounts can be readily determined. One or more internally cross-linked polypeptides and/or modified polypeptides disclosed herein can be formulated for sale in the US, import into the US, and/or export from the US.

Methods of Treatment and Methods of Decreasing/Increasing Stress-Induced Cell Death The disclosure includes methods of using one or more of the cross-linked polypeptides, modified polypeptides, compounds, or pharmaceutical compositions described herein for the treatment of cytotoxic disease. In these instances, the internally cross-linked polypeptide or modified polypeptide is cytoprotective (e.g., blocks or decreases stress-induced cell death).

The disclosure also includes methods of using one or more of the cross-linked polypeptides, modified polypeptides, compounds, or pharmaceutical compositions described herein for the treatment of a cell proliferative disorder (e.g., any of the non-limiting cancers described herein or any cancer known in the art). In these instances, the internally cross-linked polypeptide or modified polypeptide induces or increases cell death (e.g., apoptotic cell death).

The terms "treat" or "treating," as used herein, refers to partially or completely alleviating, inhibiting, ameliorating, and/or relieving the disease or condition from which the subject is suffering. In some instances, treatment can result in a decrease in the number of symptoms of a cytotoxic disease experienced by a subject, and/or a decrease in the frequency and/or intensity of one or more (e.g., two, three, or four) symptoms of a cytotoxic disease in a subject. In some embodiments, the methods described herein can prevent or delay the onset of one or more symptoms of a cytotoxic disease after exposure to a cytotoxic agent or a cytotoxic condition (e.g., ischemia, heat, or radiation) that typically appear in subjects exposed to a cytotoxic agent or cytotoxic exposure (e.g., ischemia, heat, or radiation) that do not receive treatment or receive a different treatment. In some instances, treatment can result in a decrease in the number of symptoms of a cell proliferative disorder (e.g., any of the cancers described herein or known in the art) experienced by a subject, and/or a decrease in the frequency and/or intensity of one or more (e.g., two, three, or four) symptoms of a cell proliferative disorder (e.g., any of the cancers described herein or known in the art) in a subject. In some embodiments, the methods described herein can prevent or delay the onset of one or more symptoms of a cell proliferative disorder (e.g., any of the cancers described herein or known in the art) after initial diagnosis or after exposure to a mutagenic substance or condition (e.g., radiation, arsenic, cadmium, asbestos, chromium, nickel, deaminating agents, and polycyclic aromatic hydrocarbons) that typically appear in subjects after initial diagnoses with a cell proliferative disorder or subjects exposed to a mutagenic substance or condition (e.g., radiation (e.g., X-rays, gamma rays, alpha particles, beta particles, and ultraviolet radiation), arsenic, cadmium, asbestos, chromium, nickel, deaminating agents, and polycyclic aromatic hydrocarbons) that do not receive treatment or receive a different treatment.

Also provided are methods of reducing stress-induced cell death in a subject that include selecting a subject exposed to or suspected of having been exposed to a cytotoxic agent or exposure, and administering to the subject an effective amount of one or more of the internally cross-linked polypeptides, modified polypeptides, compounds, or pharmaceutical compositions described herein. Again, in these embodiments, the internally cross-linked polypeptide or modified polypeptide is cytoprotective (e.g., blocks or reduces stress-induced cell death). By the phrase "stress-induced cell death" generally means stress-induced apoptosis. A "cytotoxic agent or exposure" is generally a compound or a physical condition (e.g., hypoxia, radiation, or heat) that triggers stress-induced apoptosis (e.g., through a mechanism that involves the release of pro-apoptotic factors from the mitochondria into the cytosol). A compound or physical condition that triggers stress-induced apoptosis can be produced or generated in a subject's body during the pathogenesis of several diseases (e.g., ischemia following heart attack, ischemia following stroke, release of factors in the body during trauma, and neurotoxicity resulting from a neurodegenerative disease). A decrease in stress-induced cell death in a subject can be determined indirectly by assessing a decrease in the rate of onset or the rate of progression of one or more symptoms of a cytotoxic disease in a subject following exposure to a cytotoxic agent or condition (e.g., any of those described herein or known in the art).

Also provided are methods of inducing cell death in a subject that include selecting a subject having or suspected of having a cell proliferative disorder (e.g., any of the cancers described herein or known in the art), and administering to the subject an effective amount of one or more of the internally cross-linked polypeptides, modified polypeptides, compounds, or pharmaceutical compositions described herein. Again, in these embodiments, the internally cross-linked polypeptide or modified polypeptide induces or increases cell death (e.g., apoptotic cell death). By the phrase "inducing cell death" generally means inducing apoptosis in two or more cells (e.g., two or more cancer cells) in a subject. A "mutagenic agent or condition" is generally a compound or a physical condition ((e.g., radiation, arsenic, cadmium, asbestos, chromium, nickel, deaminating agents, and polycyclic aromatic hydrocarbons) that induces mutations or increases the number of mutations within the genomic DNA of a cell. By the term "cell proliferative disorder" is meant a disease characterized by unregulated or dysregulated cell division in a subject (e.g., uncontrolled (increased) cell division). Non-limiting examples of cell proliferative disorders include cancers (e.g., leukemia, lymphoma, anal cancer, appendix cancer, astrocytomas, skin cancer, bile duct cancer, bladder cancer, bone cancer, brain cancer, breast cancer, lung cancer, cervical cancer, heart cancer, colon cancer, bile duct cancer, endometrial cancer, esophageal cancer, gallbladder cancer, gastric cancer, head and neck cancer, pancreatic cancer, kidney cancer, laryngeal cancer, lip and oral cavity cancer, liver cancer, lung cancer, mouth cancer, multiple myeloma, non-small cell lung cancer, nasal cavity and paranasal sinus cancer, ovarian cancer, penile cancer, thyroid cancer, prostate cancer, rectal cancer, small intestine cancer, sarcoma, testicular cancer, throat cancer, urethral cancer, uterine cancer, vaginal cancer, and vulvar cancer). In some embodiments, the subject has or is suspected of having a cell proliferation disorder (e.g., any of the examples of cancer described herein or known in the art). In some embodiments, the subject has previously been diagnosed as having a cell proliferative disorder (e.g., any of the examples of cancer described herein or known in the art). In some examples, the subject has previously received an anti-cancer treatment, and the subject did not respond or responded poorly to the prior treatment. An increase in cell death (e.g., the apoptotic cell death of cancer cells) in a subject can be determined indirectly by assessing a decrease in the rate of onset or the rate of progression of one or more symptoms (e.g., any of the symptoms of a cell proliferative disorder (e.g., any of the various types of cancer described herein or known in the art)) of a cell proliferative disorder in a subject (e.g., a subject previously diagnosed as having a cell proliferative disorder (e.g., any of the cancers described herein or known in the art) or a subject exposed to a mutagenic agent or condition. For example, successful treatment can result in a decrease in the rate of growth of a tumor (e.g., a decrease in the rate of increase in the size of one or more tumors in a subject or a decrease in the rate of increase in the tumor burden in the subject) or a decrease in the rate of formation of metastasis in the subject.

In general, these methods include selecting a subject and administering to the subject an effective amount of one or more of the internally cross-linked polypeptides, modified polypeptides, compounds, or pharmaceutical compositions described herein, and optionally repeating administration as required for the treatment of a cytotoxic condition and/or to decrease stress-induced cell death in a subject, or for treatment of a cell proliferative disorder and/or to induce or increase cell death (e.g., apoptosis of cancer cells) in a subject. Selecting a subject can include selecting a subject having or suspected of having a cytotoxic disease. Selecting a subject can include selecting a subject diagnosed as having a cytotoxic disease. Selecting a subject can also include selecting a subject that presents with two or more (e.g., 2, 3, 4, 5, or 6) symptoms of a cytotoxic disease (e.g., two or more of the exemplary symptoms described herein). Selecting a subject can also include selecting a subject that has been exposed to a cytotoxic agent or condition or is suspected of having been exposed to a cytotoxic agent or condition. A "cytotoxic disease," as used herein, is a disease that is caused by a pathological induction stress-induced apoptosis of cells in a subject. Non-limiting examples of cytotoxic diseases include tissue ischemia (e.g., ischemia caused by surgery, heart attack, stroke, or trauma), trauma (e.g., trauma caused by, e.g., crushing, or a surgical procedure), cardiotoxicity, neurotoxicity (e.g., neurotoxicity caused by one or more neurodegenerative diseases, e.g., Alzheimer's disease, Parkinson's disease, and amyotrophic lateral sclerosis), stroke, radiation exposure, and burns. A person can be diagnosed as having a cytotoxic disease based on the observation of two or more (e.g., 2, 3, 4, 5, or 6) symptoms of a cytotoxic disease in a subject. Non-limiting symptoms of cytotoxic diseases include: enlarged heart muscle, abnormal heart or lung sounds, swelling in the hands or feet, unusual weight gain, tired or weak, coughing spells, shortness of breath, pain, bloody stool, cognitive problems, sensory problems, impairment in motor skills, pallor, bluish discoloration and/or darkening of skin, chest pain or pressure, severe headache, abdominal pain, sudden difficulty with memory, thinking, talking, comprehension, writing, or reading, confusion or loss of consciousness, numbness, paralysis or inability to move a body part, loss of vision or changes in vision, impaired balance and coordination, vomiting blood, rectal bleeding or bloody stool, profuse sweating, unusual anxiety, cold skin, decreased number of blood cells, nausea, vomiting, loss of appetite, dizziness, redness in skin, itching, face drooping, arm weakness, difficulty with speech, skin blisters, charred skin, skin abrasions, skin punctures, cuts, bruises, memory loss, difficulty planning or solving problems, difficulty completing familiar tasks, confusion with time or place, trouble understanding visual images and spatial relationships, new problems with words in speaking or writing, misplacing things and losing the ability to retrace steps, decreased or poor judgment, withdrawal from work or social activities, changes in mood or personality, tremor, bradykinesia, rigid muscles, loss of automatic movements, and writing changes. As one skilled in the art can appreciate, additional methods for diagnosing a cytotoxic disease are known in the art.

Selecting a subject can include selecting a subject having or suspected of having a cell proliferative disorder. Selecting a subject can include selecting a subject diagnosed as having a cell proliferative disorder. Selecting a subject can also include selecting a subject that presents with two or more (e.g., 2, 3, 4, 5, or 6) symptoms of a cell proliferative disorder (e.g., two or more of the exemplary symptoms described herein). Selecting a subject can also include selecting a subject that has been exposed to a mutagenic agent or condition or is suspected of having been exposed to a mutagenic agent or condition. A person can be diagnosed as having a cell proliferative disorder based on the observation of two or more (e.g., 2, 3, 4, 5, or 6) symptoms of a cell proliferative disorder in a subject. Non-limiting symptoms of cell proliferative disorders include: unexplained weight loss, fever, fatigue, pain, hyperpigmentation, jaundice, erythema, pruritis, excessive hair growth, change in bowel habits and bladder function, sore that do not heal, white patches inside mouth or white spots on the tongue, unusual bleeding or discharge, thickening or lump in body, indigestion or trouble swallowing, and nagging cough or hoarseness. As one skilled in the art can appreciate, additional methods for diagnosing a cell proliferative disorder are known in the art.

The term "subject," as used herein, refers to any animal. In certain embodiments, the subject is a mammal. In certain embodiments, the term "subject," as used herein, refers to a human (e.g., a man, a woman, or a child). Subjects can be referred by a medical practitioner or can be self-referred.

The terms "administer," "administering," or "administration," as used herein refers to implanting, absorbing, ingesting, injecting, or inhaling, one or more of the inventive internally cross-linked polypeptides, modified polypeptides, compounds, or pharmaceutical compositions (e.g., any of those described herein). In some instances, one or more of the internally cross-linked polypeptides, modified polypeptides, compounds, or pharmaceutical compositions disclosed herein can be administered to a subject topically (e.g., nasally) and/or orally. For example, the methods herein include administration of an effective amount of one or more internally cross-linked polypeptides, modified polypeptides, compounds, or pharmaceutical compositions to achieve the desired or stated effect. The internally cross-linked polypeptides, modified polypeptides, compounds, and pharmaceutical compositions of this invention can be administered at least once a week (e.g., about twice a week, about three times a week, about four times a week, about five times a week, about six times a week, or about 1 to about 6 times per day) or alternatively, as a continuous infusion. Such administration can be used as a chronic or acute therapy.

Specific dosage and treatment regimens for any particular patient will depend upon a variety of factors, including the activity of the specific internally cross-linked polypeptide, modified polypeptide, or compound employed, the age, body weight, general health status, sex, diet, time of administration, rate of excretion, drug combination, the severity and course of the cytotoxic disease or cell proliferative disorder, condition or symptoms, the patient's disposition to the cytotoxic disease or cell proliferative disorder, cytotoxic disease or symptoms, cell proliferative disorder and symptoms, and the judgment of the treating physician.

Following administration, the subject can be evaluated to detect, assess, or determine the number of symptoms and/or the severity and/or frequency of one or more symptoms of a cytotoxic disease or cell proliferative disorder in the subject. In some instances, treatment can continue until a reduction in the number of symptoms and/or the severity and/or frequency of one or more symptoms of a cytotoxic disease or cell proliferative disorder is observed. Upon improvement of a patient's condition, a maintenance dose of a compound, internally cross-linked polypeptide, modified polypeptide, pharmaceutical composition, or a combination (e.g., one or more of the present compounds, internally cross-linked polypeptides and/or modified polypeptides and at least one additional cytoprotective agent or anti-cancer therapeutic) of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of cytotoxic disease or cell proliferative disorder symptoms.

Screening Methods

Internally cross-linked polypeptides and modified polypeptides disclosed herein can be used in screening methods to identify agents that interact (bind to) BAX protein and/or its close homologues BAK and BOK, and/or modulate (e.g., increase or decrease) the activity of BAX protein and/or its close homologues BAK and BOK. In some instances, screening methods include competitive screening assays. For example, methods can include determining whether an agent alters (e.g., reduces) binding of one or more of the internally cross-linked polypeptides or modified polypeptides disclosed herein to BAX protein, BAK protein, or BOK protein. In some instances, methods can include (i) determining a level of binding between one or more of the internally cross-linked polypeptides or modified polypeptides disclosed herein and a polypeptide containing the amino acid sequence of BAX protein, BAK protein, or BOK protein (e.g., in the absence of an agent); (ii) detecting the level of binding between one or more internally cross-linked polypeptides or modified polypeptides (e.g., the one or more polypeptides of (i)) and the polypeptide containing the amino acid sequence of BAX protein, BAK protein, or BOK protein in the presence of an agent, and (iii) identifying an agent that modulates (e.g., decreases) the level of binding between the one or more internally-cross-linked polypeptides or modified polypeptides and the polypeptide containing the amino acid sequence of BAX protein, BAK protein, or BOK protein as a candidate agent that interacts with BAX protein, BAK protein, or BOK protein and/or modulates the activity of BAX protein, BAK protein, or BOK protein; and, optionally, (iii) selecting the candidate agent. In some instances, (i) can include contacting the one or more internally cross-linked polypeptides and/or modified polypeptides with a polypeptide containing the amino acid sequence of BAX protein, BAK protein, or BOK protein (e.g., a tagged BAX protein, a tagged BAK protein, or a tagged BOK protein) and detecting the level of binding between the one or more internally cross-linked polypeptides and/or modified polypeptides with the polypeptide containing the amino acid sequence of BAX protein, BAK protein, or BOK protein (e.g., a tagged BAX protein, a tagged BAK protein, or a tagged BOK protein). (ii) can include contacting the one or more internally cross-linked polypeptides and/or one or more modified polypeptides and the agent with the polypeptide containing the amino acid sequence of BAX protein, BAK protein, or BOK protein (e.g., a tagged BAX protein, a tagged BAK protein, or a tagged BOK protein) and detecting the level of binding between the one or more internally cross-linked polypeptides and/or modified polypeptides with the polypeptide containing the amino acid sequence of BAX protein, BAK protein, or BOK protein (e.g., a tagged BAX protein, a tagged BAK protein, or a tagged BOK protein). The polypeptide containing the amino acid sequence of BAX protein, BAK protein, or BOK protein (e.g., a tagged BAX protein, a tagged BAK protein, or a tagged BOK protein) can be contacted with the one or more internally cross-linked polypeptides and/or modified polypeptides and the agent at the same time or at different times (e.g., the one or more internally cross-linked polypeptides and/or modified polypeptides can be contacted with the polypeptide containing the amino acid sequence of BAX protein, BAK protein, or BOK protein (e.g., a tagged BAX protein, a tagged BAK protein, or a tagged BOK protein) before or after the agent). In some embodiments, candidate agents (e.g., selected candidate agents) can be administered to a suitable animal model (e.g., an animal model of a cytotoxic disease) to determine if the agent treats the cytotoxic disease in the animal. In some instances, one or both of the internally cross-linked polypeptide or modified polypeptide and the polypeptide containing the amino acid sequence of BAX protein, BAK protein, or BOK protein can include a label (e.g., any of the labels described herein or known in the art). In some embodiments, the one or more internally cross-linked polypeptides and/or modified polypeptides or the polypeptide containing the amino acid sequence of BAX protein, BAK protein, or BOK protein can be attached (e.g., covalently bonded) to a surface or substrate (e.g., a bead, dish, or well in a multi-well plate).

The invention is further described in the following examples, which do not limit the scope of the invention described in the claims.

EXAMPLES

Example 1. Design of Stabilized Alpha-Helices of BCL-2 Domains (SAHBs) Modeled after the BH4 Domains of BCL-2, BCL-$X_L$, and BCL-W Alignment of the polypeptide sequences of the anti-apoptotic proteins of BCL-2, BCL-$X_L$, and BCL-W using ClustalW revealed a region of homology at the N-terminus of each protein that includes α-helix 1 (FIG. 1). Examples of conserved BH4 region sequences of other BCL-2 family proteins, such as MCL-1, BFL-1/A1, BAX, BAK, and BOK, are also shown (FIG. 1). Multiple stabilized alpha-helixes of BCL-2 domains (SAHBs) modeled after the BH4 domains of BCL-2, BCL-$X_L$, and BCL-W were synthesized and purified as previously described in Bird et al. (*Methods Enzymol.* 446:369-386, 2008) (FIG. 2). Each template sequence used included a core BH4 region of homology at the N-terminus of a BCL-2 family anti-apoptotic protein. Various constructs and mutants were synthesized for biochemical and cellular assays designed to dissect and modulate the interaction between the BH4 domain and BAX protein.

Multiple staple positions within the BCL-2 BH4 SAHB constructs were sampled for optimization of binding activity to pro-apoptotic BAX protein (see, e.g., the constructs shown in FIG. 3). The panel was designed to install a staple at each face of the α-helix, including non-helical regions of monomeric BCL-2 (as defined by the BCL-2 crystal structure described in Petros et al. (*Proc. Natl. Acad. Sci. U.S.A.* 98:3012-3017, 2001; PDB: 1G5M)) in order to evaluate both the importance of individual residues in the interaction and to identify the essential surface for BAX protein engagement. Other variations of staple insertion tested include single (i, i+3), (i, i+4), (i, i+7), and multiple staples comprised of the various single-staple positions.

Example 2. Hydrogen/Deuterium Mass Spectrometry Analysis of BH4 SAHBs

Figure 4:
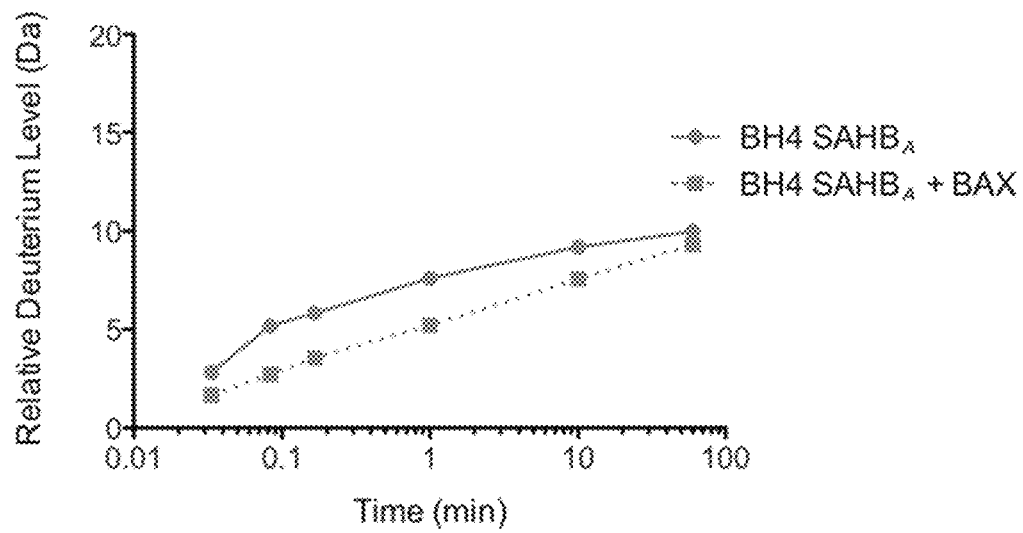
FIG. 4 is a graph of the relative deuterium level in Da over time for BH4 $SAHB_A$ when it was labeled with deuterium alone (solid line) or when it was labeled with deuterium following a 15 minute pre-equilibration with recombinant BAX protein at a 1:2 BAX:BH4 $SAHB_A$ molar ratio (dotted line).
Figure 5:
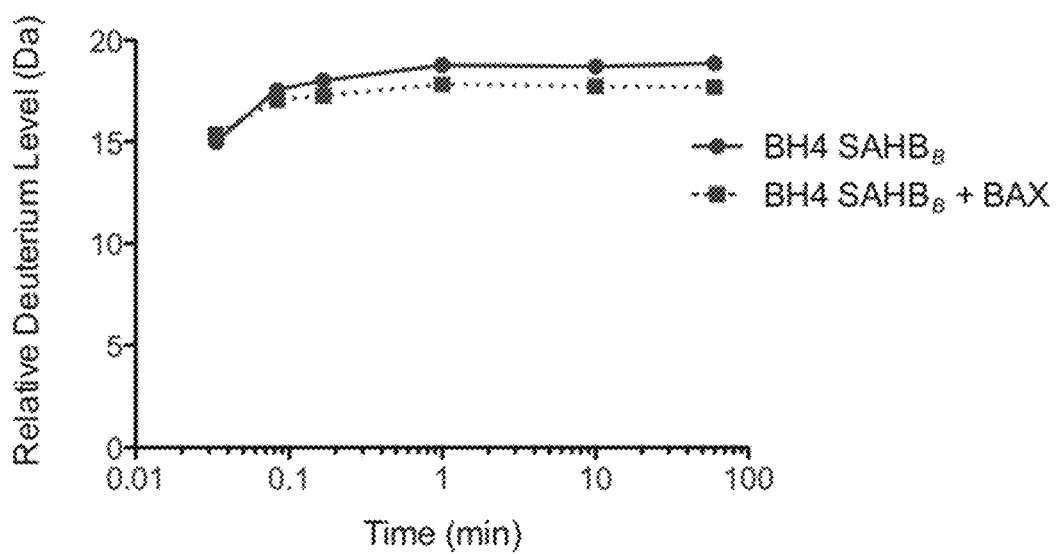
FIG. 5 is a graph of the relative deuterium level in Da over time for BH4 $SAHB_B$ when it was labeled with deuterium alone (solid line) or when it was labeled with deuterium following a 15 minute pre-equilibration with recombinant BAX protein at a 1:2 BAX:BH4 $SAHB_B$ molar ratio (dotted line).
Figure 6:
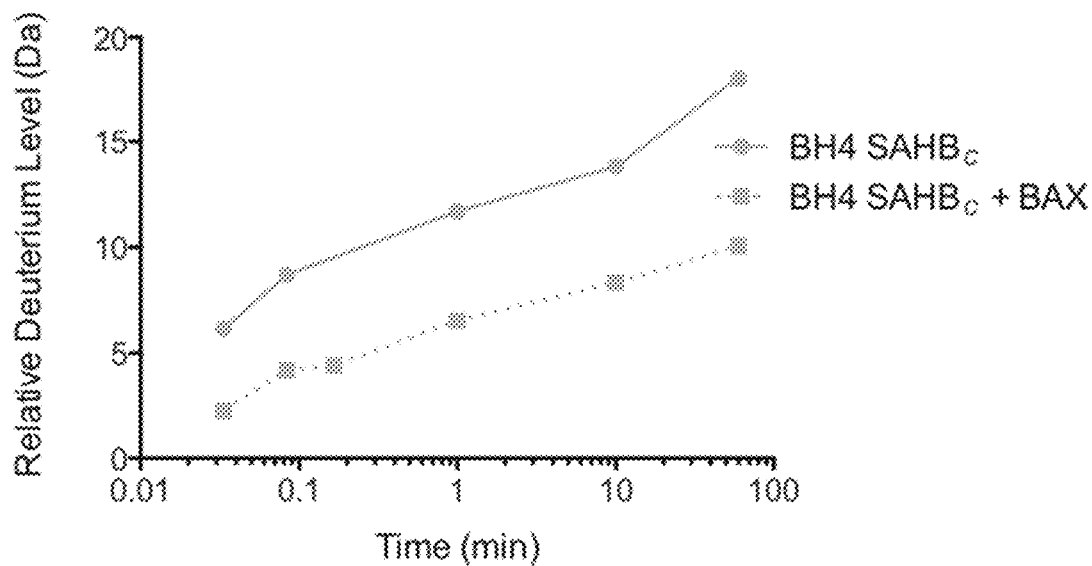
FIG. 6 is a graph of the relative deuterium level in Da over time for BH4 $SAHB_C$ when it was labeled with deuterium alone (solid line) or when it was labeled with deuterium following a 15 minute pre-equilibration with recombinant BAX protein at a 1:2 BAX:BH4 $SAHB_C$ molar ratio (dotted line).
Figure 7:
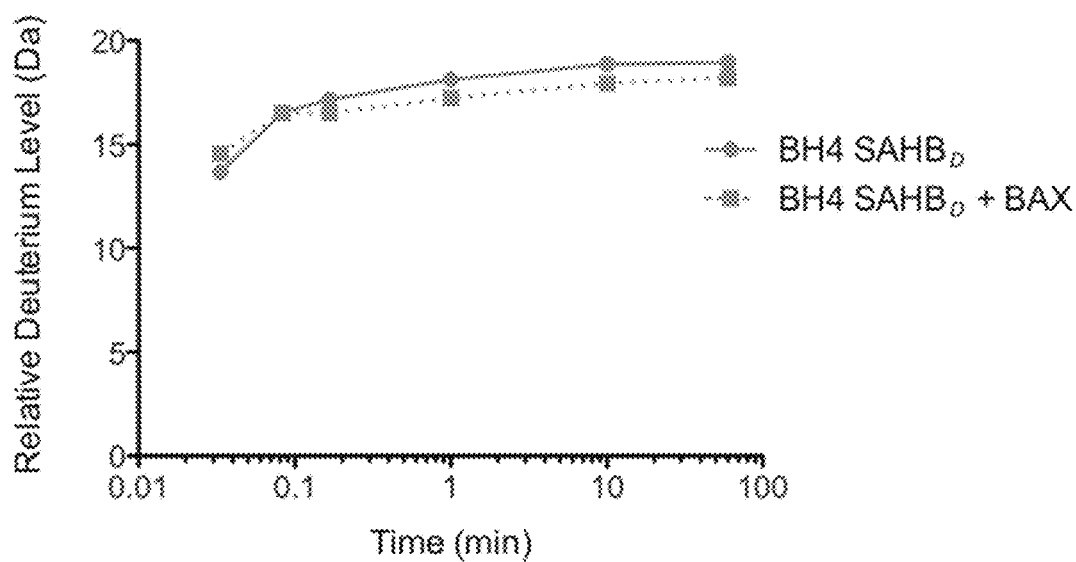
FIG. 7 is a graph of the relative deuterium level in Da over time for BH4 $SAHB_D$ when it was labeled with deuterium alone (solid line) or when it was labeled with deuterium following a 15 minute pre-equilibration with recombinant BAX protein at a 1:2 BAX:BH4 $SAHB_D$ molar ratio (dotted line).
Figure 8:
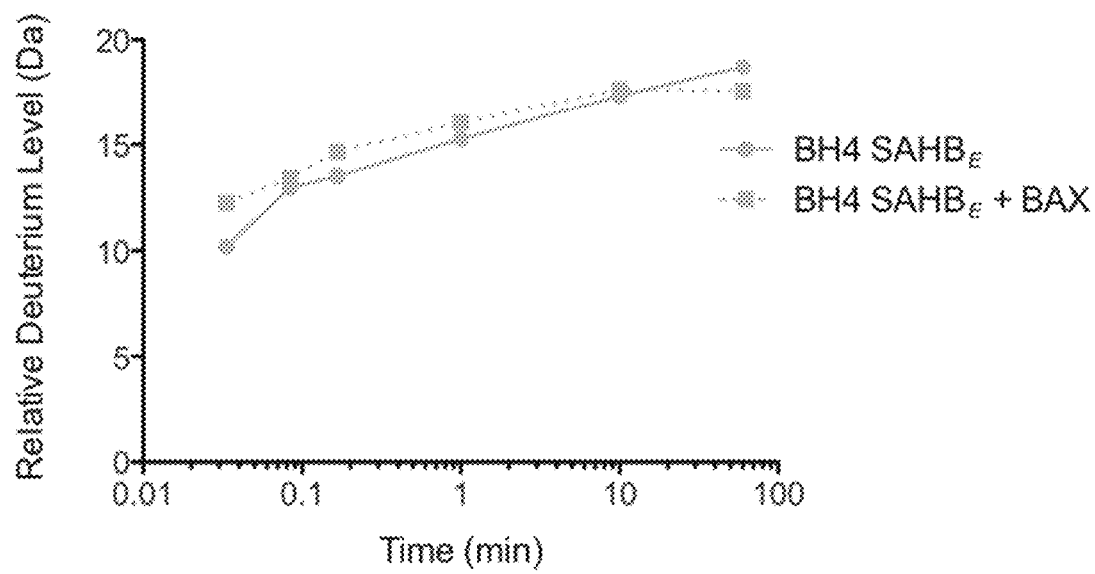
FIG. 8 is a graph of the relative deuterium level in Da over time for BH4 $SAHB_E$ when it was labeled with deuterium alone (solid line) or when it was labeled with deuterium following a 15 minute pre-equilibration with recombinant BAX protein (BAX) at a 1:2 BAX:BH4 $SAHB_E$ molar ratio (dotted line).

The structural stability of the BCL-2 BH4 staple-scan panel of SAHBs was determined by hydrogen/deuterium mass spectrometry (HXMS). In these experiments, the BH4 SAHBs were labeled with deuterium for 2 seconds, 5 seconds, 10 seconds, 1 minute, 10 minutes, and 1 hour, followed by quenching with cold phosphate buffer (pH 2.5), and then immediately subjected to desalting and injection on a LCT Premier Mass Spectrometer (Waters Corporation). The relative uptake of deuterium was determined for each BH4 SAHB by dividing the mass of the corresponding undeuterated control. Labeling was performed with the BH4 SAHB peptide alone and following a 15-minute pre-equilibration with recombinant BAX protein (purified as previously described in Walensky et al. (Mol. Cell 24:199-210, 2006) and Gavathiotis et al. (Nature 455:1076-1081, 2008)) at a 1:2 BAX protein to BH4 SAHB peptide molar ratio. The data show that BH4 SAHBs B, D, and E undergo rapid deuterium uptake that is reflective of an unstructured peptide state, and that BH4 SAHB$_A$ demonstrated markedly reduced uptake, with BH4 SAHB$_C$ exhibiting an intermediate level of uptake (FIGS. 4-8). The notably reduced uptake of the BH4 SAHB$_A$ construct is a reflection of a structurally-stabilized α-helical state. Upon addition of recombinant BAX protein, BH4 SAHBs A and C demonstrate reduced uptake, a result that is consistent with further stabilization of the BH4 SAHB structure upon binding to the BAX protein (FIGS. 4 and 6).

Figure 9:
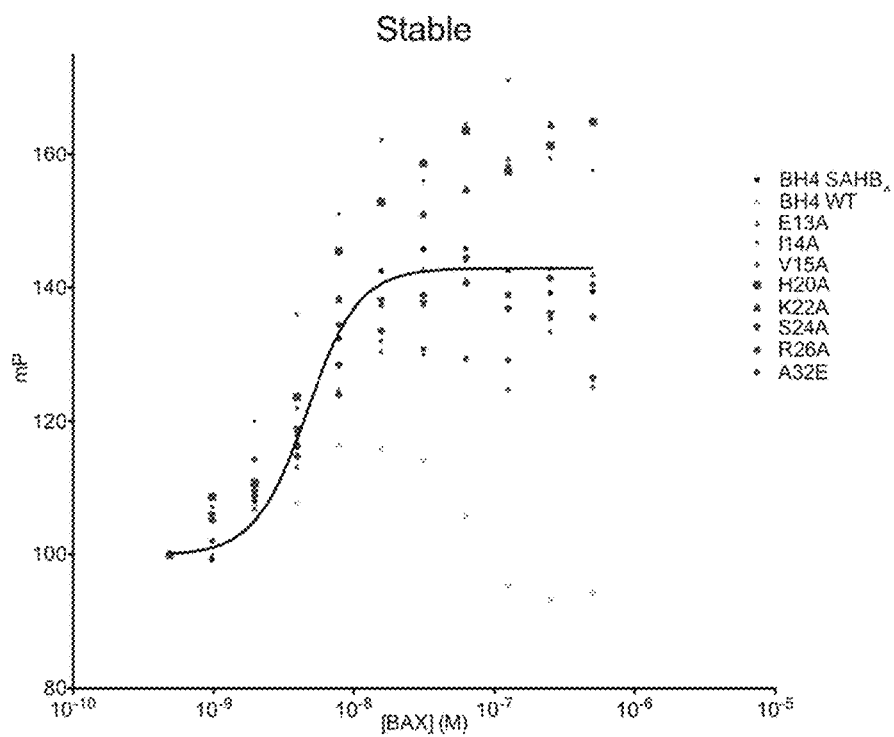
FIG. 9 is a graph of the polarization response (millipolarization or mP) of FITC-labeled unmodified BH4 peptide, BH4 $SAHB_A$, and a variety of point mutants of BH4 $SAHB_A$ (E13A, I14A, V15A, H20A, K22A, S24A, R26A, or A32E point mutants) when incubated with different concentrations of recombinant BAX protein. The data shown are representative of at least two independent binding experiments.
Figure 10:
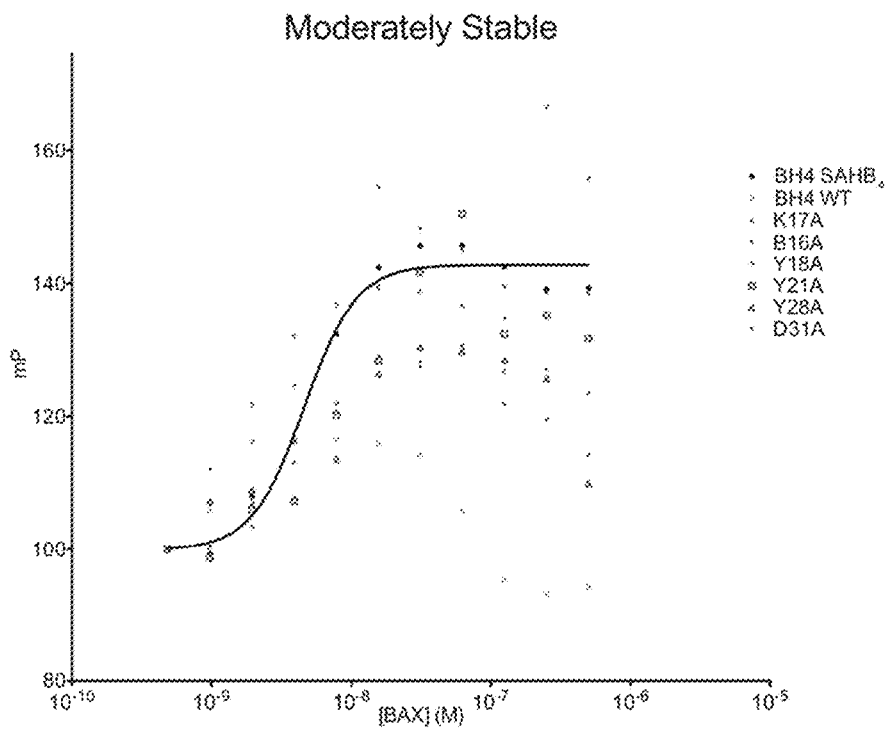
FIG. 10 is a graph of the polarization response (millipolarization or mP) of FITC-labeled unmodified BH4 peptide, BH4 $SAHB_A$, and a variety of point mutants of BH4 $SAHB_A$ (K17A, B16A, Y18A, Y21A, Y28A, or D31A point mutants) when incubated with different concentrations of recombinant BAX protein. The data shown are representative of at least two independent binding experiments.
Figure 11:
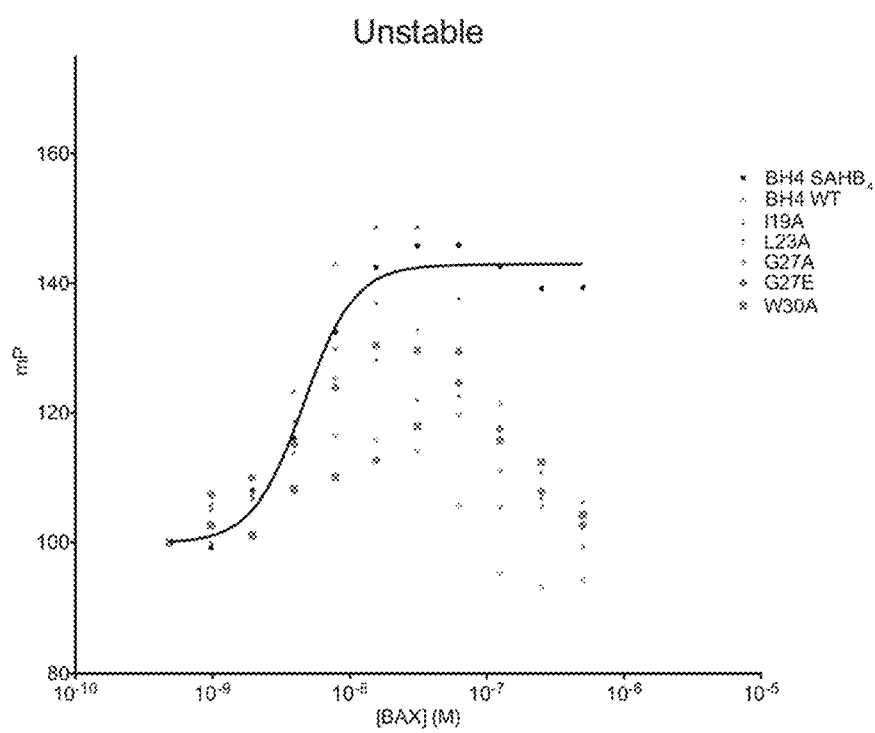
FIG. 11 is a graph of the polarization response (millipolarization or mP) of FITC-labeled unmodified BH4 peptide, BH4 $SAHB_A$, and a variety of point mutants of BH4 $SAHB_A$ (I19A, L23A, G27A, G27E, or W30A point mutants) when incubated with different concentrations of recombinant BAX protein. The data shown are representative of at least two independent binding experiments.

Example 3. Fluorescence Polarization Analysis of Binding of FITC-Labeled BH4 SAHBs Alanine scanning mutagenesis of the BCL-2 BH4 SAHB$_A$ construct revealed three classes of mutants whose BAX-binding activity could be divided into three categories: stable, moderately stable, and unstable (or impaired) (FIGS. 9-11). FITC-labeled peptides were incubated with recombinant BAX protein at the various concentrations at room temperature for 60 minutes. The binding activity was measured by fluorescence polarization (FP) using a SpectraMax M5 microplate reader (Molecular Devices). The EC$_{50}$ value for BCL-2 BH4 SAHB$_A$ binding was determined to be 4.6 nM by nonlinear regression analysis of the dose-response curve using Prism software 4.0 (GraphPad). L23A mutagenesis of the BCL-2 BH4 SAHB$_A$ peptide, for example, notably impaired BAX-binding activity (FIG. 11).

Example 4. BCL-2 BH4 SAHB$_A$ Inhibits BAX Activity

Figure 12:
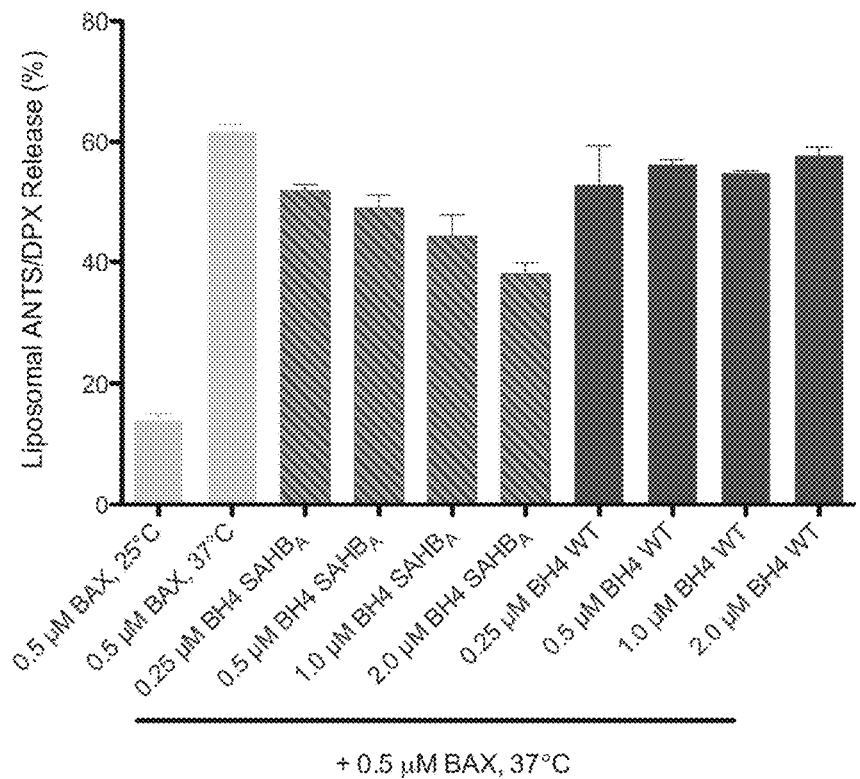
FIG. 12 is a graph of the percent liposomal ANTS/DPX release following incubation of BCL-2 BH4 $SAHB_A$ or unmodified BH4 peptide with 500 nM recombinant BAX and 5 μL of liposomes containing entrapped fluorophore (ANTS) and quencher (DPX) at 37° C. BAX alone at 25 C or 37 C degrees, serve as negative and positive controls, respectively. The data shown are the mean of three experiments, and the error bars represent ±standard deviation.

BCL-2 BH4 SAHB$_A$ and unmodified BCL-2 BH4 peptide were incubated with 500 nM recombinant BAX protein and 5 µL of liposomes containing entrapped fluorophore (8, aminonaphthalene-1,3,6-trisulfonate (ANTS)) and quencher (p-xylene-bis-pyridinium bromide (DPX)), generated as previously described in Cohen et al. (Chem. Biol. 19:1175-1186, 2012). The reaction mixture was heated to 37° C. while fluorescence was measured at the indicated time points using a Tecan M1000 spectrophotometer (excitation wavelength of 355 nm and an emission wavelength of 520 nm). The BCL-2 BH4 SAHB$_A$ dose-responsively decreased heat-induced activation of BAX and BAX-mediated portion, whereas the unmodified BH4 peptide had no such effect (FIG. 12).

Figure 13:
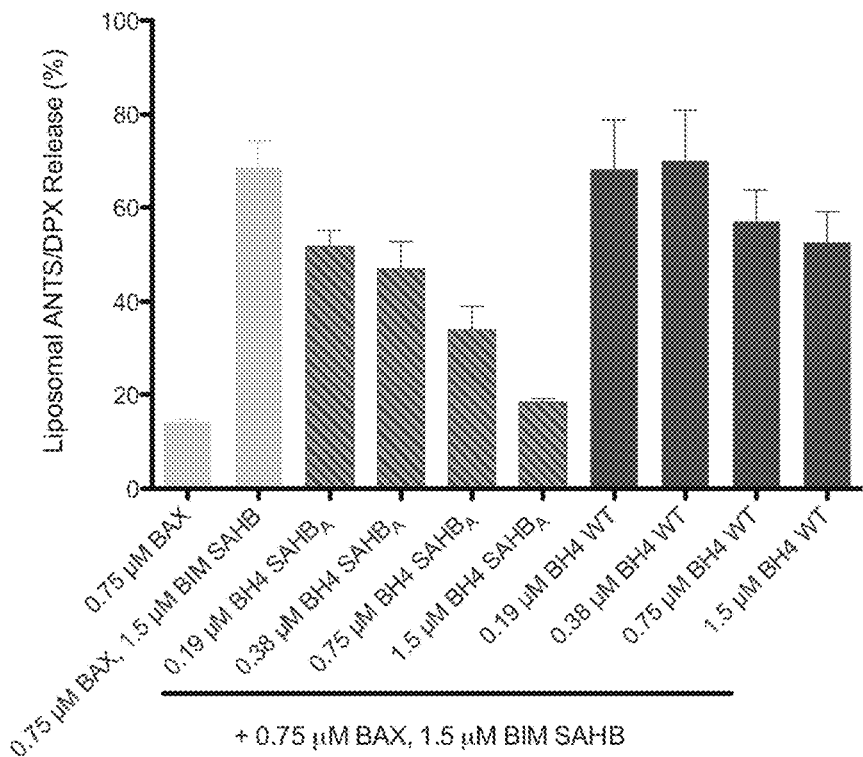
FIG. 13 is a graph of the percent liposomal ANTS/DPX release following incubation of BCL-2 BH4 $SAHB_A$ or unmodified BH4 peptide with 1.5 μM BCL-2-like protein 11 (BIM) SAHB, 0.75 μM recombinant BAX, and 5 μL liposomes containing entrapped fluorophore (ANTS) and quencher (DPX). BAX alone and BAX/BIM SAHB conditions serve as negative and positive controls, respectively. The data shown are the mean of three experiments, and the error bars represent ±standard deviation.

Additional experiments were performed to determine whether BCL-2 BH4 SAHB$_A$ would also inhibit BIM SAHB$_A$-mediated activation of BAX protein. In these experiments, the BCL-2 BH4 SAHB$_A$ and unmodified BCL-2 BH4 peptide were incubated with 1.5 µM BIM SAHB$_A$ (Gavathiotis et al., Nature 455:1076-1081, 2008), 0.75 µM recombinant BAX protein, and 5 µL liposomes loaded with the ANTS and DPX (described above) at a variety of different concentrations. The data show that BCL-2 BH4 SAHB$_A$ dose-responsively decreased BAX activation in response to BIM SAHB$_A$ treatment, whereas the unmodified BH4 peptide exhibited a modest inhibitory effect (FIG. 13).

Example 5. Interaction Site Between BCL-2 BH4 SAHB$_A$ and BAX

A complete panel of BCL-2 BH4 SAHB$_A$ alanine and glutamine point mutants (0.75 µM) were screened for inhibition of BIM SAHB$_A$ (0.75 µM)-triggered BAX activation (0.75 µM) using the liposome release assay described above. The data were normalized to a 100% percent positive control level of liposome release achieved using BIM SAHB$_A$ and BAX alone, after correction for any intrinsic fluorescence detected for each FITC-labeled BCL-2 BH4 SAHB (0%). The data show that alanine mutagenesis of discrete BH4 residues, such as L23A, markedly impair the BAX inhibitory activity of BCL-2 BH4 SAHB$_A$ (FIG. 14A). Whereas BCL-2 BH4 SAHB$_A$ dose-responsively blocks BIM SAHB$_A$-triggered BAX-mediated liposomal portion, L23A mutagenesis abrogates the effect (FIG. 14B). The alanine scanning data are also useful for designing the placement of staples in the BCL-2 BH4 peptides.

In additional studies, recombinant BAX protein was labeled with deuterium in the presence or absence of a two molar access of BCL-2 BH4 SAHB$_A$ for 10 seconds, 1 minute, 10 minutes, and 2 hours. Following the corresponding incubation period in D$_2$O buffer, each sample was quenched with ice-cold phosphate buffer (pH 2.5) and injected on a custom Waters NanoACUITY UPLC HDX Manager for analysis as described in Wales et al. (Anal. Chem. 80:6815-6820, 2008). Mass spectra were obtained with a Synapt G2 mass spectrometer (Waters Corporation) and analyzed with the DynamX software package (Waters Corporation). The data shown in FIG. 15A are the average of two duplicate experiments, where the relative difference (Da) shown for each peptide is equivalent to the relative deuterium uptake of the corresponding peptide in the BAX alone control minus the relative deuterium uptake of the peptide in the BCL-2 BH4 SAHB$_A$-bound BAX sample. A significant relative difference is established as 0.4 Da. The data show that BCL-2 BH4 SAHB$_A$ engagement of BAX protein results in a decrease in deuterium uptake by BAX protein, reflective of an overall stabilization of the BAX protein upon BCL-2 BH4 SAHB$_A$ binding (FIG. 15A). A significant relative difference in uptake is observed in the region of BAX α1 and the loop between α1 and α2, indicative of structural stabilization of this region of BAX protein as a result of BCL-2 BH4 SAHB$_A$ binding. This observation is functionally significant, as induced mobility of this region of BAX protein is implicated in transforming BAX protein from an inactive to an activated state.

Figure 15B:
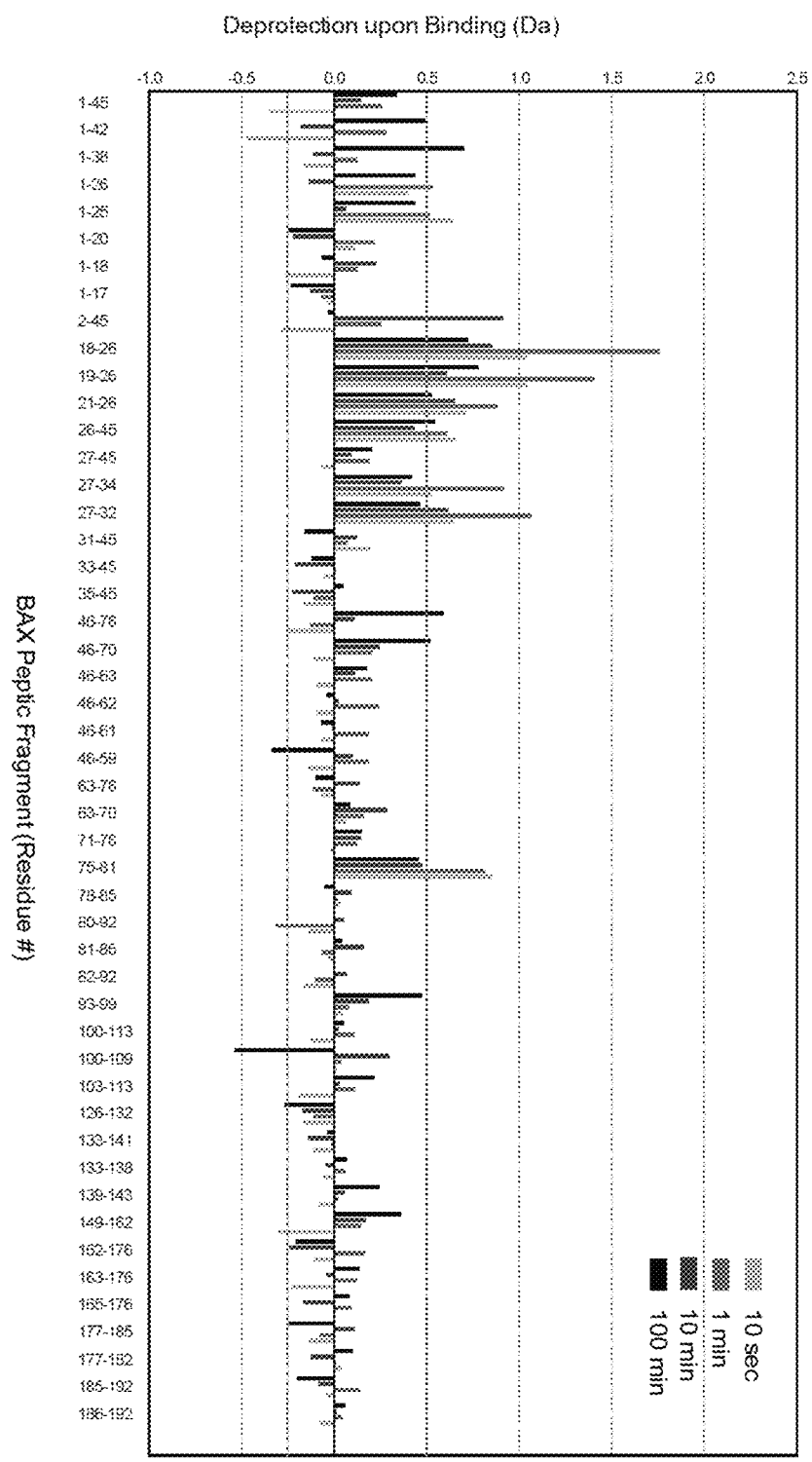
FIG. 15B is a graph of the relative difference in deuterium level in Da over time in different BAX peptides from recombinant BAX labeled with deuterium in the presence of liposomes and the presence or absence of a molar equivalent of BIM SAHB for 10 sec (first bar on left in each set of four bars), 1 min (second bar from left in each set of four bars), 10 min (third bar from left in each set of four bars), 100 min (fourth bar from left in each set of four bars). The data shown are the average of two duplicate experiments where the relative difference (Da) for each peptide is equivalent to the relative deuterium uptake of the corresponding peptide in the BIM SAHB-activated BAX sample minus the relative deuterium uptake of the peptide in the BAX alone control. This HXMS experiment demonstrates the BAX regions that undergo conformational change and thus become exposed for deuterium exchange upon direct activation of BAX by BIM SAHB in the membrane environment.
Figure 15C:
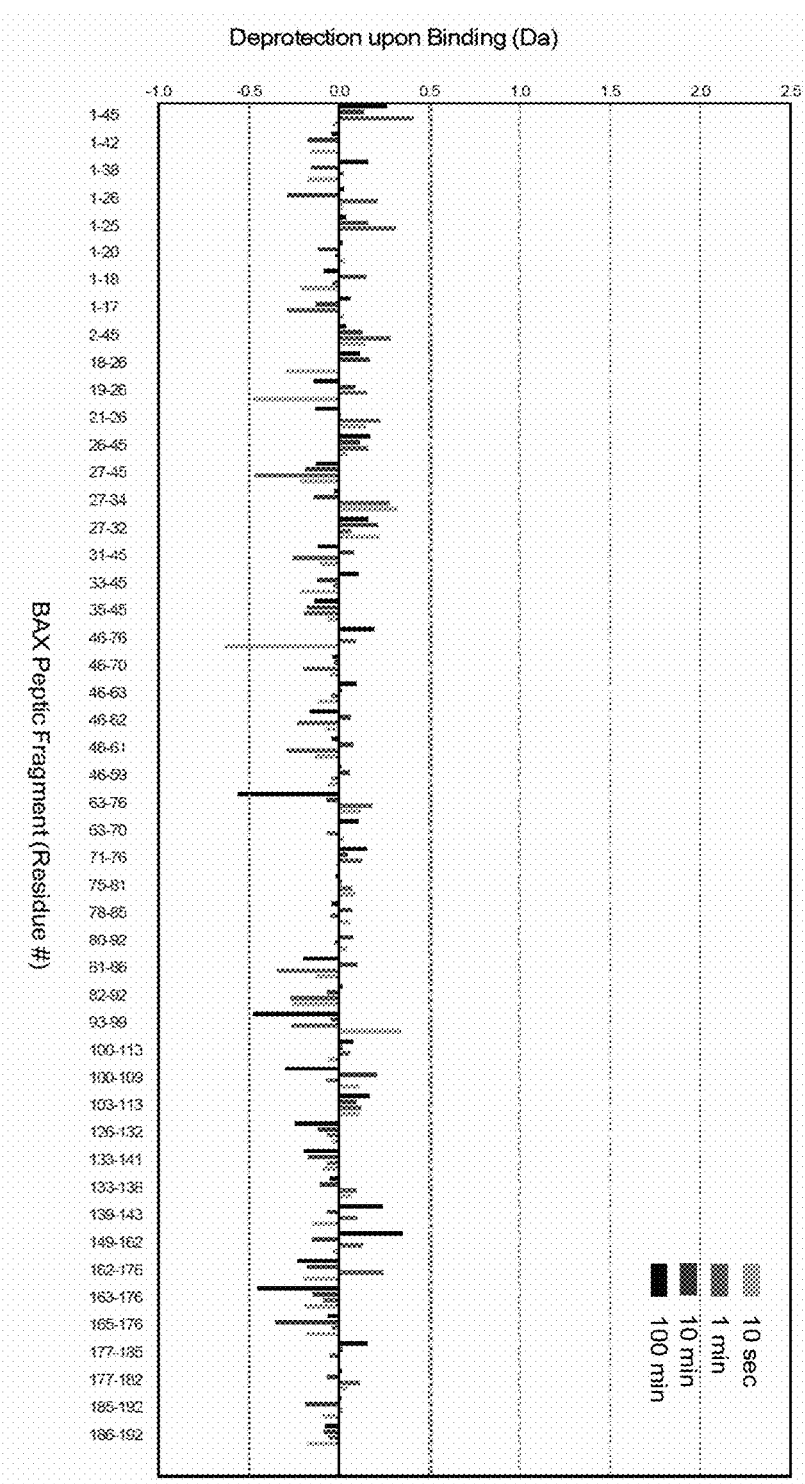
FIG. 15C is a graph of the relative difference in deuterium level in Da over time in different BAX peptides from recombinant BAX labeled with deuterium in the presence of liposomes and the presence or absence of both a molar equivalent of BIM SAHB and a two molar excess of BCL-2 BH4 SAHBA for 10 sec (first bar on left in each set of four bars), 1 min (second bar from left in each set of four bars), 10 min (third bar from left in each set of four bars), 100 min (fourth bar from left in each set of four bars). The data shown are the average of two duplicate experiments where the relative difference (Da) for each peptide is equivalent to the relative deuterium uptake of the corresponding peptide in the BIM SAHB-activated BCL-2 BH4 SAHBA-bound BAX sample minus the relative deuterium uptake of the peptide in the BAX alone control. This experiment demonstrates that BCL-2 BH4 SAHBA can block the changes in BAX conformation induced by BIM SAHB.

The following studies demonstrate that BCL-2 BH4 SAHBA blocks the conformational activation of BAX by BIM SAHB in the membrane context as measured by HXMS. Recombinant BAX protein was pre-equilibrated for 15 min with liposomes in the presence or absence of a molar equivalent of BIM SAHB (FIG. 15B) or a molar equivalent of BIM SAHB and a two molar excess of BCL-2 BH4 SAHBA (FIG. 15C), and then labeled with deuterium for 10 seconds, 1 minute, 10 minutes, and 2 hours. Following the corresponding incubation period in D20 buffer, each sample was quenched with ice-cold guanidine chloride buffer (pH 2.6) and then subjected to proteolysis on ice for 5 minutes. The samples were next injected on a custom Waters NanoA-CUITY UPLC HDX Manager for analysis as described above. Mass spectra were obtained with a Synapt G2 mass spectrometer (Waters Corporation) and analyzed with the DynamX software package (Waters Corporation). The data shown in FIG. 15B are the duplicate of two experiments, where the relative difference (Da) shown for each BAX peptide fragment is equivalent to the relative deuterium uptake of the peptide in the BIM SAHB-activated BAX sample minus the relative deuterium uptake of the corresponding peptide in the BAX alone control. The data show significant differences in uptake (>0.5 Da) in the N-terminal al region, the C-terminal binding pocket, and the BH3 α2 helix where deuterium exposure is increased in these areas in BIM SAHB-activated BAX (FIG. 15B). These regions correspond to the N-terminal 6A7 epitope exposure, disengagement of the C-terminal transmembrane helix by the C-terminal binding pocket, and mobilization of the pro-apoptotic BH3 helix, respectively, which are all hallmarks of the BAX conformational activation pathway (Gavathiotis et al., 2010). Addition of BCL-2 BH4 SAHBA to the BIM SAHB-treated BAX sample results in complete suppression of the differences in relative uptake compared to BAX alone (FIG. 15C). This observation indicates that BCL-2 BH4 SAHBA binding inhibits BAX activation by preserving the inactive, monomeric conformation of BAX. The HXMS studies in FIGS. 15B and 15C used the following methodology. Recombinant BAX was labeled with deuterium in the presence of liposomes and the presence and absence of (1) a molar equivalent of BIM SAHB or (2) a molar equivalent of BIM SAHB and a two molar excess of BCL-2 BH4 SAHBA for 10 sec, 1 min, 10 min, and 2 hr. Following the appropriate incubation period in D20 buffer, each sample was quenched with ice-cold guanidine chloride buffer (pH 2.6) and injected on a custom Waters NanoACQUITY UPLC HDX Manager for analysis as described (Wales et al., 2008) after 5 min proteolysis. Mass spectra were obtained with a Synapt G2 mass spectrometer (Waters Corporation) and analyzed with the DynamX software package (Waters Corporation). Data is the average of two duplicate experiments where the relative difference (Da) for each peptide is equivalent to the relative deuterium uptake of the corresponding peptide in the BIM SAHB-activated BAX sample or the BIM SAHB activated and BCL-2 BH4 SAHBA-bound BAX sample minus the relative deuterium uptake of the peptide in the BAX alone control. A significant relative difference threshold corresponds to 0.5 Da (dashed lines).

Figure 15D:
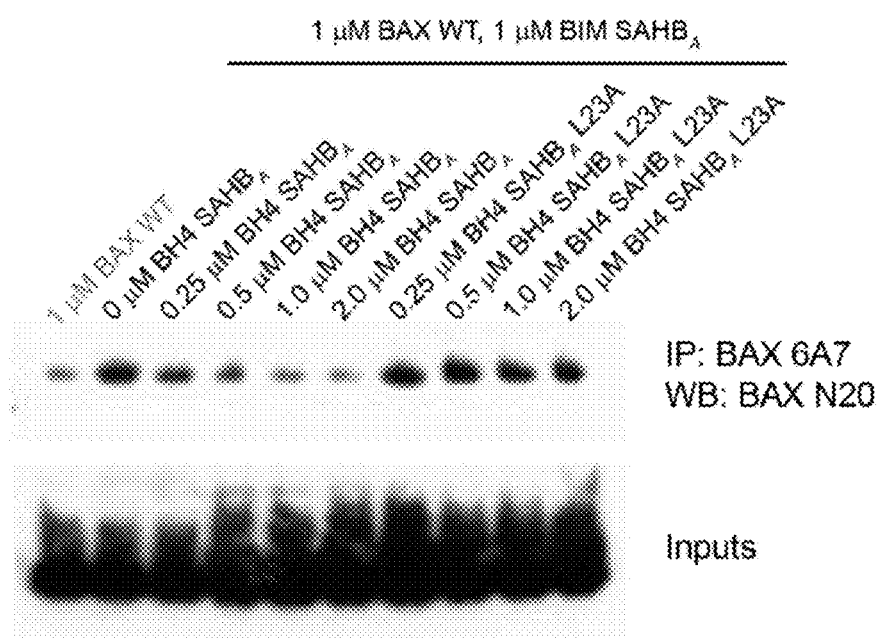
FIG. 15D is an immunoblot demonstrating that the N-terminal conformational change that initiates the BAX activation process is dose-responsively inhibited by addition of BCL-2 BH4 SAHBA, but not the negative control BCL-2 BH4 SAHBA L23A peptide, when added to recombinant BAX in the presence of a molar equivalent of the BAX-activating BIM SAHB peptide and liposomes. The activated state of BAX is detected by immunoprecipitation with an antibody specific for an N-terminal epitope that becomes exposed upon BAX activation. The data shown are representative of three independent experiments.

The following experiment demonstrates that BCL-2 BH4 SAHBA dose-responsively blocks BIM SAHB-triggered direct BAX activation, as measured by BAX 6A7 immunoprecipitation. An additional experiment was performed to determine whether BCL-2 BH4 SAHB binding would be capable of preventing the N-terminal unfolding characteristic of activated BAX. In this experiment, recombinant BAX was incubated with liposomes and a molar equivalent of BIM SAHB in the presence of increasing amounts of BCL-2 BH4 SAHBA or BCL-2 BH4 SAHBA L23A. After a 30 min pre-incubation period to allow for activation to proceed, the liposomal mixtures were subjected to immunoprecipitation with the BAX 6A7 antibody (Santa Cruz), which specifically recognizes the N-terminal epitope on BAX (residues 12-24) that is exposed during activation (Hsu et al., 1997). Immunoprecipitated protein was resolved by electrophoresis and immunoblotted with an antibody specific for BAX. The immunoblot shows that in the absence of BCL-2 BH4 SAHBA, BIM SAHB-activated BAX is recognized by the N-terminal epitope-specific antibody, whereas addition of BCL-2 BH4 SAHBA dose-responsively reduces 6A7 reactivity (FIG. 15D). Importantly, the L23A mutant version of the BH4 peptide, which was shown in the liposomal release assay to disrupt its inhibitory activity, had no effect on BAX 6A7 reactivity. The BAX 6A7 immunoprecipitation was carried out as follows. Recombinant BAX (1 μM) was mixed with liposomes and 1 μM BIM SAHB in the presence of increasing doses of BCL-2 BH4 SAHBA or BCL-2 BH4 SAHBA L23A (0 μM, 0.25 μM, 0.5 μM, 1.0 μM, and 2.0 μM). Following a 30 min incubation at room temperature, the mixture was immunoprecipitated with α-BAX 6A7 (Santa Cruz) and resolved by electrophoresis. Immunoblotting of the immunoprecipitated sample and inputs was performed with α-BAX N20 (Santa Cruz). Data is representative of three independent experiments.

In an additional set of experiments, photoreactive SAHBs (pSAHBs) were generated as described in Braun et al. (*Chem. Biol.* 17:1325-1333, 2010) and cross-linked to recombinant BAX protein by incubation under UV light for 2 hours. Following the cross-linking, the samples were resolved on a 4-12% Bis-Tris gel, excised, digested with trypsin, and prepared for analysis by LC-MS/MS in a LTQ Orbitrap Discovery hybrid mass spectrometer (Thermo-Fisher, San Jose, Calif.). MS/MS spectra were searched using the SEQUEST algorithm (Eng et al., *J. Am. Soc. Mass Spectrom.* 5:976-989, 1994) against a partially tryptic database containing BAX, trypsin, and common keratin contaminants. P-xylene-bis-pyridinium bromide (BPA)-cross-linked tryptic fragments were identified by searching for the variable modification corresponding to the mass of the tryptic BAX fragment plus the BPA-containing pSAHB fragment. The data shown in FIGS. 16-18 are presented as the frequency of crosslink occurrence across the polypeptide sequence of BAX and mapped onto the BAX NMR structure (Suzuki et al., *Cell* 103:645-654, 2000; PDB: 1F16). The greatest density of cross-links across the three BCL-2 BH4 pSAHBs localize to residues spanning amino acids 70-90 of BAX localized at the C-terminal side of the protein, in the vicinity of the C-terminal α9 helix (FIGS. 16-18).

Figure 19:
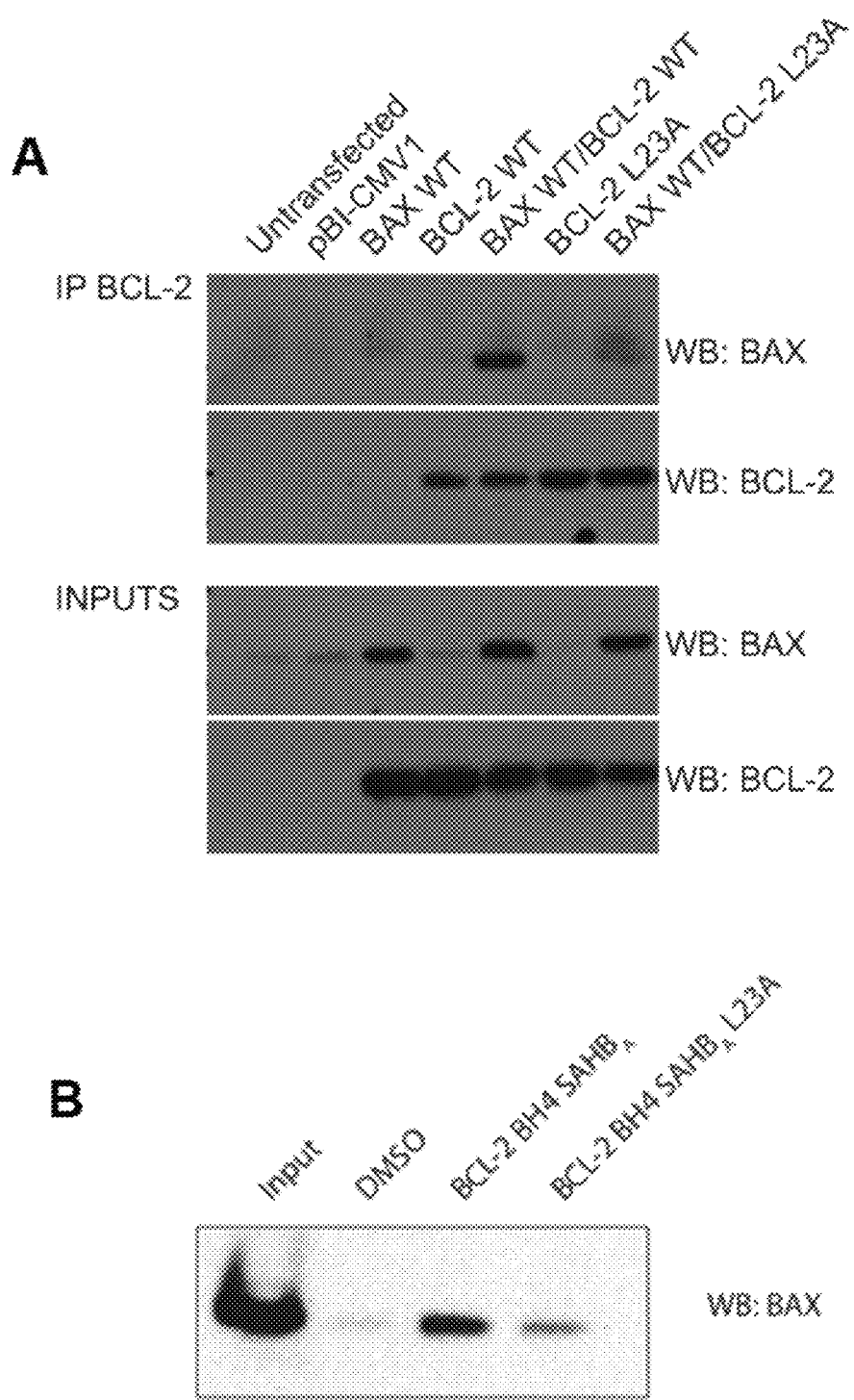
FIG. 19A is an immunoblot demonstrating that native BAX protein is specifically immunoprecipitated from a HeLa cell lysate by streptavidin pull-down of added biotinylated-BCL-2 BH4 $SAHB_A$, whereas the corresponding BCL-2 BH4 $SAHB_A$ construct containing an L23A point mutation markedly reduces the interaction with native BAX. The data shown are representative of at least three independent experiments.
FIG. 19B are immunoblots (developed using antibodies that bind to BCL-2 or antibodies that bind to BAX) showing the proteins immunoprecipitated using an anti-BCL-2 antibody from the lysate of HeLa cells transfected with a control vector (pBI-CMV1), a wild type BAX expression vector (BAX WT), a wild type BCL-2 expression vector (BCL-2 WT), a dual BAX WT and BCL-2 WT expression vector (BAX WT/BCL-2 WT), an L23A BCL-2 expression vector (BCL-2 L23A), and a dual BAX WT and BCL-2 L23A expression vector (BAX WT/BCL-2 L23A). Also shown is an immunoblot of corresponding lysates used to perform the immunoprecipitation with the anti-BCL-2 antibodies. The data shown are representative of three independent experiments.

Example 6. Mutation of L23A of the BCL-2 BH4 Domain Impairs Interaction of BCL-2 with BAX HeLa cell lysates (0.5 mg) were incubated with vehicle (DMSO), biotinylated BCL-2 BH4 SAHB$_A$ (20 μM), or BCL-2 BH4 SAHB$_A$ L23A (20 μM) for 16 hrs at 4° C. prior to addition of high-capacity streptavidin agarose resin (Thermo Scientific). After three successive washes, associated protein was eluted from the resin into LDS sample buffer and analyzed by Western blot with the anti-BAX N20 antibody (Santa Cruz). BCL-2 BH4 SAHB$_A$ specifically interacted with endogenous BAX, whereas BCL-2 BH4 SAHB$_A$ L23A pulled down markedly less BAX protein, consistent with disruption of the interaction due to L23A point mutagenesis of the binding interface (FIG. 19B). The immunoblot in FIG. 19B is representative of three independent experiments.

Bcl-2 and Bax cDNA was cloned into the pBI-CMV1 vector (Clontech), which allows for bidirectional expression of both genes under the control of one enhancer. Twenty-four hours after transient transfection of HeLa cells with the pBI-CMV1 constructs, the cells were lysed and the isolated lysates subjected to immunoprecipitation with the anti-BCL-2 sc-509 antibody (Santa Cruz Biotechnology). Following resolution by gel electrophoresis and transfer to a PVDF membrane, Western blotting of the co-immunoprecipitated protein was performed using the anti-BAX N20 antibody (Santa Cruz Biotechnology). The immunoblot shown in FIG. 19A is representative of three independent experiments.

Figure 20A:
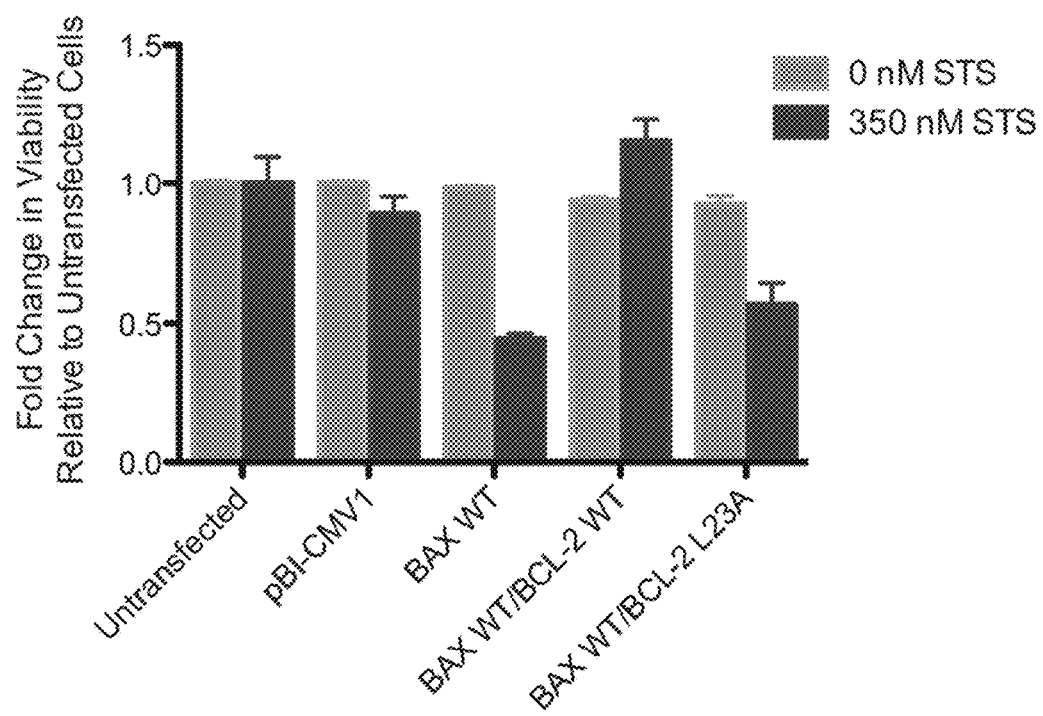
FIG. 20A is a graph of the fold change in viability of untransfected HeLa cells and HeLa cells transfected with the control expression vector (pBI-CMV1), a wild type BAX expression vector (BAX WT), a dual BAX WT and a BCL-2 wild type expression vector (BAX WT/BCL-2 WT), and a dual BAX WT and a L23A BCL-2 expression vector (BAX WT/BCL-2 L23A) in the absence versus the presence of 350 nM staurosporine (relative to untransfected control cells). The data shown are representative of at least three independent experiments. The error bars represent mean±SD of viability assays performed in triplicate. The data shown are representative of at least three independent experiments.

Viability of the transfected cells subjected to 24-hour treatment with 325 nM staurosporine or no treatment with staurosporine was determined by addition of CellTiter-Glo reagent (Promega). The data shown in FIG. 20A are representative of three independent experiments.

The data in FIG. 19A show that anti-BCL-2 antibody immunoprecipitates both wild-type BCL-2 and L23A BCL-2 isoforms, but upon co-expression with BAX, only wild-type BCL-2 co-precipitates with BAX, with L23A mutagenesis of BCL-2 abrogating the interaction of BCL-2 with BAX. Correspondingly, staurosporine treatment of HeLa cells stably expressing the various constructs and construct pairs, induces apoptosis of BAX-overexpressing HeLa cells, but not wild-type BCL-2 and BAX co-expressing cells (FIG. 20A). This BCL-2-based rescue is negated upon co-expression of BAX with the L23A mutant form of BCL-2 (FIG. 20A). These data indicate that the BH4 domain of BCL-2 represents an important interface for BAX interaction and, when disrupted by mutagenesis, functionally impairs the anti-apoptotic function of BCL-2, resulting in BAX-mediated apoptosis.

Figure 20B:
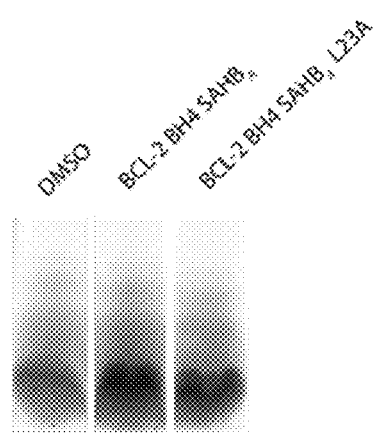
FIG. 20B is a fluorescence scan of electrophoresed cell lysates showing cellular uptake of BCL-2 BH4 SAHB peptides. Cell lysates derived from cells treated with FITC-BCL-2 BH4 SAHBA, FITC-BCL-2 BH4 SAHBA L23A, or a DMSO vehicle control were resolved by electrophoresis and then evaluated by fluorescence scan. Cellular uptake of FITC labeled BCL-2 BH4 SAHBs is demonstrated by increased fluorescent signal in the cell lysate relative to background. The data shown are representative of two independent experiments.

The following experiments demonstrate that FITC-labeled BH4 stapled peptides are cell permeable. Wild-type mouse embryonic fibroblasts (MEFs) were treated with 2 µM FITC-BCL-2 BH4 SAHBA, FITC-BCL-2 BH4 SAHBA L23A, or DMSO in serum-free media for 4 hrs. Following treatment, the cells were incubated with trypsin for 10 min then washed in PBS to remove extracellular peptide. The cells were lysed and fluorescence was detected following electrophoresis with a Typhoon laser scanner (GE Healthcare). The fluorescent scan shows FITC signal above background (DMSO) levels in the cells treated with FITC-BCL-2 BH4 SAHBA and FITC-BCL-2 BH4 SAHBA L23A (FIG. 20B). These data indicate that FITC-BCL-2 BH4 SAHBA and FITC-BCL-2 BH4 SAHBA L23A can achieve cellular uptake. In this experiment the fluorescence scan of cell lysates was performed as follows. Wild-type mouse embryonic fibroblasts (MEFs) were plated in 6-well plate format at 500,00 cells/well. Twenty-four hours later, the cells were washed with PBS and treated with 2 µM FITC-BCL-2 BH4 SAHBA, FITC-BCL-2 BH4 SAHBA L23A, or an equivalent volume of DMSO (vehicle control) in serum-free media (OPTI-MEM) for 4 hrs. Following treatment, cells were washed with PBS, incubated with DMEM containing 0.25% trypsin for 10 min and lysed in 1% CHAPS buffer (150 mM NaCl, 50 mM Tris, pH 7.4). Cell lysates were resolved by electrophoresis and visualized by fluorescent scanning with a Typhoon imager (GE Healthcare Life Sciences). Data shown is representative of two independent experiments.

Figure 20C:
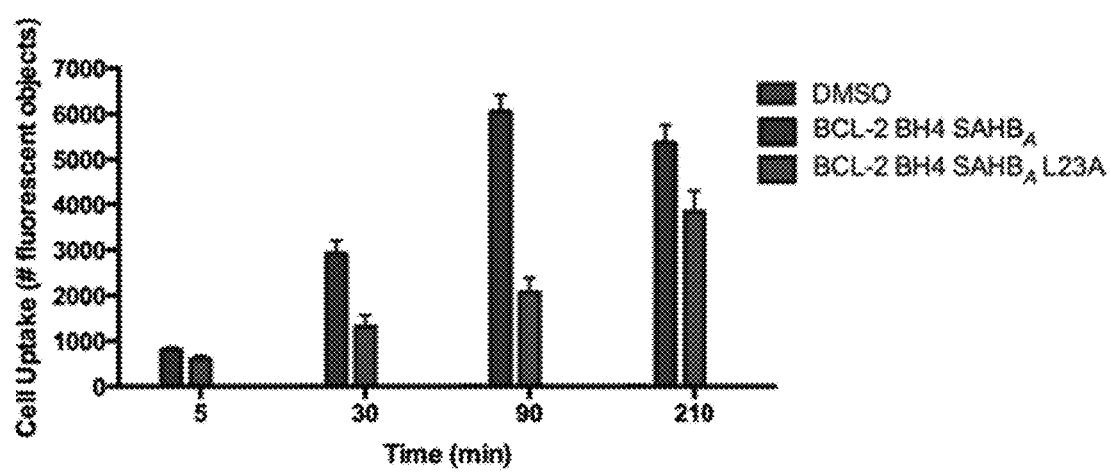
FIG. 20C is a time course experiment demonstrating cellular uptake of FITC-labeled BH4 SAHBs and a DMSO vehicle control at discrete time points. Cells are washed thoroughly before detection of FITC signal with a laser scanning cytometer. The data shown are an average of experiments performed in quadruplicate where the number of fluorescent objects detected per sample corresponds to cellular uptake at each time point post treatment.

In a complementary experiment, the time course of cellular uptake for FITC-labeled BH4 SAHBs was monitored, demonstrating the time-dependent uptake of BH4 SAHBs. Wild-type MEFs were treated with 2 µM FITC-BCL-2 BH4 SAHBA, FITC-BCL-2 BH4 SAHBA L23A, or DMSO in a 96-well plate format in quadruplicate. At 5, 30, 90, and 210 min post treatment, wells were washed with 10% FBS in phenol red-free media to remove non-specifically bound peptides. The cells were imaged with a Blueshift IsoCyte laser scanning cytometer (Blueshift Biotech), which quantifies fluorescence according to the number of fluorescent objects detected in each image. The number of objects identified was plotted over time (FIG. 20C) showing the time-dependent cell uptake of FITC-BCL-2 BH4 SAHBs. In this experiment the confocal microscopy was performed as follows. Wild-type MEFs were plated in 96-well plate format at a density of 40,000 cells per well and treated in quadruplicate 24 hrs later with 2 µM FITC-BCL-2 BH4 SAHBA, FITC-BCL-2 BH4 SAHBA L23A, or an equivalent volume of DMSO (vehicle control) in serum-free media (OPTI-MEM). After 5, 30, 90, and 210 min the cells were washed thoroughly with 10% FBS in phenol red-free media and imaged with a Blueshift IsoCyte laser scanning cytometer (Blueshift Biotech) to quantify fluorescence according to the number of fluorescent objects detected in each image. Data is representative of 2 independent experiments.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An internally cross-linked polypeptide comprising the amino acid sequence of EIVMKYIHYKLSQRGYEWDA (SEQ ID NO: 1),
wherein:
the side chains of amino acid residues at positions 8 and 12 of SEQ ID NO: 1 or the side chains of amino acid residues at positions 13 and 17 of SEQ ID NO: 1 are replaced by an internal staple; and
the internally cross-linked polypeptide is capable of specifically binding to a BAX protein; and
optionally, the amino acid residue at position 4 of SEQ ID NO: 1 is substituted with another amino acid.

2. The cross-linked polypeptide of claim 1, wherein the side chains of amino acid residues 13 and 17 of SEQ ID NO: 1 are replaced by an internal staple.

3. A pharmaceutical composition comprising one or more of the cross-linked polypeptides of claim 1.

4. A kit for identifying agents that interact with and/or modulate the activity of BAX protein comprising one or more of the cross-linked polypeptides of claim 1 and a polypeptide comprising the amino acid sequence of a BAX polypeptide.

5. A compound comprising one or more of the cross-linked polypeptides of claim 1.

6. The cross-linked polypeptide of claim 1, wherein the side chains of the amino acid residues at positions 8 and 12 of SEQ ID NO: 1 are replaced by an internal staple.

* * * * *

UNITED STATES PATENT AND TRADEMARK OFFICE
CERTIFICATE OF CORRECTION

| | | |
|---|---|---|
| PATENT NO. | : 10,106,590 B2 | Page 1 of 1 |
| APPLICATION NO. | : 14/777391 | |
| DATED | : October 23, 2018 | |
| INVENTOR(S) | : Loren D. Walensky, Michelle L. Stewart and Lauren Barclay | |

It is certified that error appears in the above-identified patent and that said Letters Patent is hereby corrected as shown below:

On the Title Page

Left column, Item (71) Applicant:
Delete "Institutes," and insert -- Institute, --, therefor.

Signed and Sealed this
Fifteenth Day of January, 2019

Andrei Iancu
*Director of the United States Patent and Trademark Office*